United States Patent [19]

Yoshida

[11] 4,320,772
[45] Mar. 23, 1982

[54] METHYL SUBSTITUTED OXOBICYCLO-4,4,0-DECANE DERIVATIVES, PROCESS FOR PREPARING SAME AND ORGANOLEPTIC USES THEREOF

[75] Inventor: Takao Yoshida, West Long Branch, N.J.

[73] Assignee: International Flavors & Fragrances Inc., New York, N.Y.

[21] Appl. No.: 182,451

[22] Filed: Aug. 29, 1980

[51] Int. Cl.$^3$ ............................................. A24B 5/30
[52] U.S. Cl. ................................................. 131/276
[58] Field of Search ............................ 131/276, 275

*Primary Examiner*—V. Millin
*Attorney, Agent, or Firm*—Arthur L. Liberman

[57] ABSTRACT

Described are compounds having the generic structure:

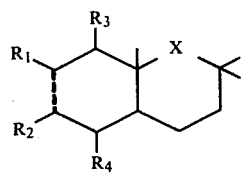

wherein the dashed line represents a carbon-carbon single bond or a carbon-carbon double bond; wherein X represents the moieties:

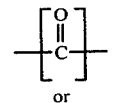

or

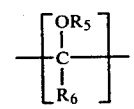

wherein $R_1$, $R_2$, $R_3$ and $R_4$ represent hydrogen or methyl with the proviso that (i) at least three of $R_1$, $R_2$, $R_3$ and $R_4$ represent hydrogen and (ii) when the dashed line is a carbon-carbon single bond and X is:

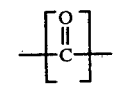

then one of $R_1$, $R_2$, $R_3$ or $R_4$ is methyl and the other represents hydrogen; wherein $R_5$ represents hydrogen, MgX, MgR$_7$, CdR$_7$, ZnR$_7$, Na, K or Li; wherein X represents Chloro, Bromo or Iodo; wherein $R_6$ represents hydrogen or methyl; and wherein $R_7$ represents lower alkyl; and uses thereof for their organoleptic properties in augmenting or enhancing or enhancing the aromas or tastes of perfumes, perfumed articles, foodstuffs, chewing gums, smoking tobaccos, toothpastes, medicinal products, chewing tobacco and smoking tobacco articles, as well as processes for preparing same.

4 Claims, 74 Drawing Figures

GLC PROFILE FOR EXAMPLE I.

FIG. 2 MASS SPECTRUM FOR EXAMPLE I.

NMR SPECTRUM FOR EXAMPLE I.

IR SPECTRUM FOR EXAMPLE I.

GLC PROFILE FOR EXAMPLE II.

MASS SPECTRUM FOR EXAMPLE II.

IR SPECTRUM FOR EXAMPLE II.

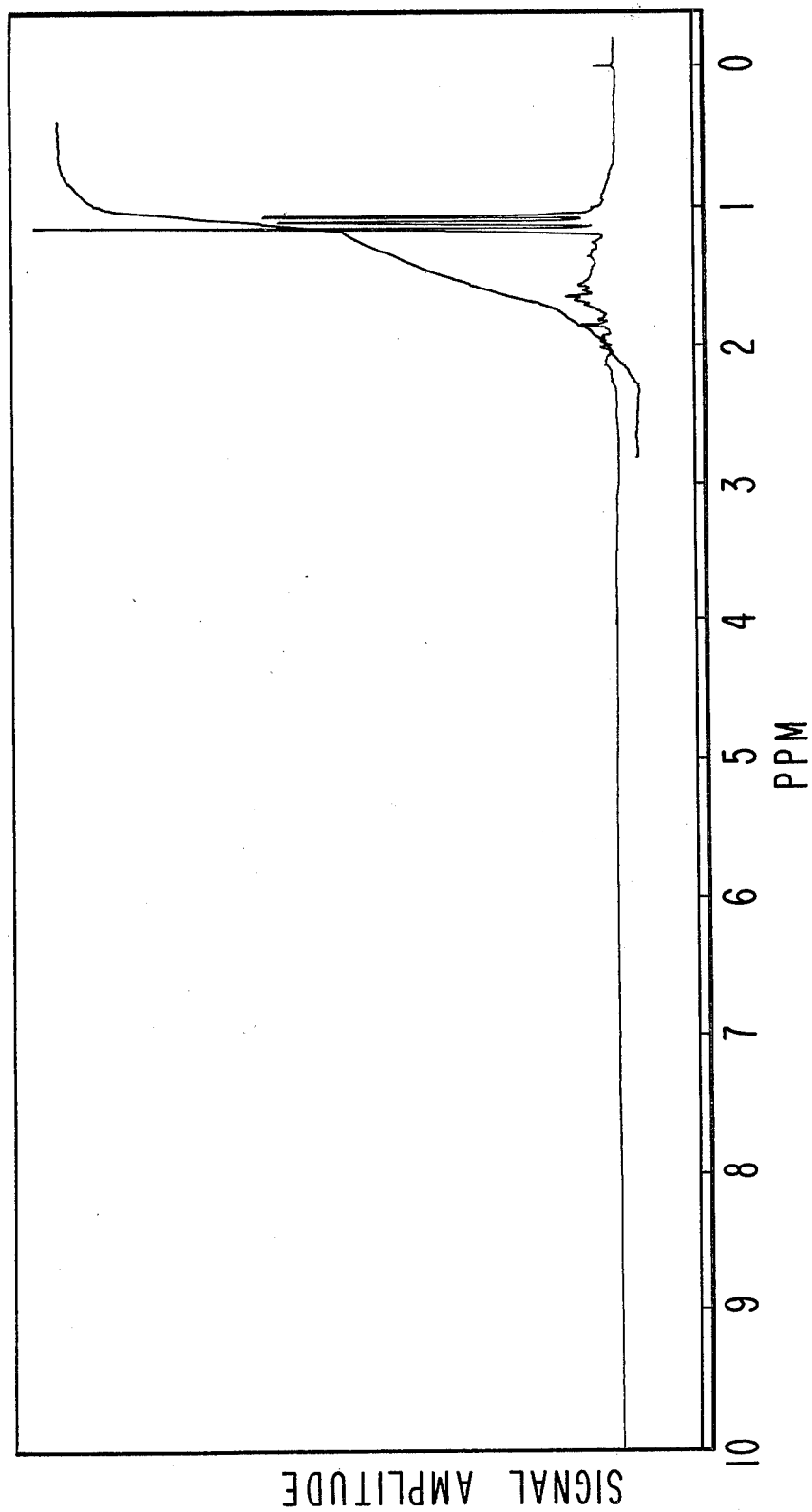

GLC PROFILE / MAJOR PRODUCT, EXAMPLE III.

GLC PROFILE FOR EXAMPLE III.

MASS SPECTRUM FOR EXAMPLE III

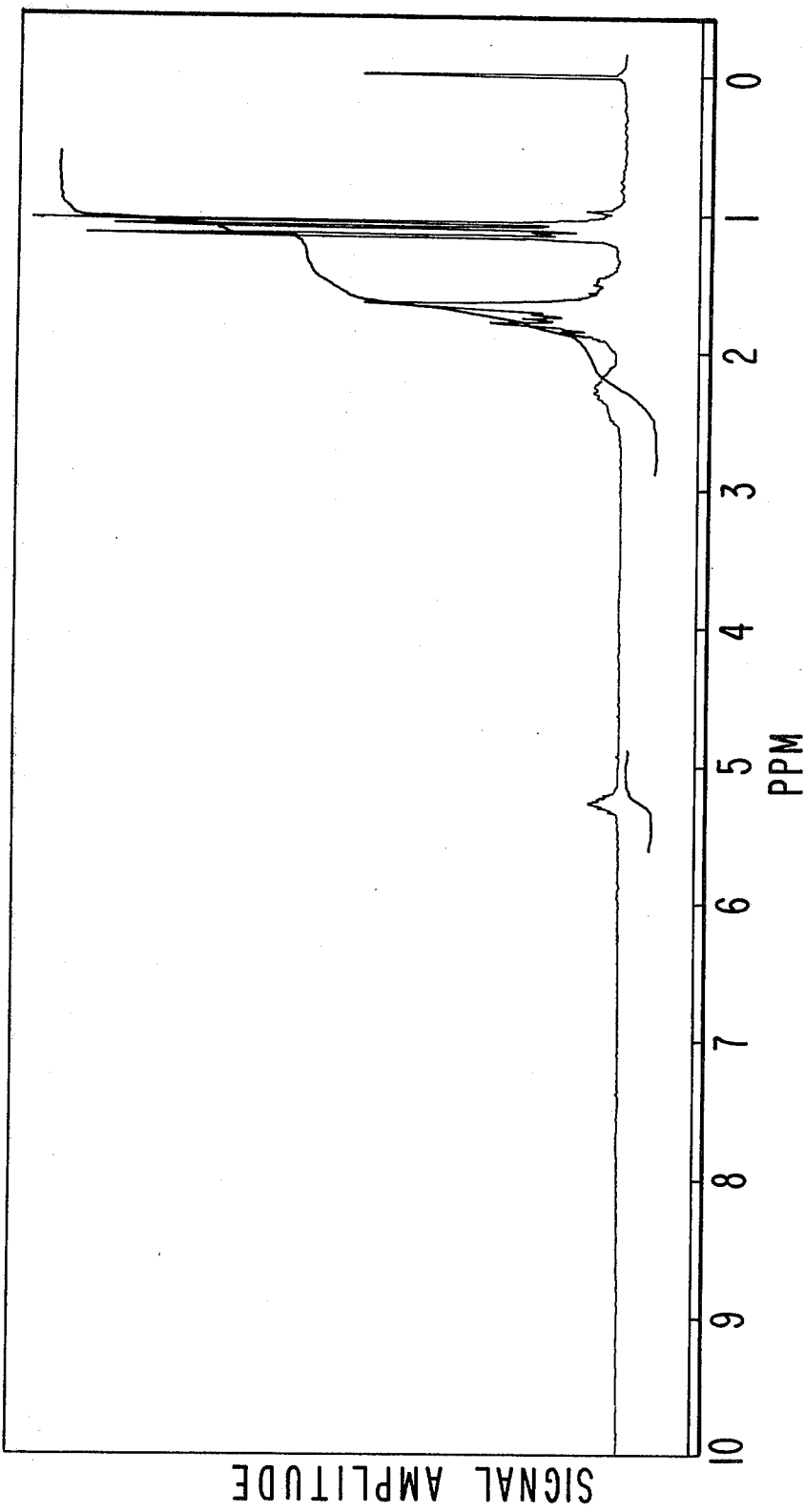

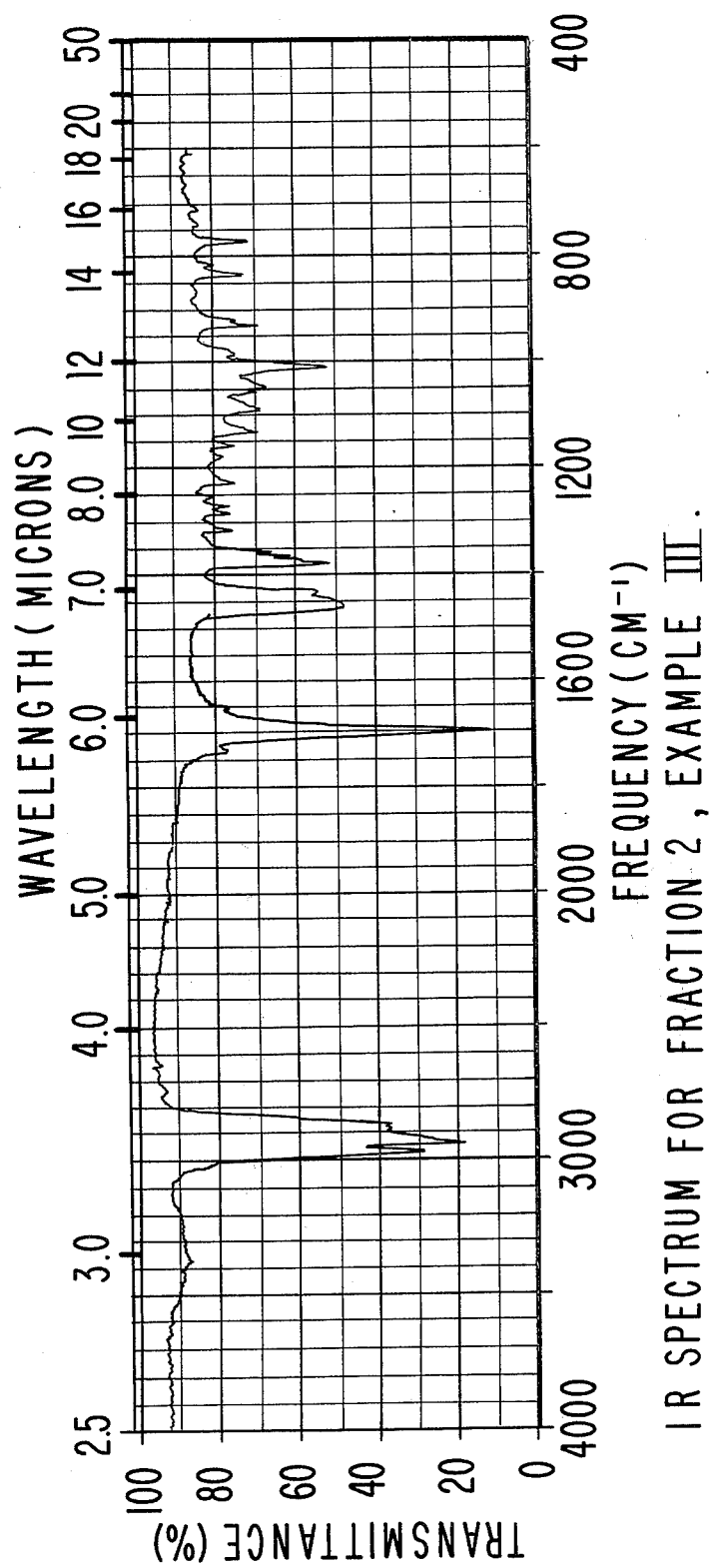

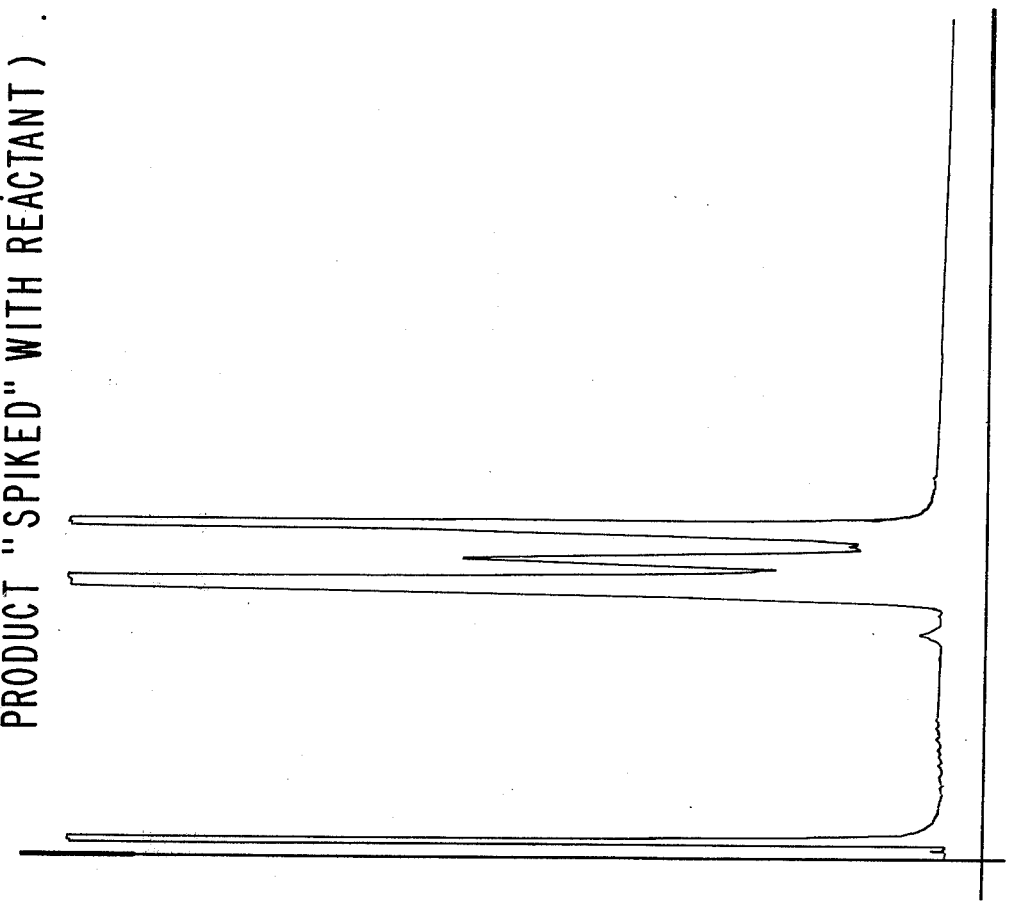
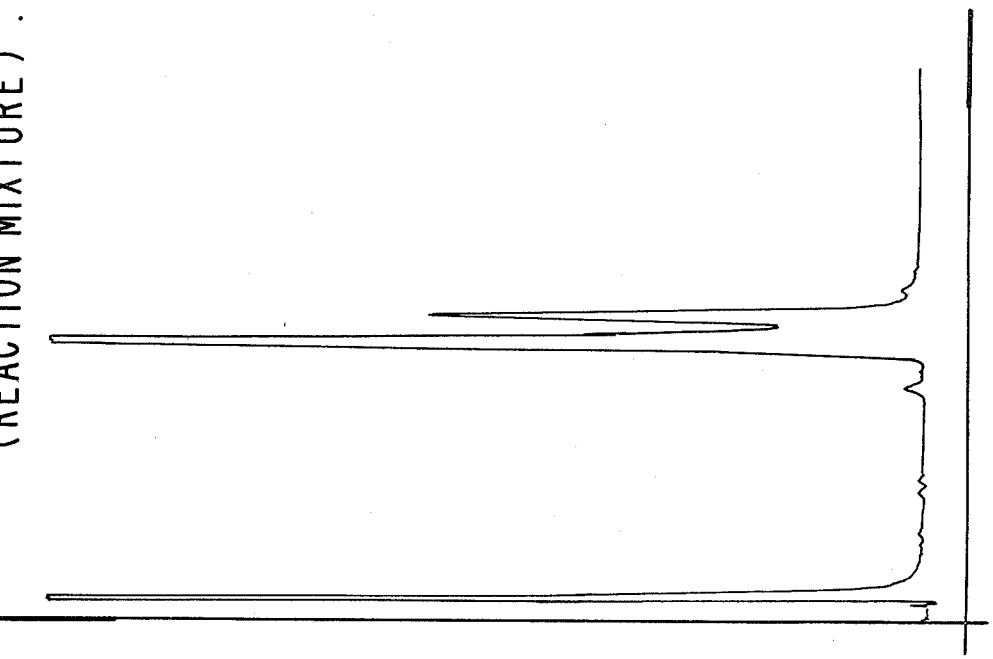

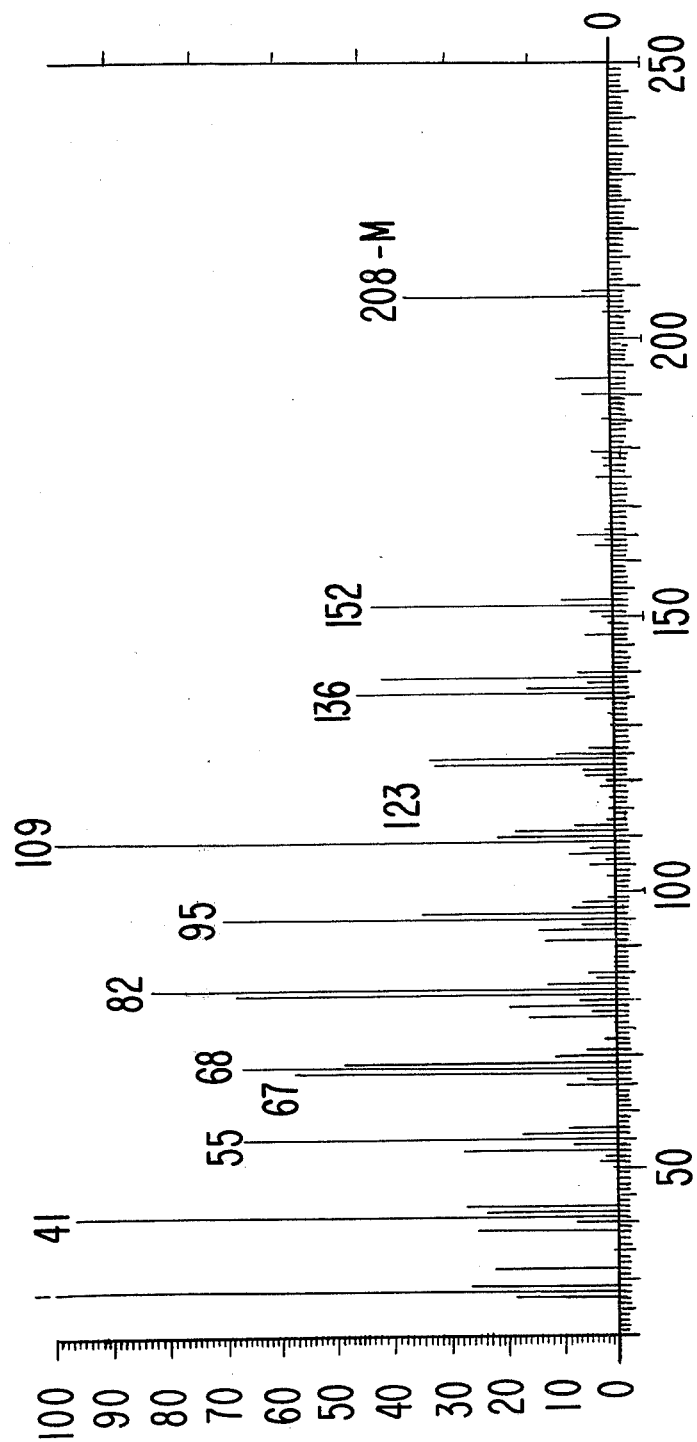
FIG.14 MASS SPECTRUM FOR EXAMPLE IV.

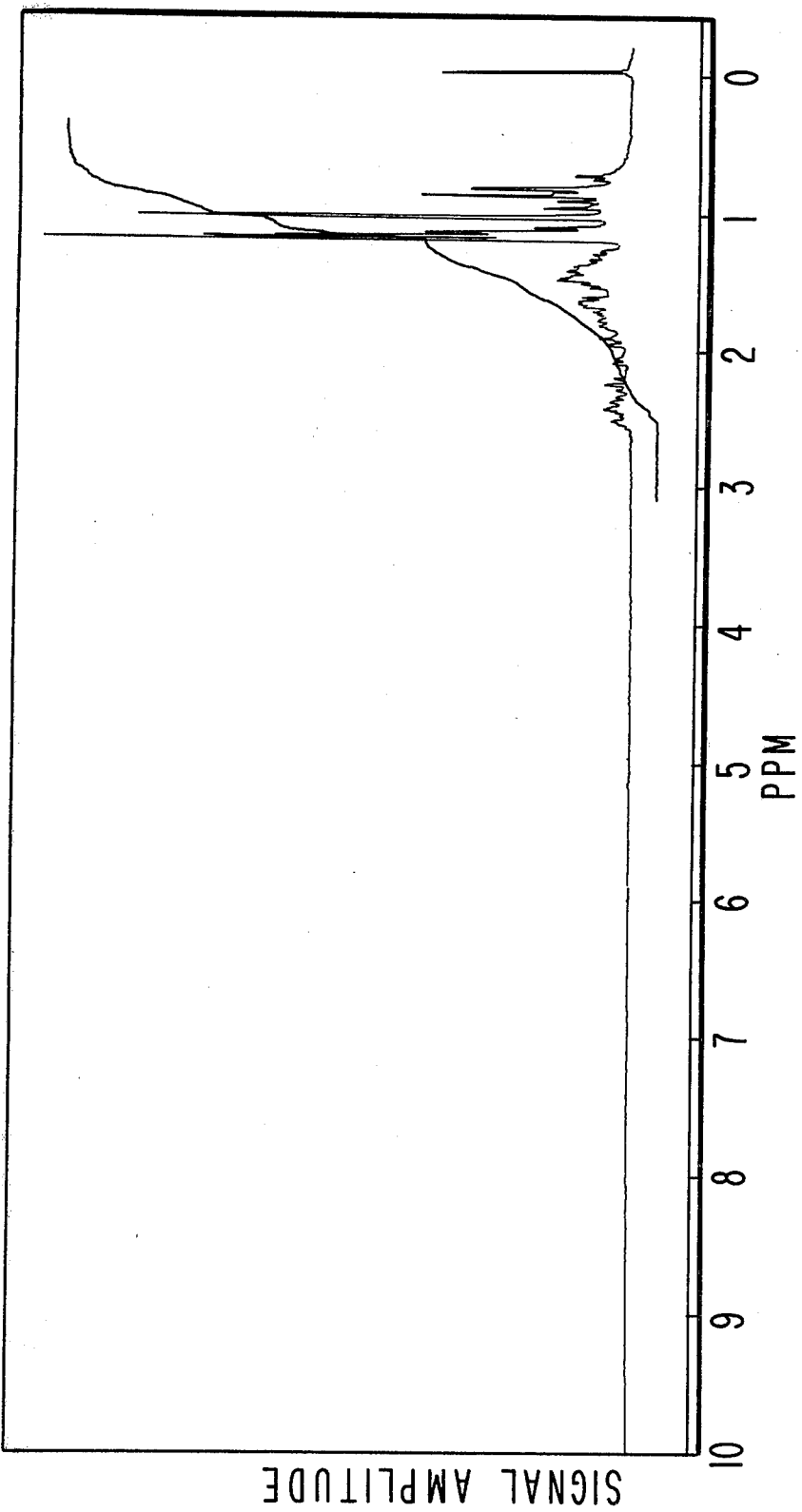
FIG. 15 NMR SPECTRUM FOR FRACTION 3 OF EXAMPLE IV.

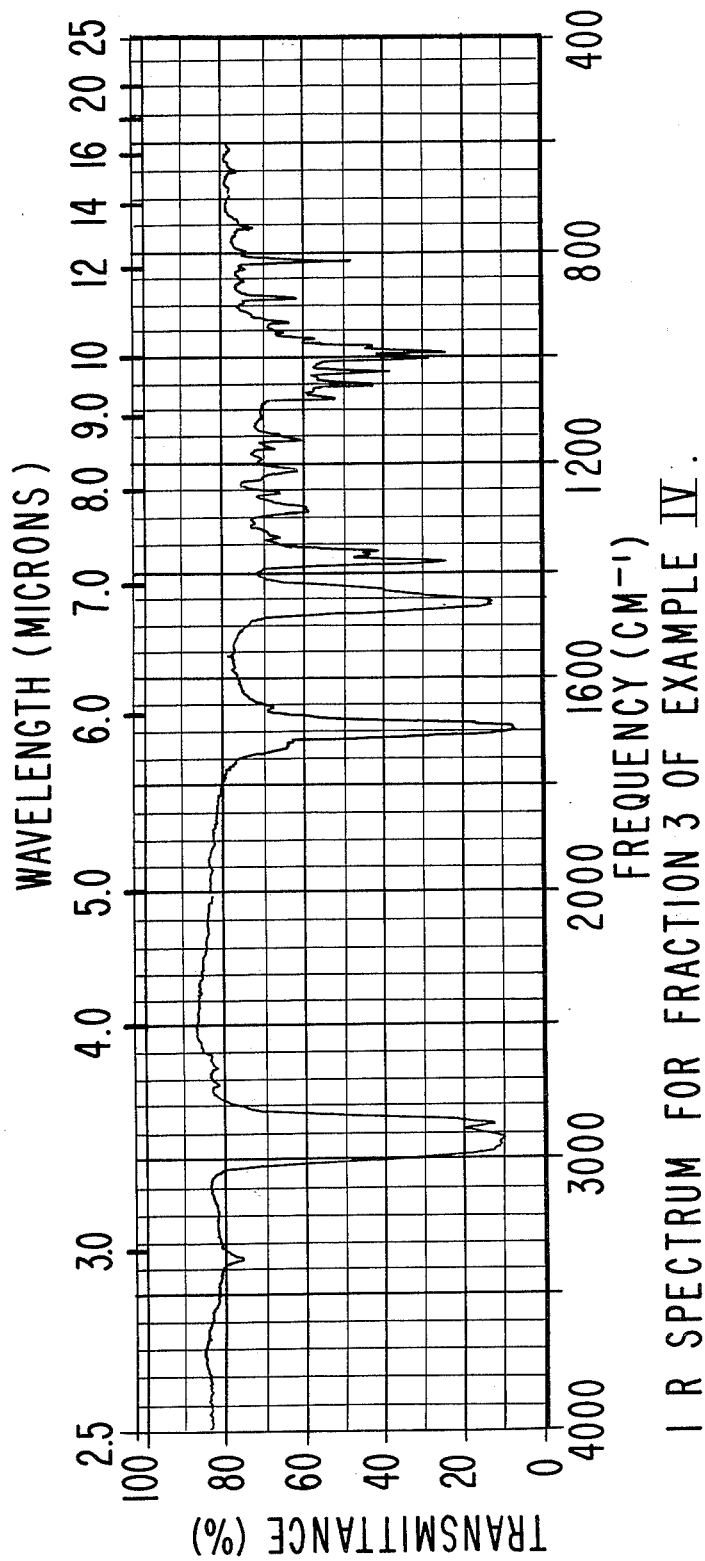

GLC PROFILE FOR EXAMPLE V.

MASS SPECTRUM FOR EXAMPLE V.

FIG. 19 NMR SPECTRUM FOR EXAMPLE V.

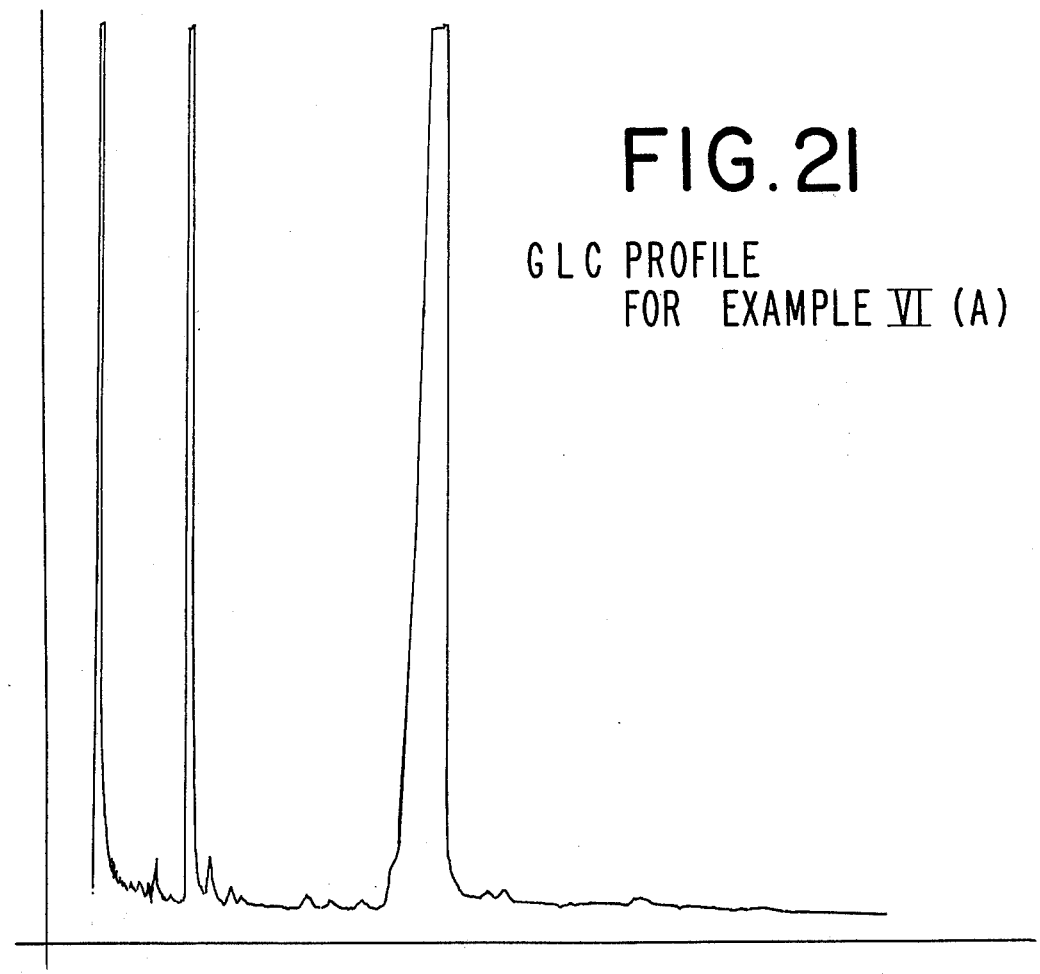
FIG.21
GLC PROFILE FOR EXAMPLE VI (A)
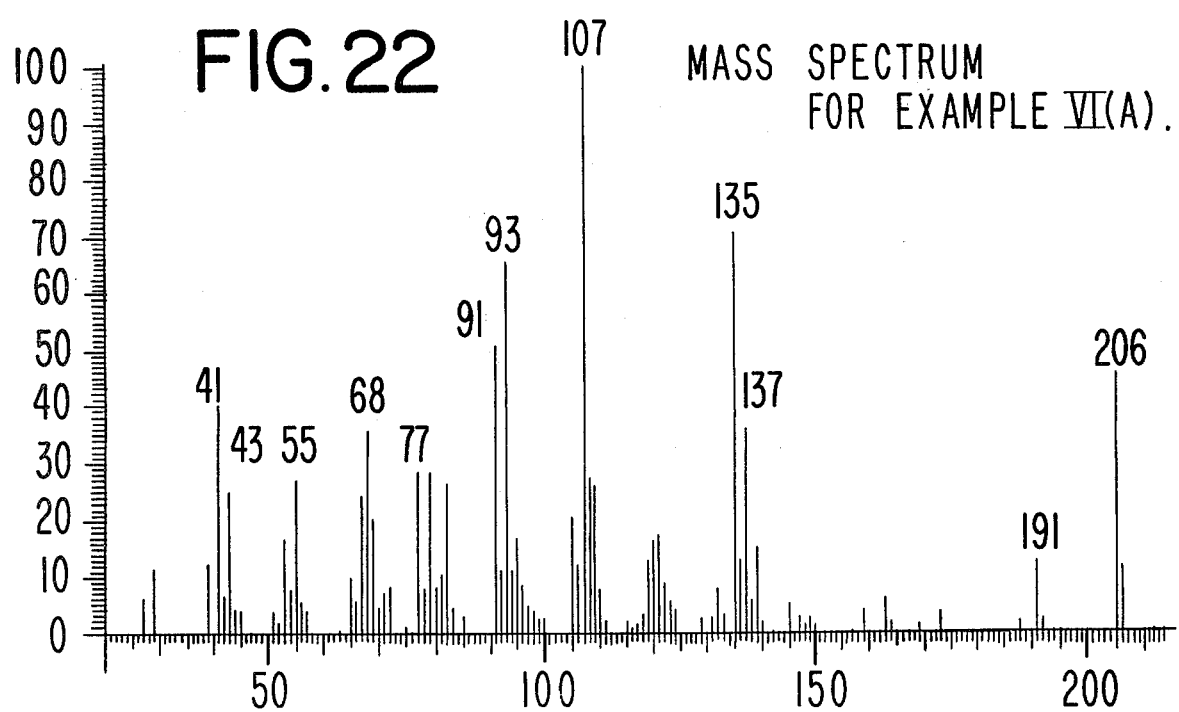
FIG.22 MASS SPECTRUM FOR EXAMPLE VI(A).

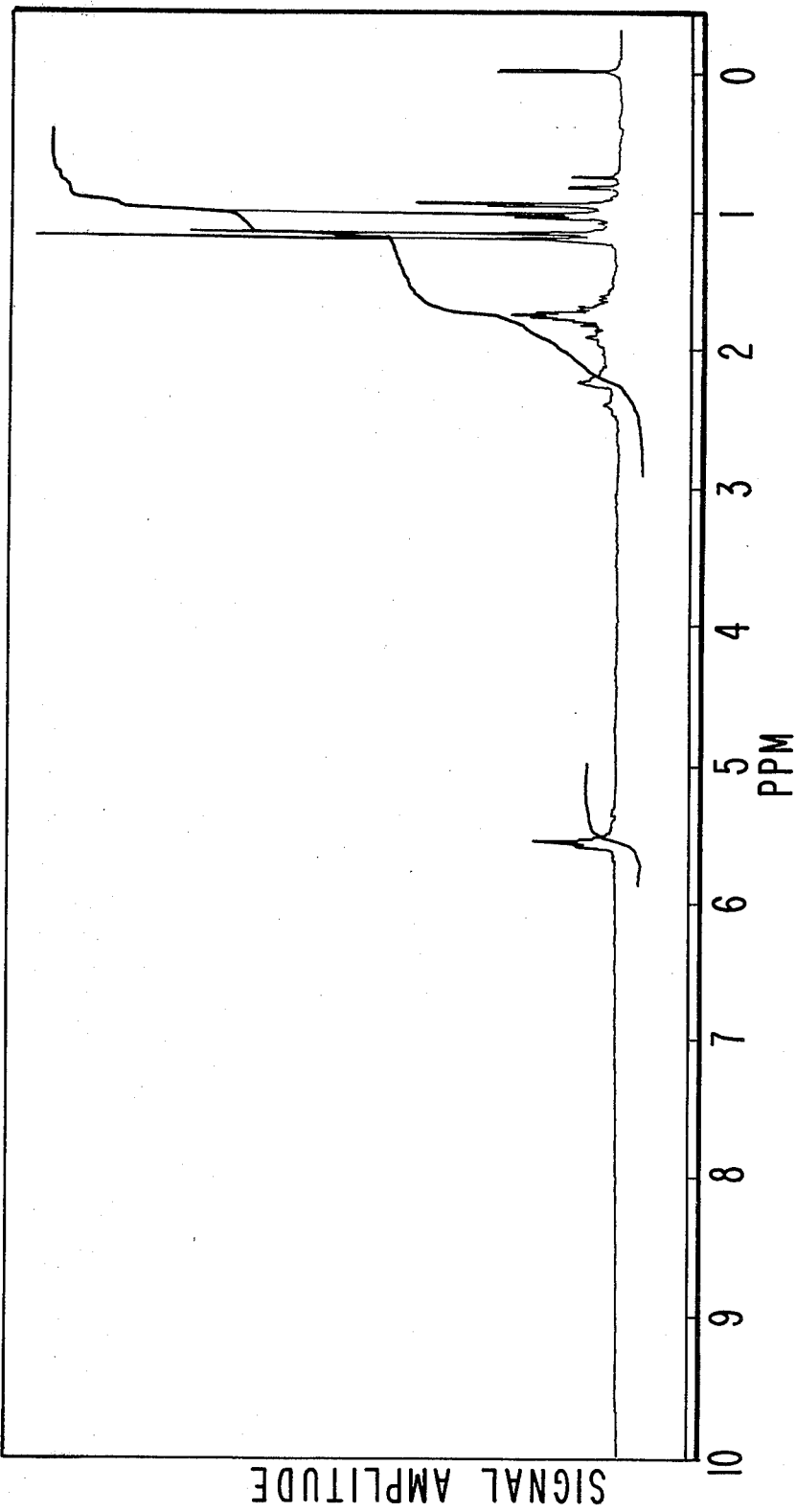
FIG. 23 NMR SPECTRUM FOR FRACTION 7 OF EXAMPLE VI(A).

IR SPECTRUM FOR FRACTION 7 OF EXAMPLE VI (A).

GLC PROFILE FOR BULKED FRACTIONS 2-7 OF EXAMPLE VI (B).

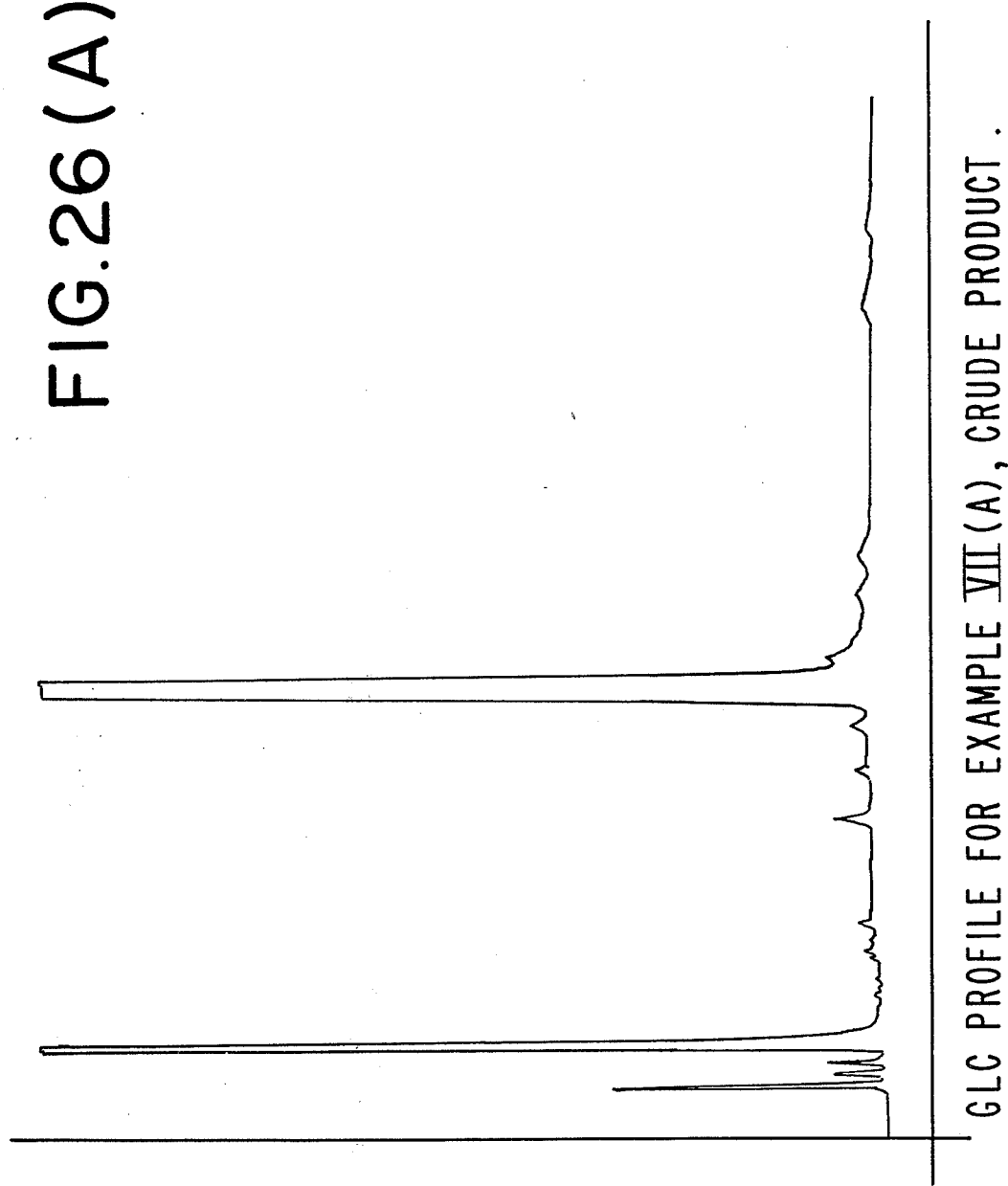

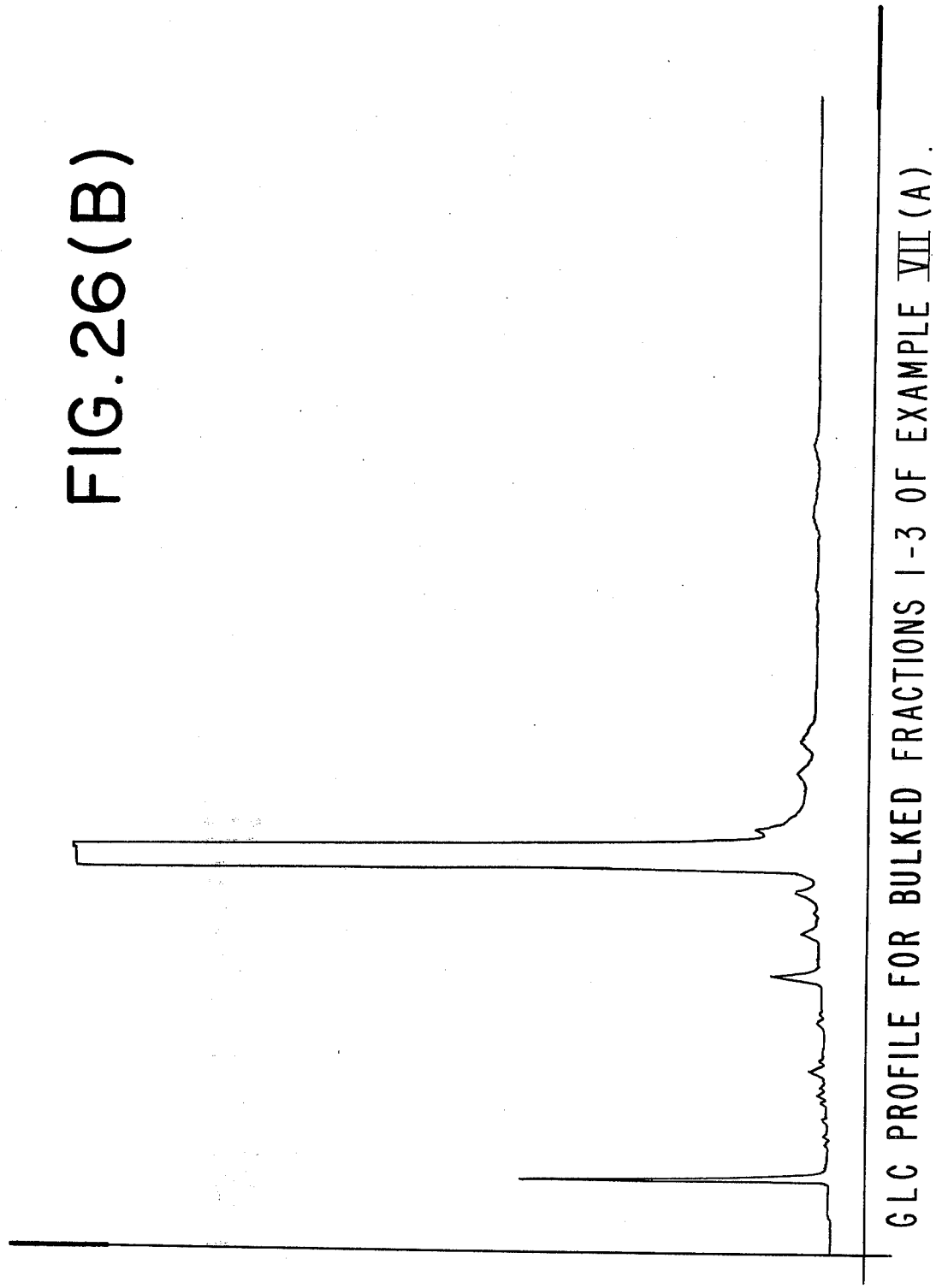
FIG.26(B) GLC PROFILE FOR BULKED FRACTIONS 1-3 OF EXAMPLE VII (A).

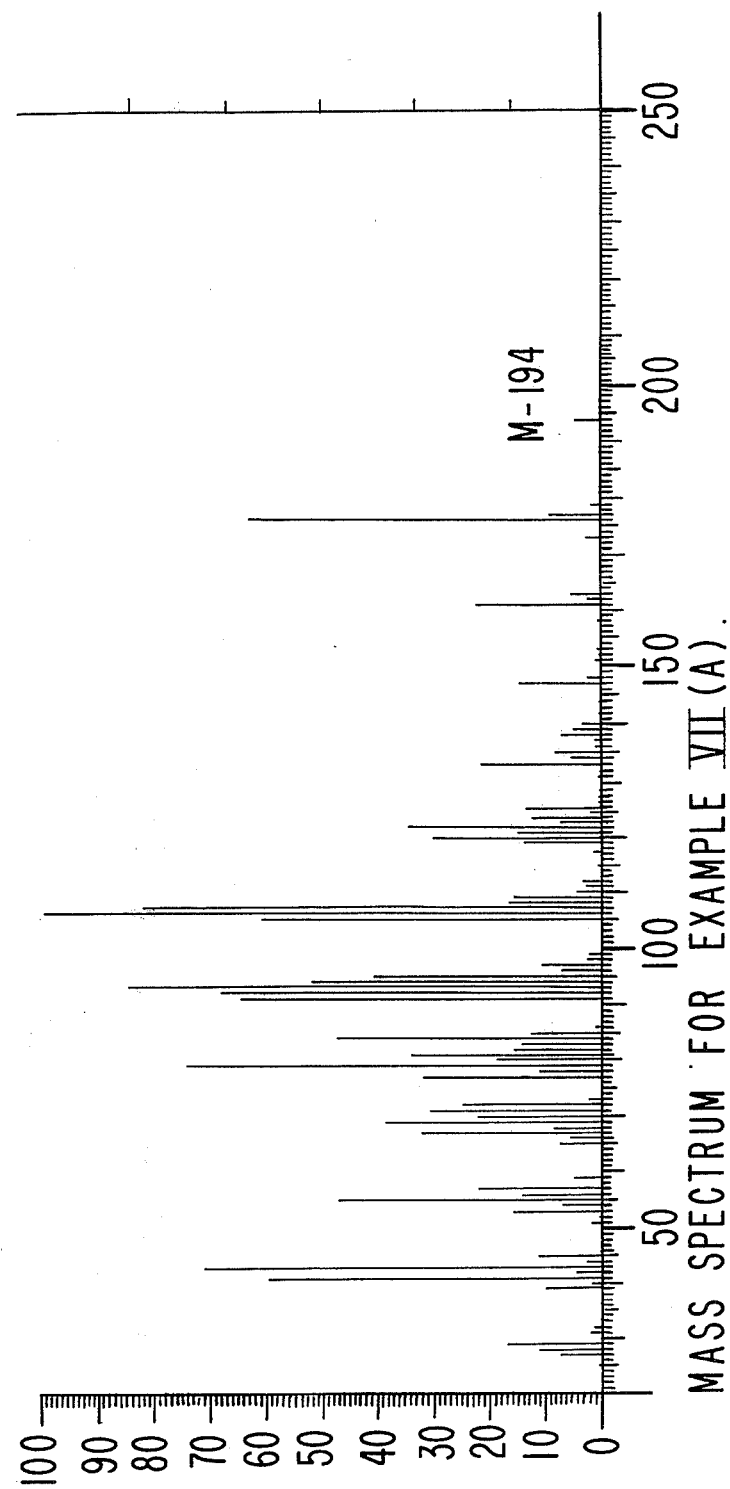
FIG. 27 MASS SPECTRUM FOR EXAMPLE VII (A).

NMR SPECTRUM FOR EXAMPLE VII(A).

GLC PROFILE FOR EXAMPLE VII (B).
REACTION PRODUCT (1.5 HRS).

GLC PROFILE FOR EXAMPLE VII (B).
REACTION PRODUCT SPIKED WITH REACTANT.

GLC PROFILE FOR EXAMPLE VIII.

MASS SPECTRUM FOR EXAMPLE VIII.

FIG. 34. NMR SPECTRUM FOR FRACTION 3 OF EXAMPLE VIII.

IR SPECTRUM FOR FRACTION 3 OF EXAMPLE VIII

GLC PROFILE FOR FRACTION 2, EXAMPLE X.

GLC PROFILE FOR EXAMPLE IX.

MASS SPECTRUM FOR EXAMPLE IX.

FIG. 38 NMR SPECTRUM FOR FRACTION 4 OF EXAMPLE IX.

IR SPECTRUM FOR FRACTION 4 OF EXAMPLE IX.

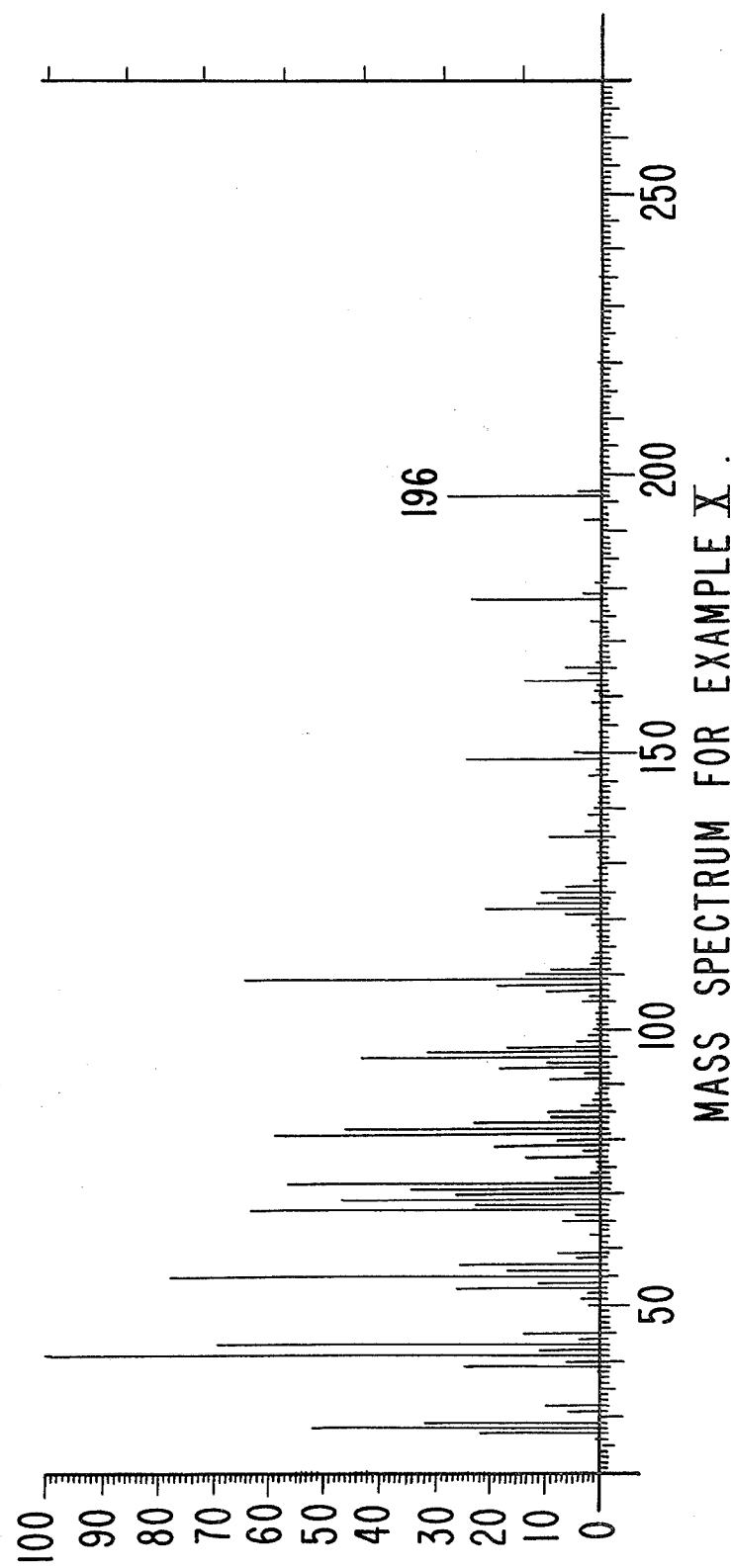
FIG. 41 MASS SPECTRUM FOR EXAMPLE X.

NMR SPECTRUM FOR FRACTION I OF EXAMPLE X.

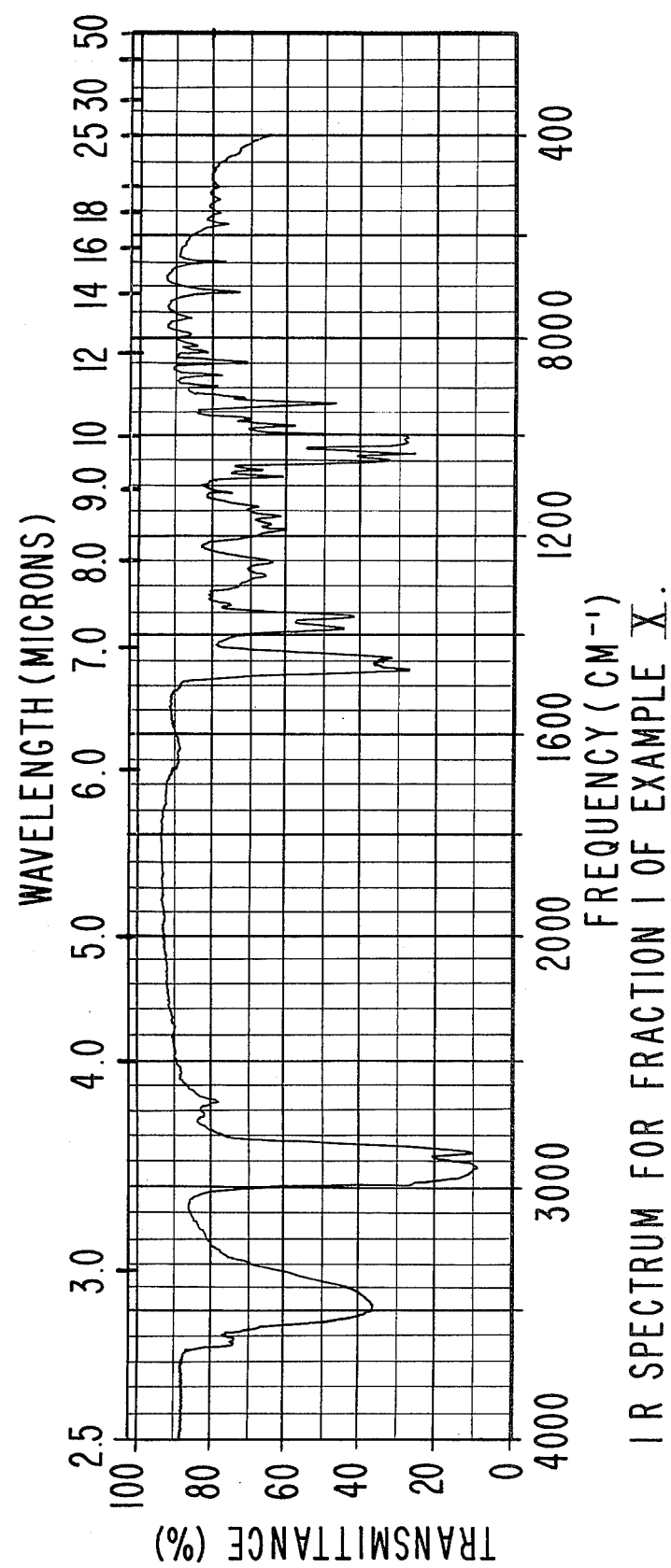

GLC PROFILE FOR EXAMPLE XII. (CRUDE REACTION PRODUCT AFTER WORKUP).

GLC PROFILE FOR FRACTION 3 OF EXAMPLE XI.

FIG. 45 — MASS SPECTRUM FOR EXAMPLE XI.

NMR SPECTRUM FOR FRACTION 4 OF EXAMPLE XI.

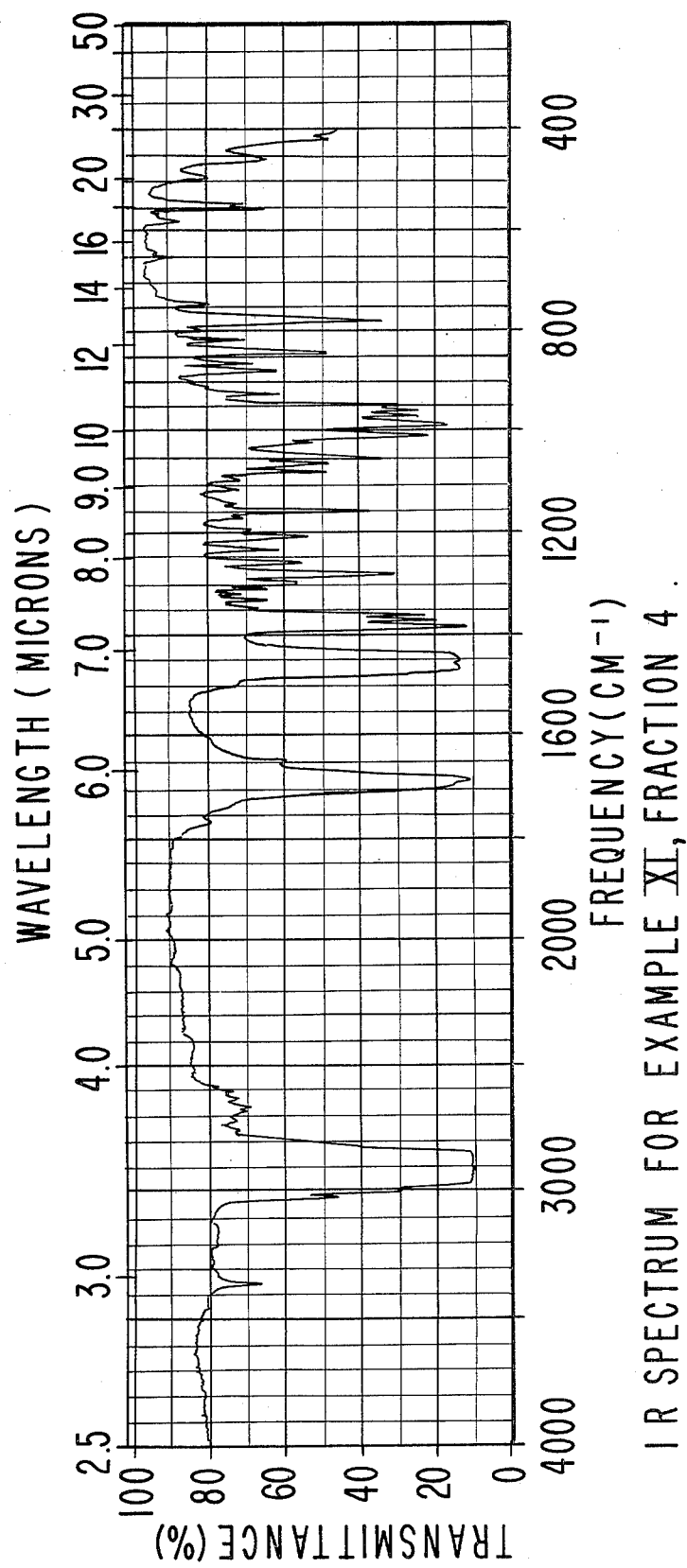

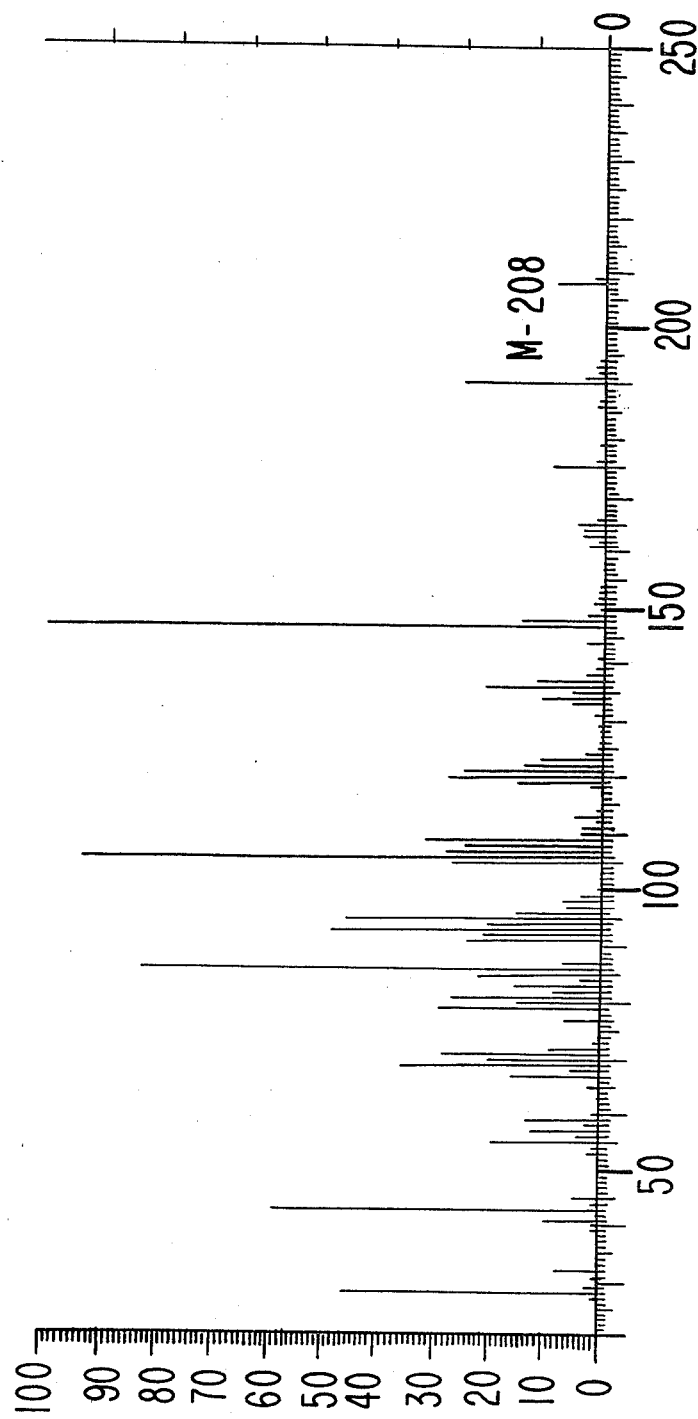
FIG. 49 MASS SPECTRUM FOR EXAMPLE XII.

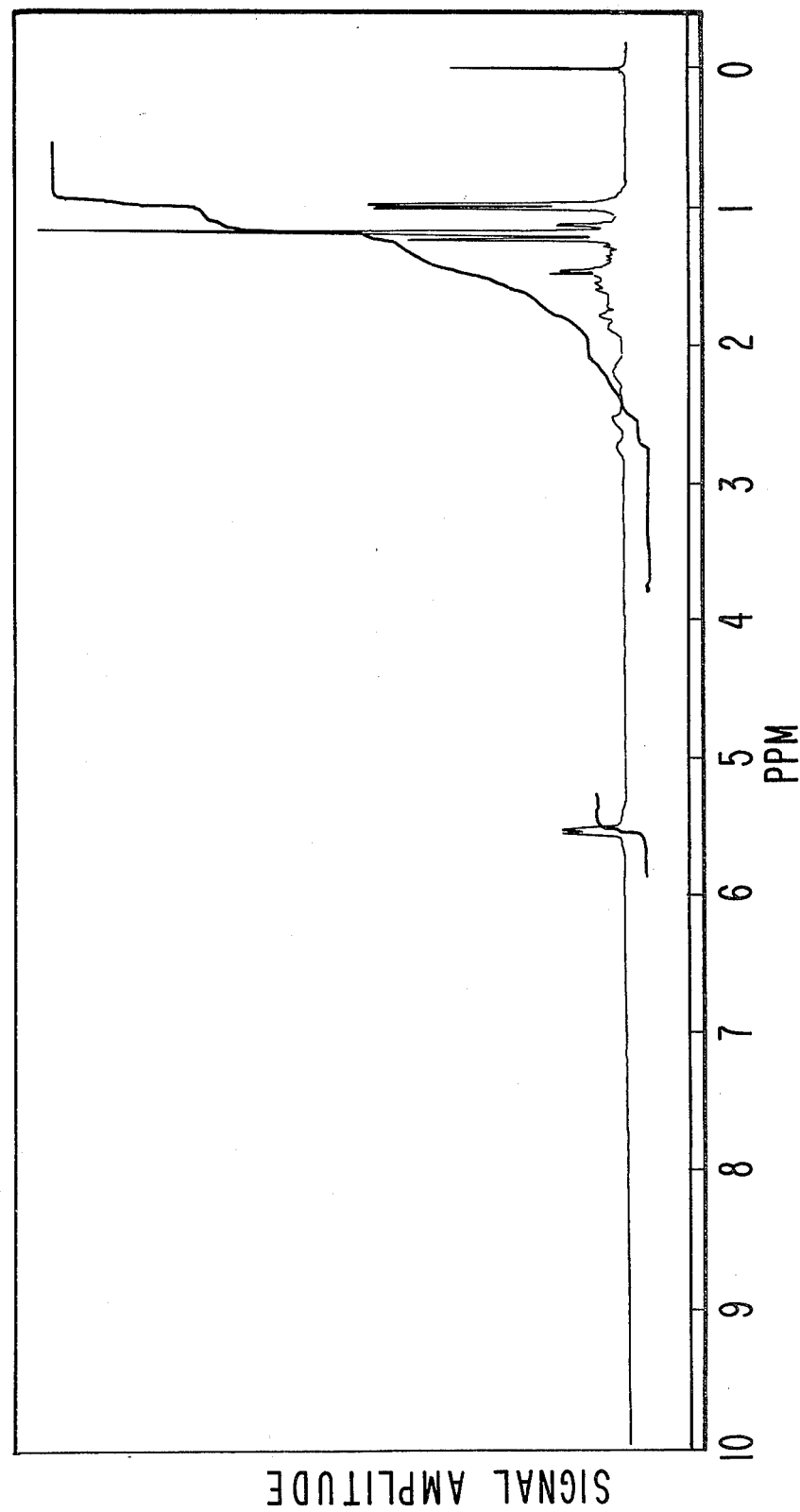
FIG. 50 NMR SPECTRUM FOR FRACTION 6 OF EXAMPLE XII.

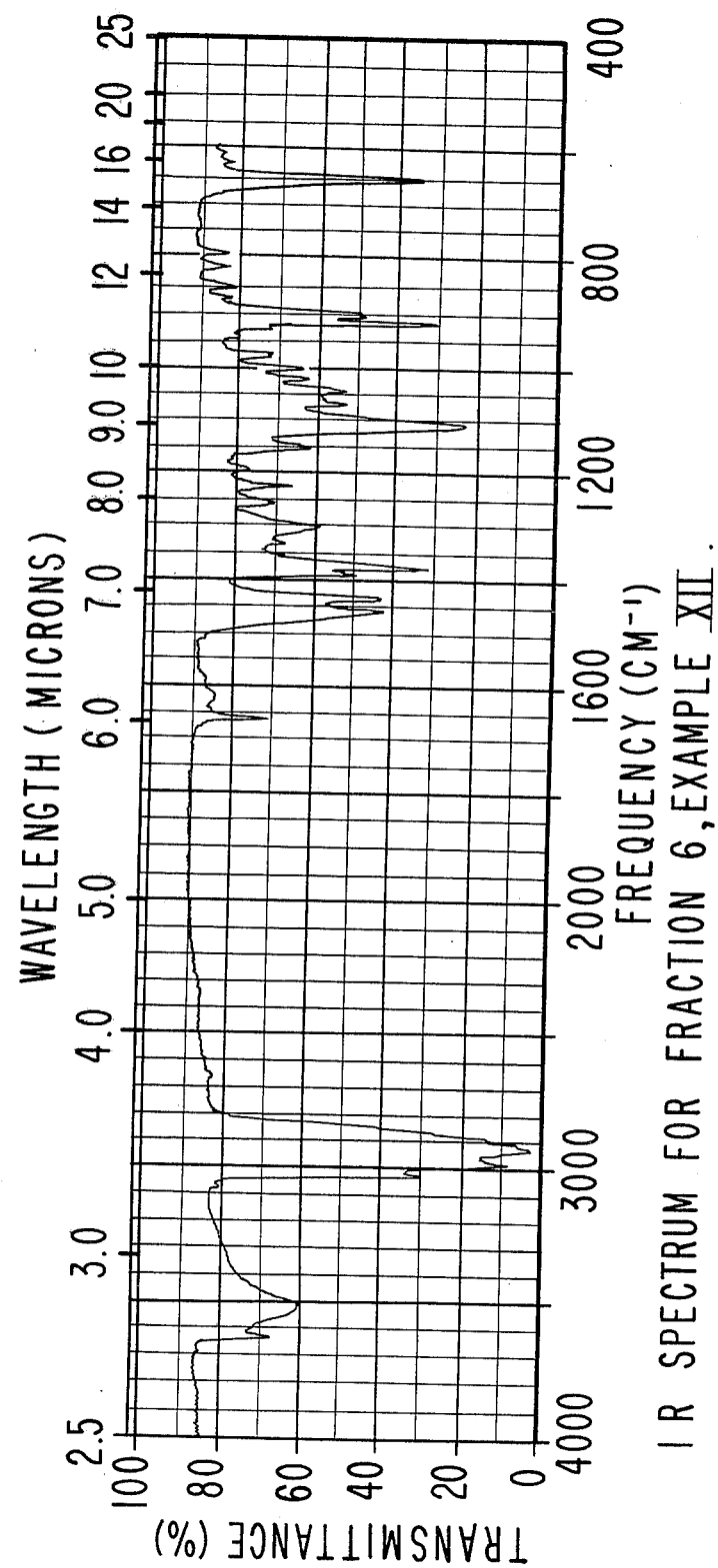

GLC PROFILE FOR EXAMPLE XIII.
(FRACTION 2 OF RUSHOVER DISTILLATION).

FIG. 53 MASS SPECTRUM FOR EXAMPLE XIII.

FIG. 54 NMR SPECTRUM FOR FRACTION 6 OF EXAMPLE XIII.

GLC PROFILE FOR FRACTION 3 OF EXAMPLE XIV.

FIG. 58 NMR SPECTRUM FOR FRACTION 4 OF EXAMPLE XIV.

IR SPECTRUM FOR FRACTION 4 FOR EXAMPLE XIV.

FIG. 60 GLC PROFILE FOR EXAMPLE XV.

MASS SPECTRUM FOR EXAMPLE XV.

FIG. 62 NMR SPECTRUM FOR EXAMPLE XV.

IR SPECTRUM FOR EXAMPLE XV.

GLC PROFILE FOR EXAMPLE XVI (AFTER 8 HOURS REFLUX).

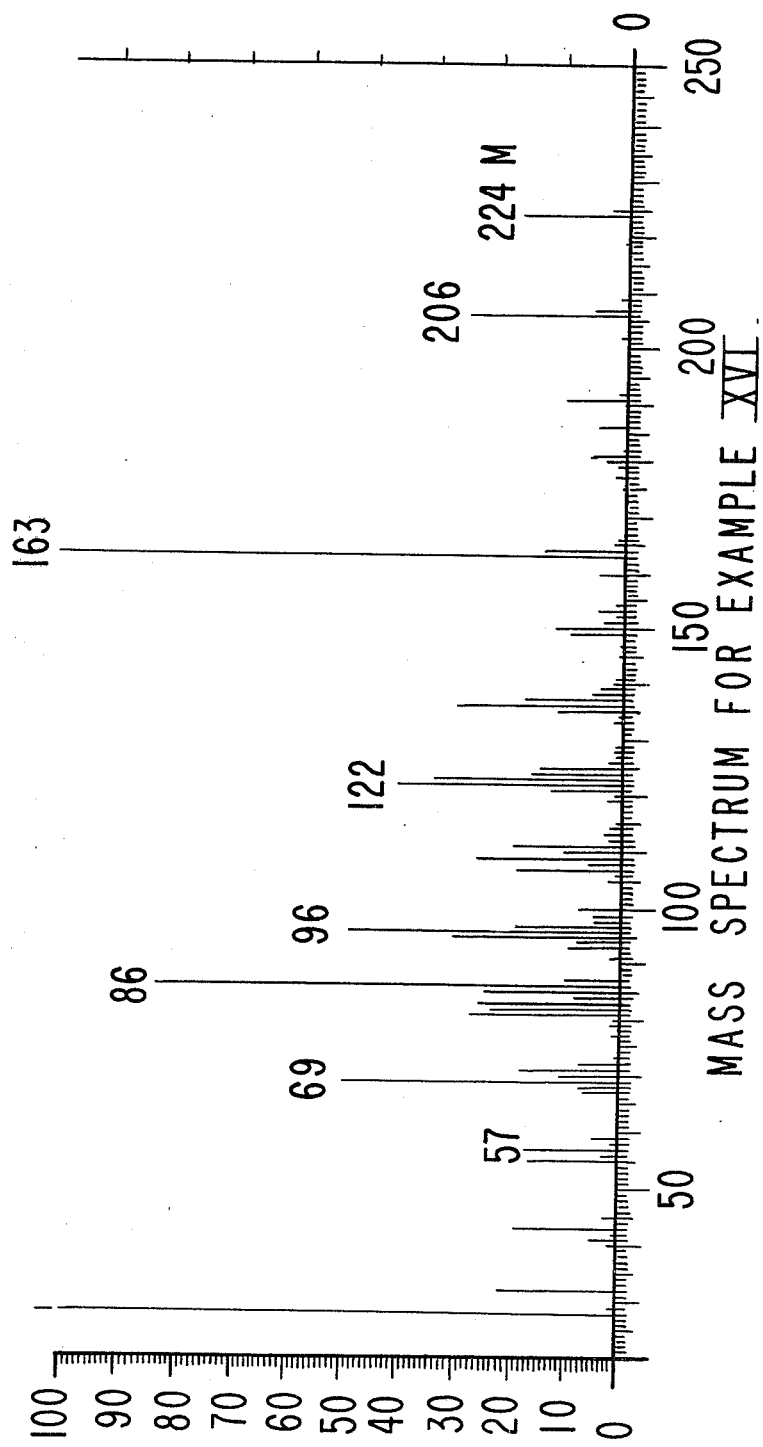
FIG. 65 MASS SPECTRUM FOR EXAMPLE XVI

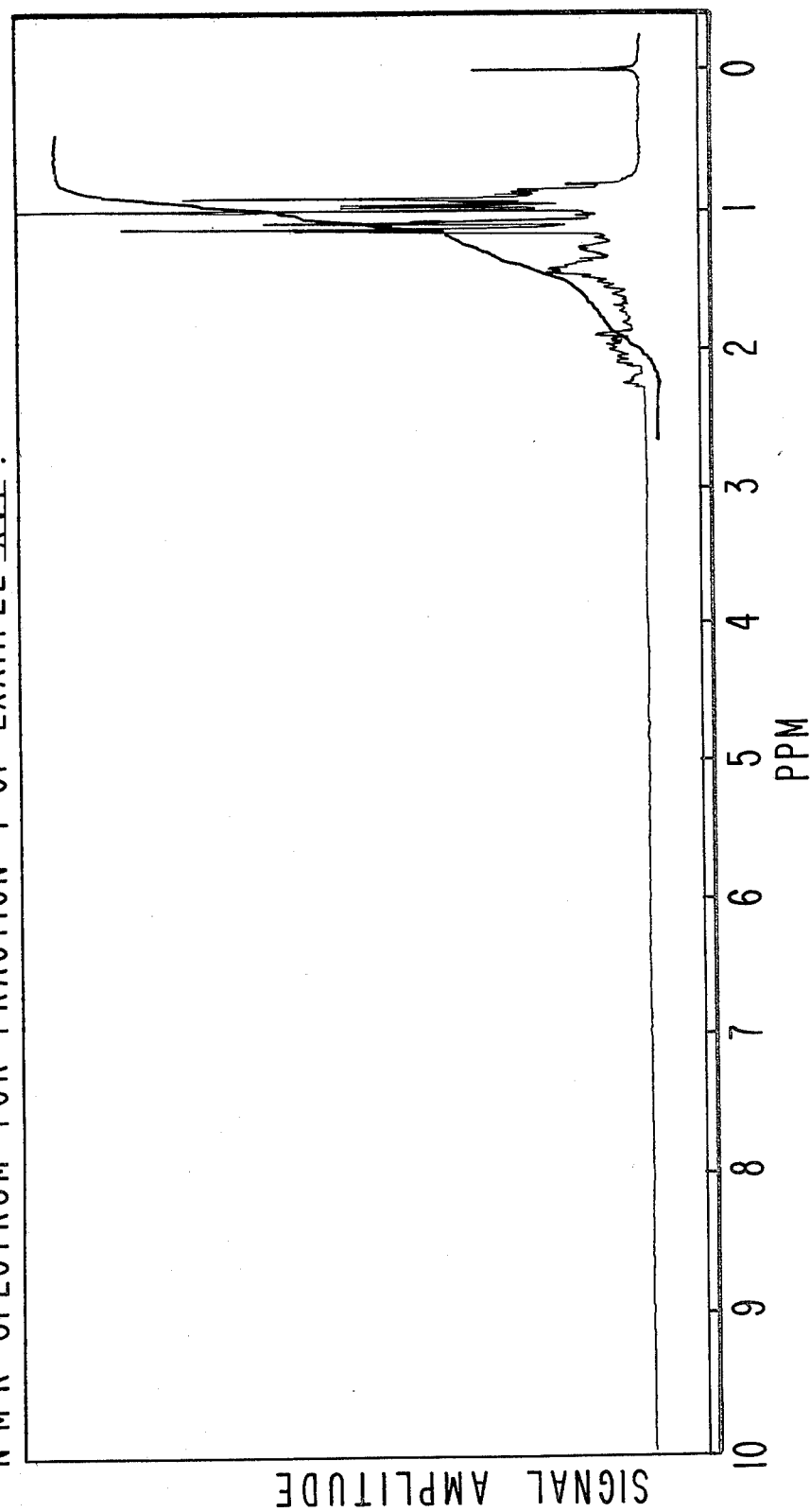
FIG. 66 NMR SPECTRUM FOR FRACTION 4 OF EXAMPLE XVI.

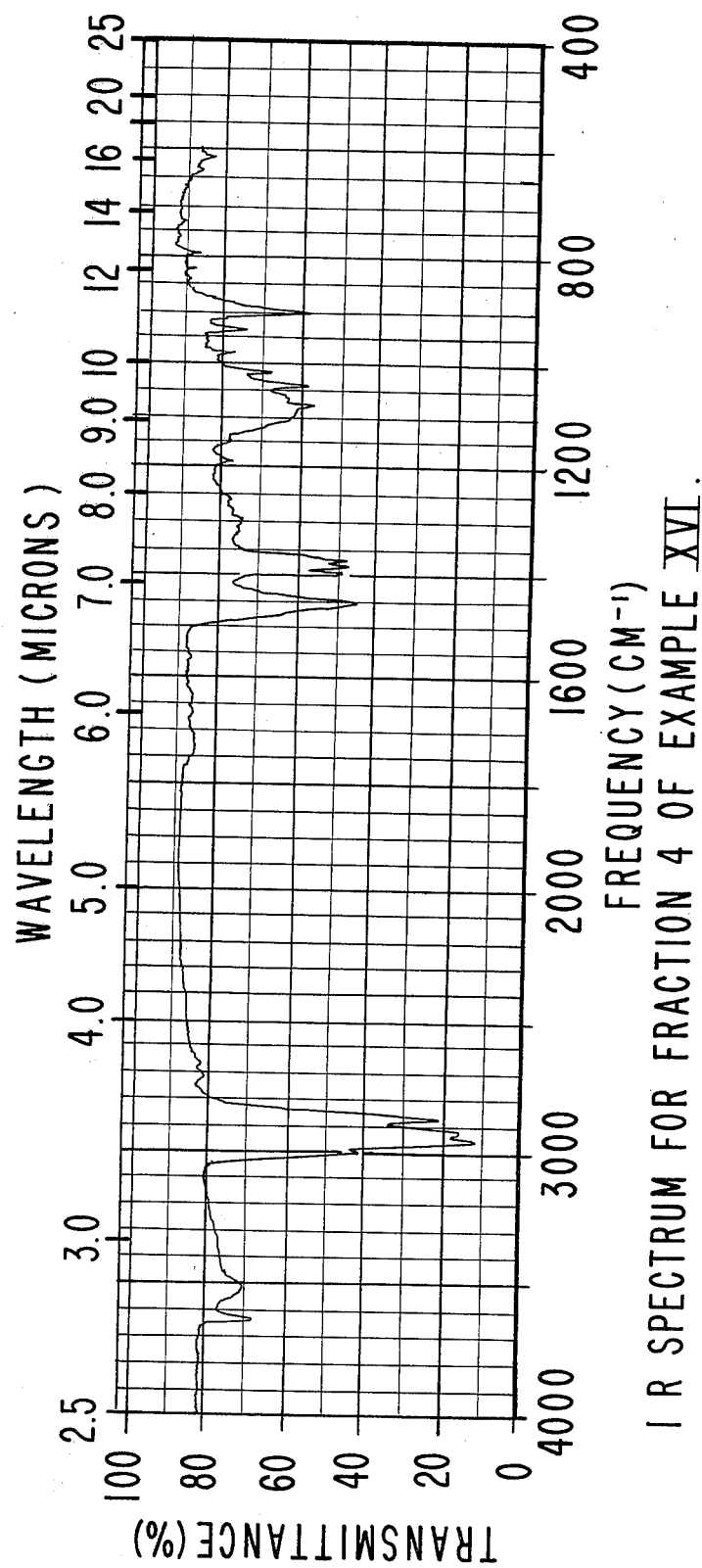

METHYL SUBSTITUTED OXOBICYCLO-4,4,0-DECANE DERIVATIVES, PROCESS FOR PREPARING SAME AND ORGANOLEPTIC USES THEREOF

BACKGROUND OF THE INVENTION

The instant invention covers compounds having the generic structure:

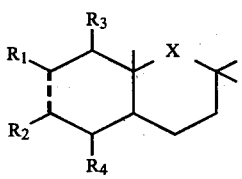

wherein the dashed line represents a carbon-carbon single bond or a carbon-carbon double bond; wherein X represents the moieties:

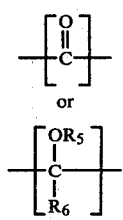

wherein $R_1$, $R_2$, $R_3$ and $R_4$ represent hydrogen or methyl with the provisos that (i) at least three of $R_1$, $R_2$, $R_3$ and $R_4$ represent hydrogen and (ii) when the dashed line is a carbon-carbon single bond and x is:

then one of $R_1$, $R_2$, $R_3$ or $R_4$ is methyl and the other represents hydrogen; wherein $R_5$ represents hydrogen, MgX, MgR$_7$, CdR$_7$, ZnR$_7$, Na, K or Li; wherein X represents Chloro, Bromo or Iodo; wherein $R_6$ represents hydrogen or methyl; and wherein $R_7$ represents lower alkyl; as well as uses of the above compounds, with the exception of the organometallic compounds of the genus, for augmenting or enhancing the aromas and/or taste of consumable materials.

Materials which can provide minty, camphoraceous, dry woody, sweet, fruity, woody patchouli, green, herbaceous, basil-like, citrus-like, bergamot-like, lime-like, grapefruit-like, peppery, precious-woody, vertiver-like, fresh, musky, lavender thyme, rosemary, sweaty, rooty and earthy aromas with floral, citrus, lavender and amber top-notes and backgrounds are known in the art of perfumery. Many of the natural materials which provide such fragrances and contribute desired nuances to perfumery compositions are high in cost, vary in quality from one batch to another and/or are generally subject to the ususal variations of natural products.

By the same token, materials which can provide oriental, insence-like, peppery, blueberry-like, eucalyptol-like, minty, camphoraceous, floral, musk-like, rose-like, black pepper, spicey, patchouli, cooling, sandalwood-like, woody and walnut-like aromas with oriental, black pepper, peppery, minty, eucalyptol-like, camphoraceous, floral, rosey and patchouli-like tastes are well known in the art of flavoring for foodstuffs, toothpastes, chewing gums and medicinal products. Many of the natural materials which provide such flavor nuances and contribute desired nuances to flavor and compositions are high in cost, vary in quality from one batch to another and/or are generally subject to the usual variations of natural products.

Sweet, fruity, berry-like, cooling, woody and floral aroma and taste nuances are known in the art of the production of smoking tobaccos and smoking tobacco articles. Many of the natural materials which provide such aroma and taste nuances to smoking tobacco compositions are high in cost, vary in quality from one batch to another and/or are generally subject to the usual variations of natural products.

There is, accordingly, a continuing effort to find synthetic materials which will replace, enhance or augment the essential flavor and/or fragrance notes provided by natural essential oils or compositions thereof. Unfortunately, many of these synthetic materials either have the desired nuances only to a relatively small degree or else contribute undesirable or unwanted odor to the consumable compositions. The search for materials which can provide more refined patchouli-like aromas, for example, have been difficult and relatively costly in the areas of both natural products and synthetic products.

Artificial flavoring agents for foodstuffs have received increasing attention in recent years. For many years such food flavoring agents have been preferred over natural flavoring agents at least in part due to their diminished cost and their reproducible flavor qualities. For example, natural food flavoring agents such as extracts, concentrates and the like are often subject to wide variations due to changes in quality, type and treatment of the raw materials. Such variations can be reflected in the end products and result in unfavorable flavor characteristics in said end product. Additionally, the presence of the natural product in the ultimate food may be undesirable because of increased tendency to spoil. This is particularly troublesome in food and food uses where such products as dips, soups, chips, sausages, gravies and the like are apt to be stored prior to use.

The fundamental problem in creating artificial flavor agents is that the artificial flavor to be achieved be as natural as possible. This generally proves to be a difficult task since the mechanism for flavor development in many foods, medicinal products, chewing gums and toothpastes is not completely known. This is noticable in products having licorice, citrusy and vegetable flavor characteristics particularly.

Even more desirable are products that can serve to substitute for difficult-to-obtain natural perfumery oils and at the same time substitute for natural flavoring ingredients in foodstuffs, chewing gums, medicinal products, toothpastes, and smoking tobaccos.

Oxobicyclo compounds are known in the prior art. Thus, Nagakura, et al., Bull. Chem. Soc. Japan Vol. 48(10), 2995-6 (October 1975) discloses the compound defined according to the generic structure:

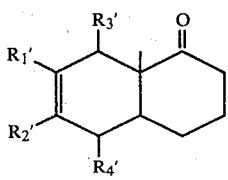

produced by the reaction:

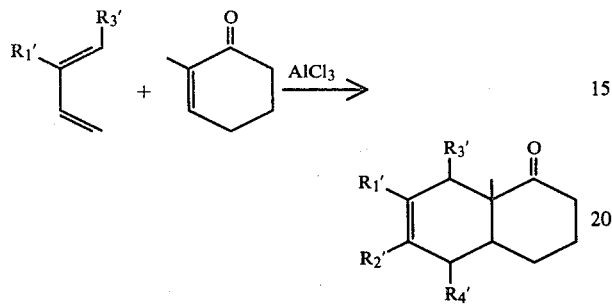

wherein one of $R_1'$, $R_2'$, $R_3'$ or $R_4'$ is methyl and the others represent hydrogen. In addition, Conia and Rouessac, Bull. Soc. Chem. France 1953(page 1925 et seq.) discloses processes for producing oxobicyclo compounds according to the following reaction steps:

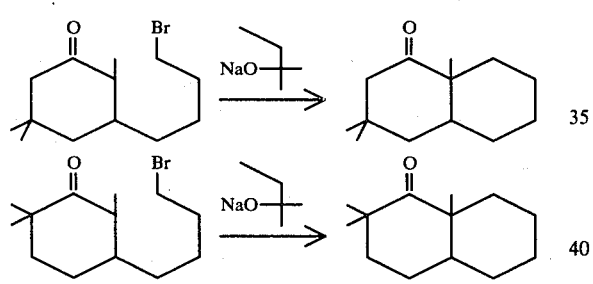

The use of oxotricyclic derivatives in perfumery is disclosed in U.S. Pat. No. 3,996,169, issued on Dec. 7, 1976. Thus, in U.S. Pat. No. 3,996,169, a genus defined according to the structure:

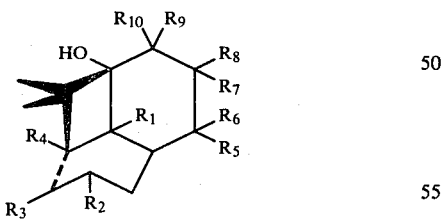

is disclosed, wherein $R_1$, $R_2$, $R_3$, $R_4$, $R_5$, $R_6$, $R_7$, $R_8$, $R_9$ and $R_{10}$ is selected from the group consisting of hydrogen and methyl; and wherein the dashed line may be a carbon-carbon single bond or a carbon-carbon double bond. Members of this genus are indicated to be capable of altering, modifying, enhancing or emparting an aroma of or to consumable materials including colognes, perfumes and perfumed articles and such an aroma is of a patchouli type.

Arctander, "Perfume and Flavor Chemicals", 1969, Vol. 1 discloses the use in perfume compositions and foodstuff flavors of "decalinol", "decalone", "fenchone", and "fenchyl alcohol", thusly:

"(i) 1385: FENCHONE laevo-Fenchone. (dextro- is known but less common as a fragrance material).
1,3,3-Trimethyl-2-norbornanone.
1,3,3-Trimethyl bicyclo-1,2,2-heptone-2.

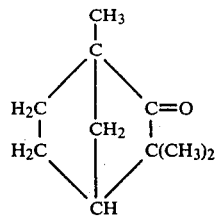

Warm-camphoraceous, powerful and diffusive, basically sweet odor.
Warm, somewhat burning and bitter taste with a medicinal note.
This ketone finds some use as a masking odor in industrial fragrances. It is also used in the reconstruction of Fennel oil and a few other essential oils.
In spite of its rather unpleasant taste, it is used in various Berry complex flavors, in Spice complexes and in certain types of Liquer flavoring.
The concentration used is about 0.1 to 5 ppm in the finished product.
(ii) 1387: FENCHYL ALCOHOL
1,3,3-Trimethyl-2-norbornanol.
1,3,3-Trimethyl bicyclo-1,2,2-heptanol-2.
2-Fenchanol.
Fenchol.

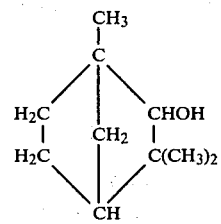

The racemic alpha-Fenchol has a somewhat lower melting point, and the beta-Fenchols are all liquid at room temperature.
Fenchol made by reduction of Fenchone from Cedar-leaf oil is usually a mixture of several isomers, including the crystalline alpha-isomers. The beta-isomer forms a crystalline Hydrate which may be solid at room temperature.
Almost insoluble in water, soluble in alcohol, miscible with oils. Powerful and diffusive, Camphor-like, but sweeter and more Citrus-like almost Lime-like odor with more or less of an earthy-dry character, according to the composition and isomer-ratio.
The taste is somewhat bitter-Lime-like, camphoraceous and slightly woody-musty.
This interesting alcohol (or mixed alcohols) finds use in perfume compositions ranging from woody or herbaceous to Citrus-Lime and even certain floral types. It produces power and 'lift' to floral fragrances, and solid background to Lime and other Citrus bases, having the advantage over the Terpenes in being very stable in soap.

Fenchyl alcohol is also used in flavor compositions such as Strawberry and other berries, Lime and Spice, etc.

The concentration is normally low, e.g. 0.2 up to 5 ppm in the finished product.

(iii) 824: TRANS-DECAHYDRO-BETA-NAPHTHOL trans-beta-Decanol.

(sometimes called "Decalinol".)

Bicyclo-4,4,0-Decanol

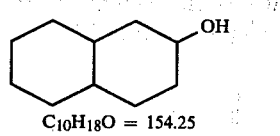

$C_{10}H_{18}O = 154.25$

Colorless viscous liquid, solidifying in the cold to an opaque mass. The presence of variable amounts of the cis-isomer is mainly responsible for the variations in physical appearance of this material.

Mild, sweet, slightly camphoraceous-woody, also warm and mildly spicy odor of fair tenacity. The odor has been compared to that of Dihydrocarveol, but such description does not help many perfumers.

Practically insoluble in water, soluble in alcohol and oils.

This alcohol has been used, and is still used on a mosdest scale, in perfume compositions, mostly in connection with woody and camphoraceous fragrance types, including the Ionones, Cyclohexyl-derivatives, etc. Several of its esters (see following monographs) have been more successful as perfume materials).

However, since the Ambregis- and Sandalwood-notes, which are represented to a certain degree in the esters, can be obtained with much superior beauty by way of modern perfume chemicals, there is reason to believe that the Decahydronaphthyl series will eventually become obsolete.

Prod.: by catalytic hydrogenation of beta-Naphthol. The reaction yields a mixture of cis- and trans-isomers, but the perfumers generally prefer the trans-isomer or a material primarily consisting of that isomer.

(iv) 830: BETA-DECALONE

Decahydro naphthalone

The commercial products consist of a mixture of cis- and trans-isomers.

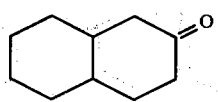

$C_{10}H_{16}O = 152.24$

Viscous colorless liquid, solidifying in the cold.

Practically insoluble in water, soluble in alcohol and oils.

The cis-isomer is liquid and boils at 247° C.

The trans-isomer is solid below 6° C. and boils at 241° C.

Semi-dry, tenacious odor resembling part of the Ambregris-picture, also woody, remotely reminiscent of Sandalwood. Odor variations are observed in materials from different sources of supply.

This ketone has found a little use in perfume compositions, including soap perfumes, where it can introduce pleasant background notes in support of Musk Ambrette, Labdanum, Methylionones, etc.

Recent development in Ambregris chemicals has brought much superior materials in the hands of the perfumer, and it is very likely that the title material, and many of its relatives, will become obsolete within the next decade or so.

Prod.: by oxidation of beta-Decalol with Chromic acid mixture."

U.S. Pat. No. 3,932,515 discloses the use of the compound having the structure:

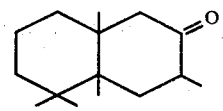

in perfumery and specifically indicates that such compound has a woody aroma of high tenacity. U.S. Pat. No. 3,932,516 discloses the compound having the structure:

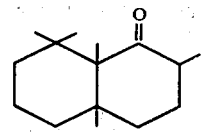

and indicates that this compound is useful in perfumery due to its woody character.

None of the references cited above, or for that matter any other references discloses compounds which have a close structural relationship to the genus of compounds of the instant invention. In any event, the organoleptic properties of the compounds of the references are different in kind from those of the compounds of the instant invention.

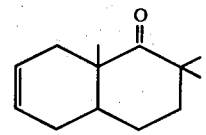

Figure 2:
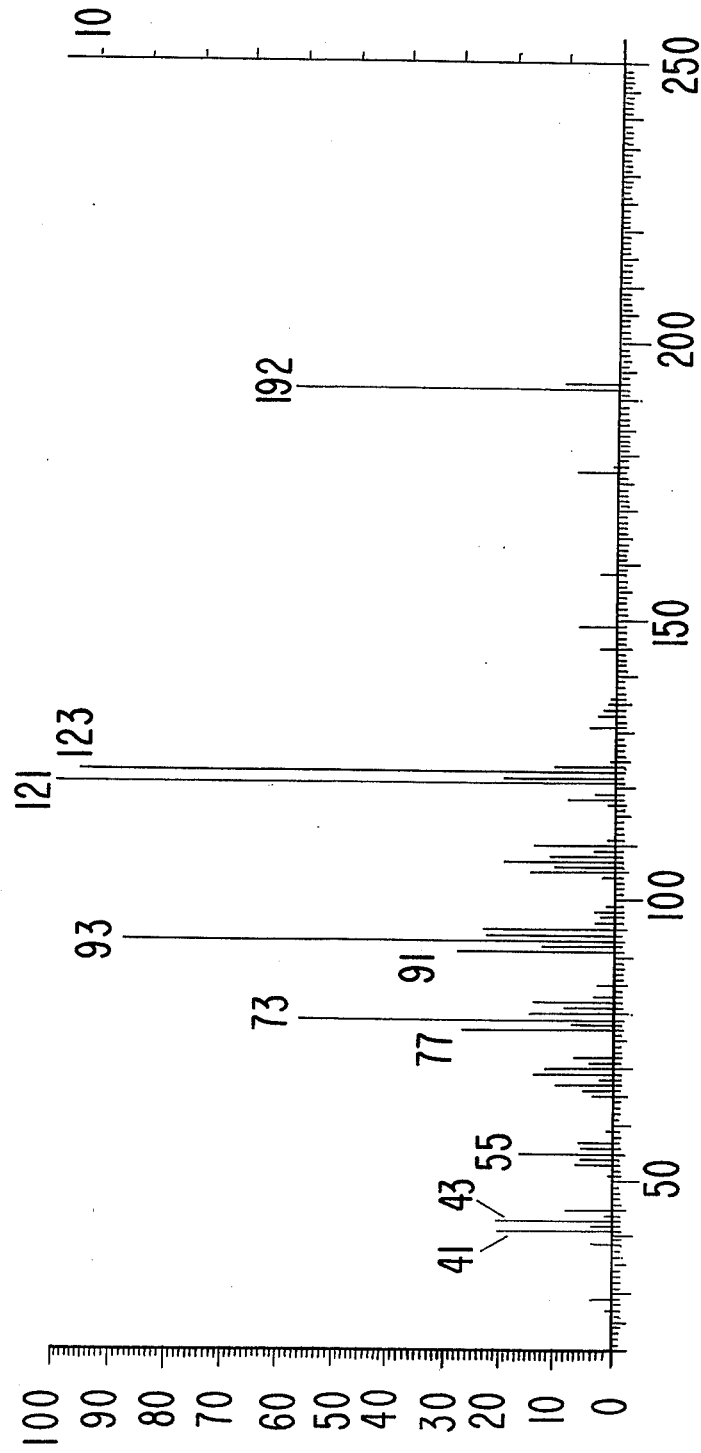

FIG. 2 is the mass spectrum for the product of Example I having the structure:

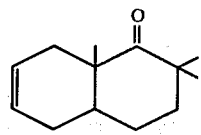

Figure 3:
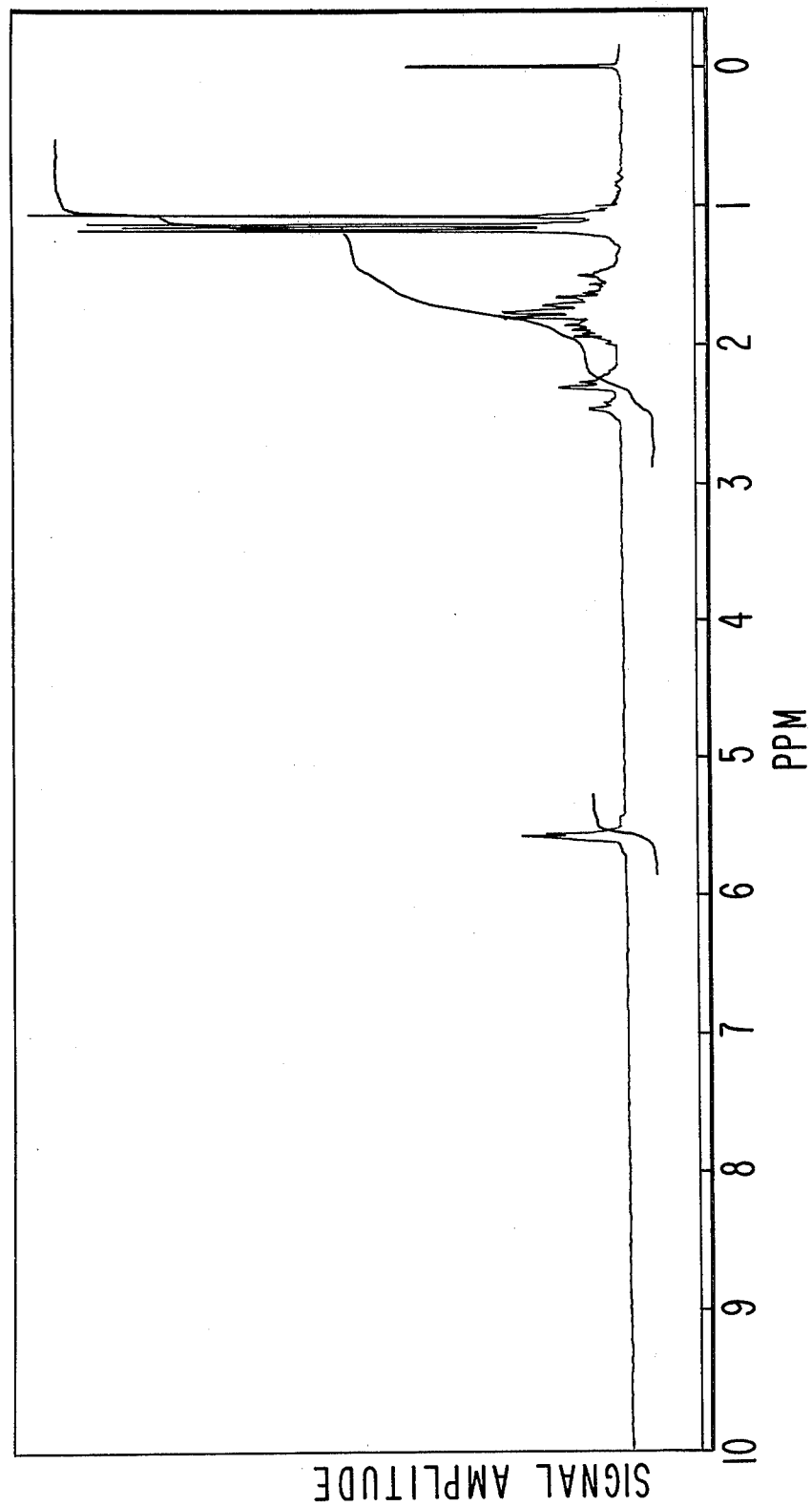

FIG. 3 represents the NMR spectrum for the product of Example I having the structure:

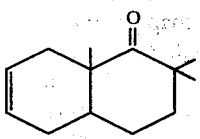

Figure 4:
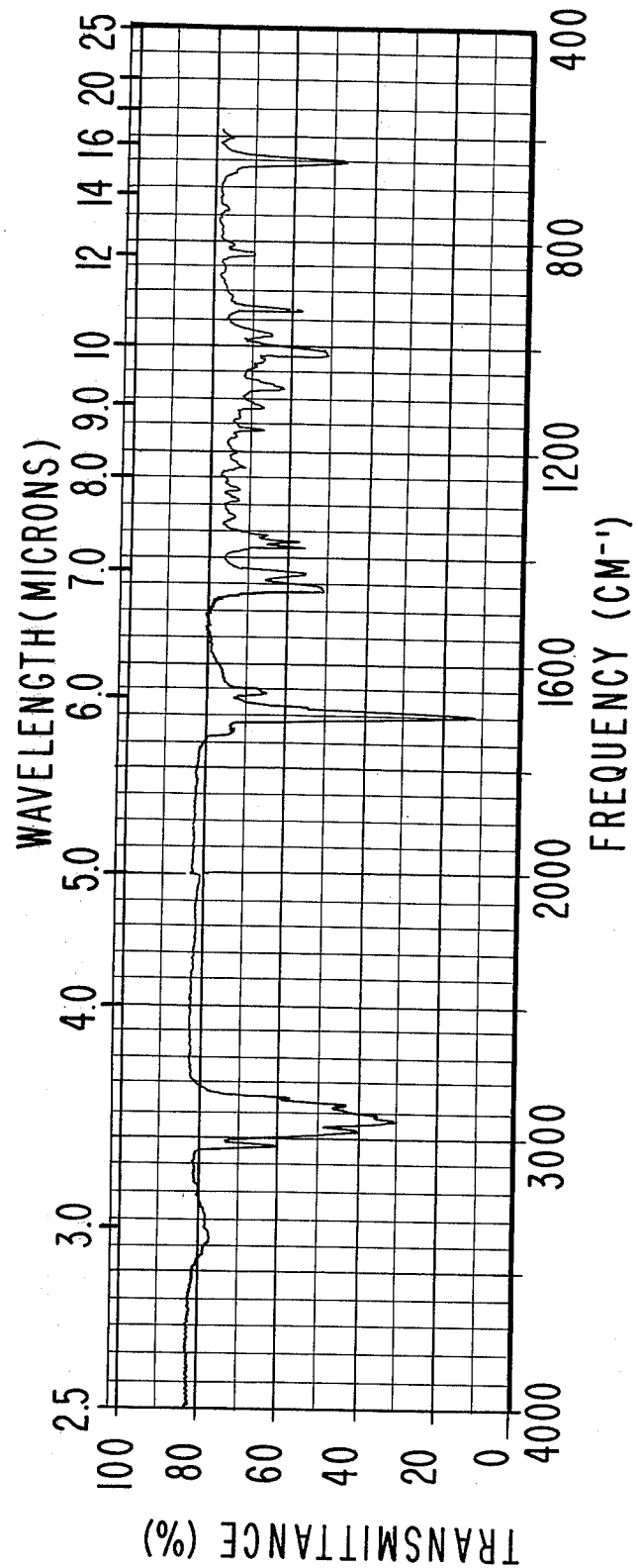

FIG. 4 represents the infrared spectrum for the product of Example I having the structure:

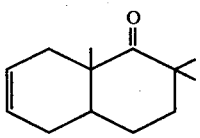

Figure 5:
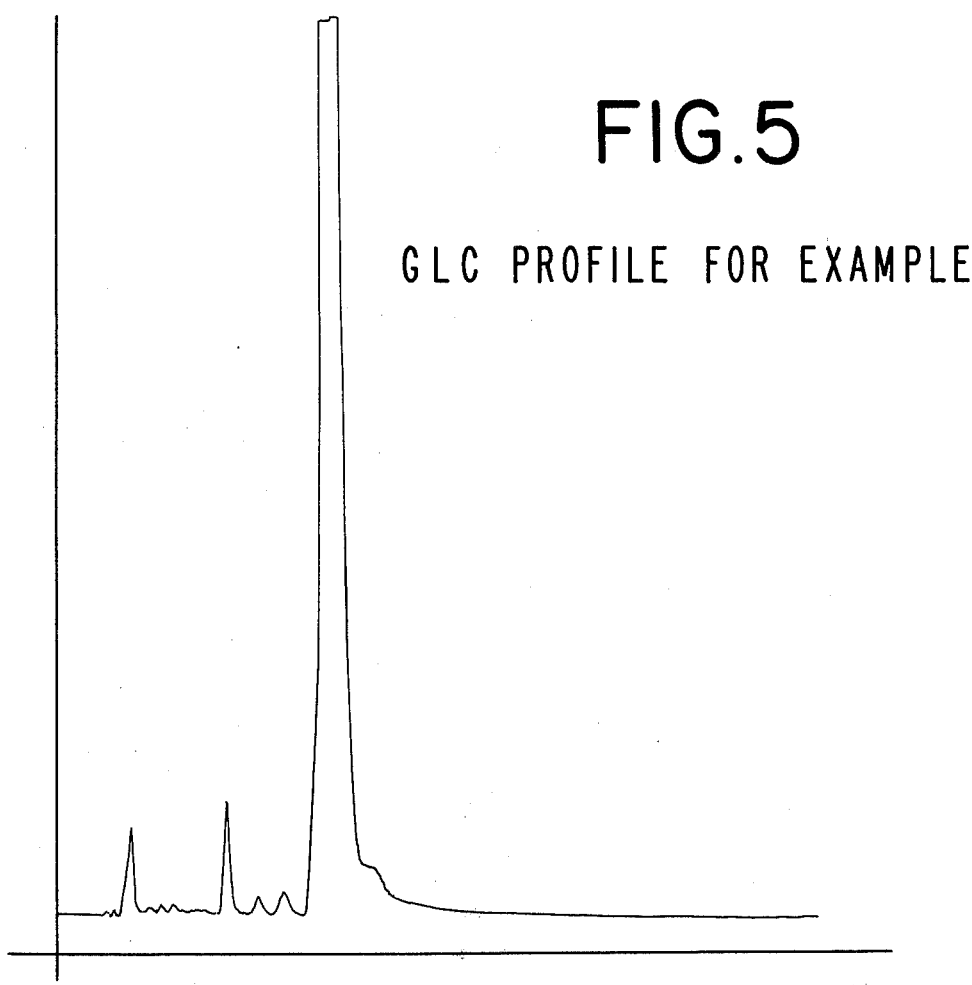

FIG. 5 is the GLC profile for the reaction product of Example II containing the compound having the structure:

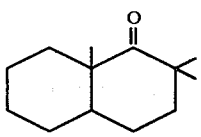

Figure 6:
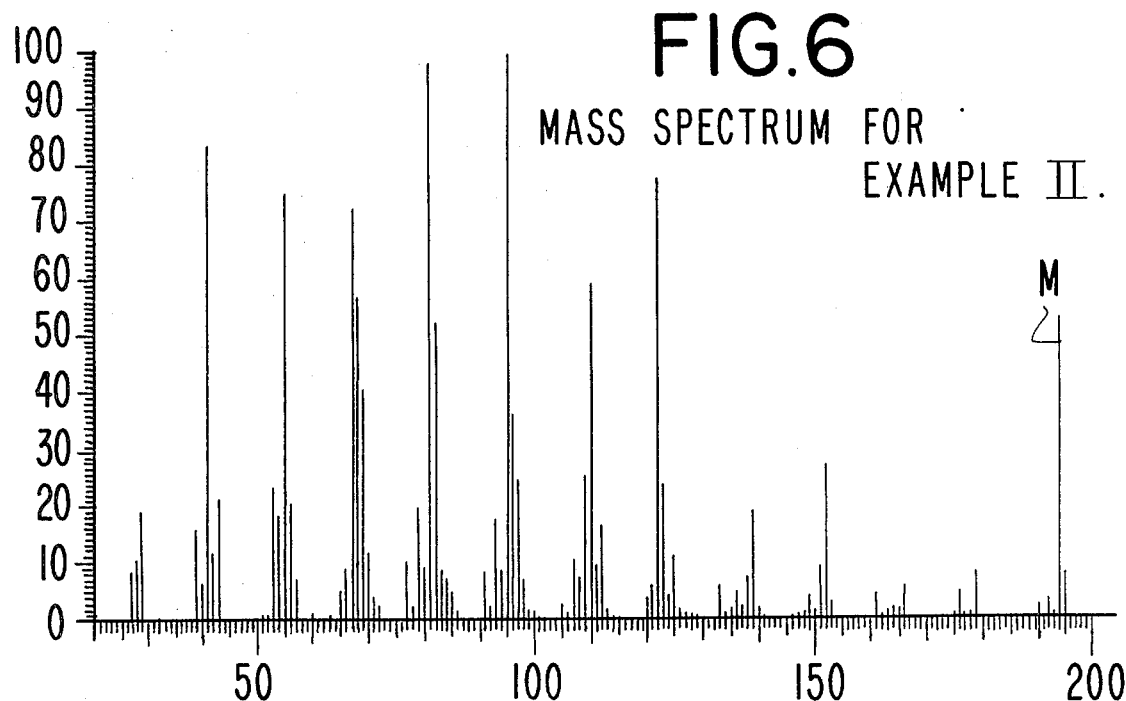

FIG. 6 is the mass spectrum for the product of Example II having the structure:

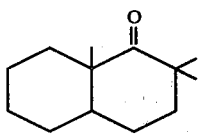

Figure 7:
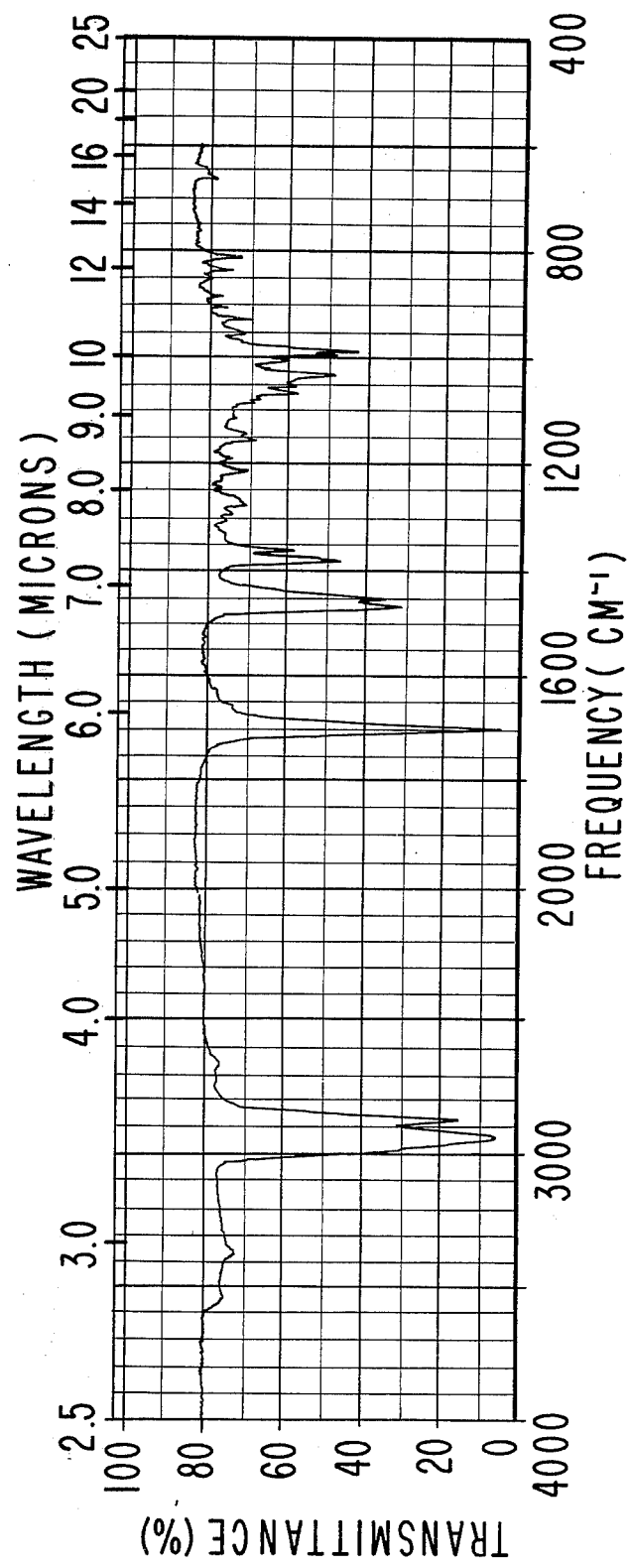

FIG. 7 is the NMR spectrum for the product of Example II having the structure:

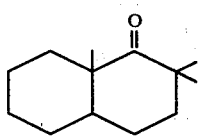

FIG. 8 is the infrared spectrum for the product of Example II having the structure:

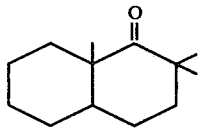

Figure 9A:
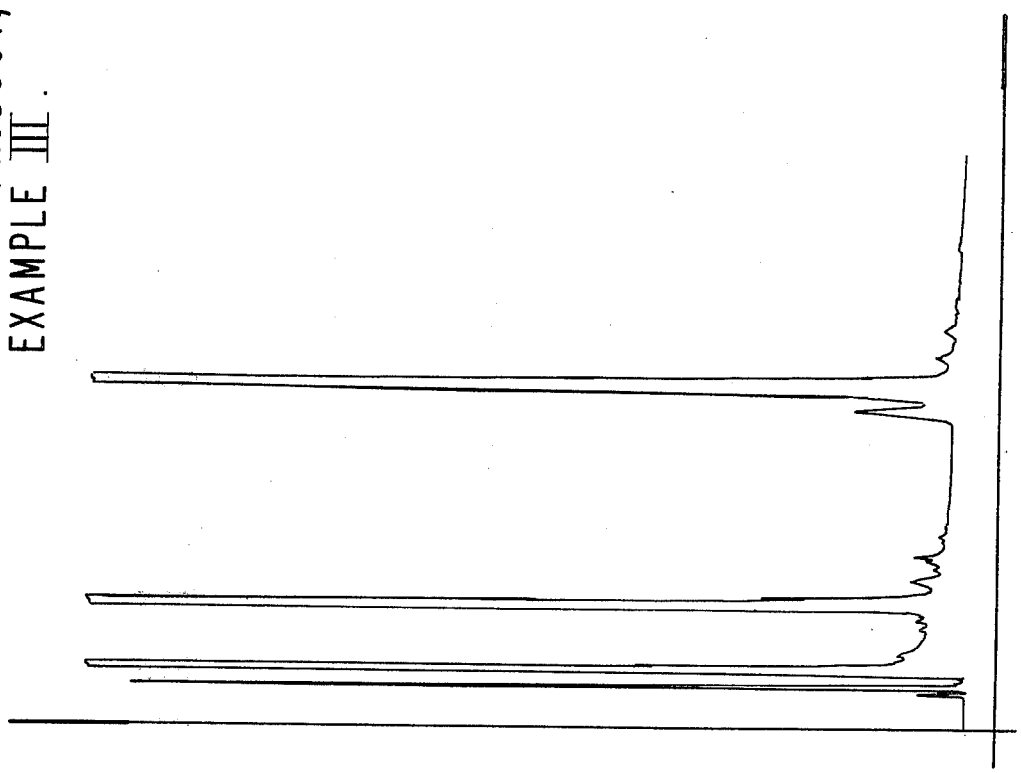

FIG. 9A represents the GLC profile for the major product of Example III.

Figure 9:
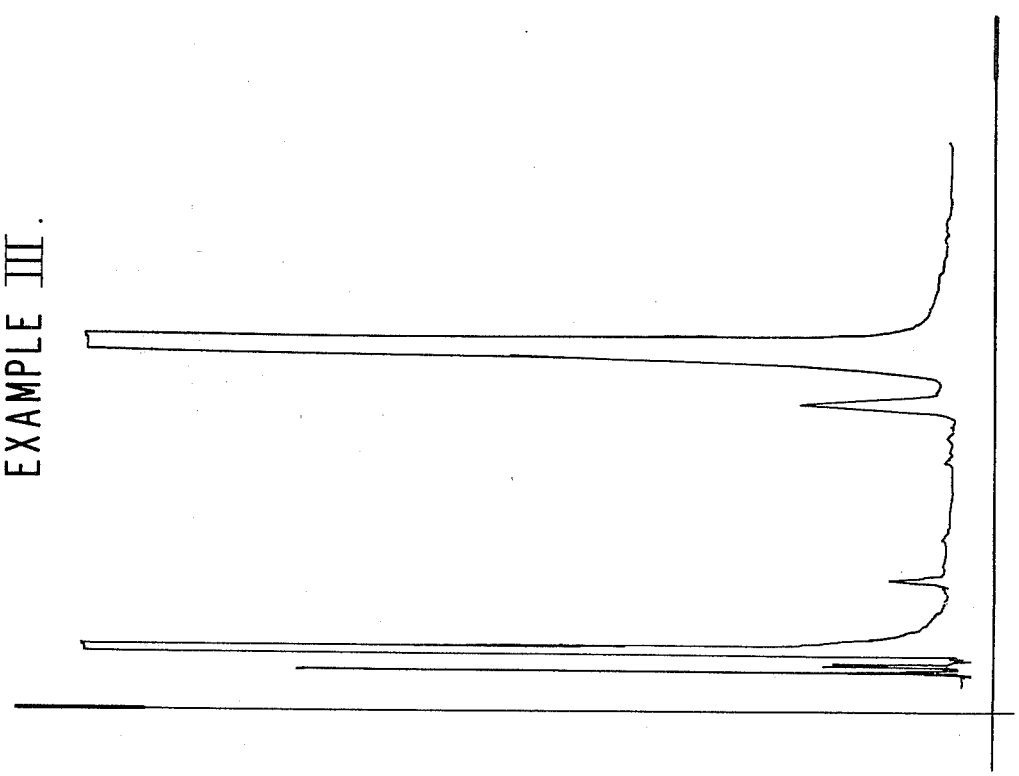

FIG. 9 is the GLC profile for the reaction product of Example III containing the compounds having the structures:

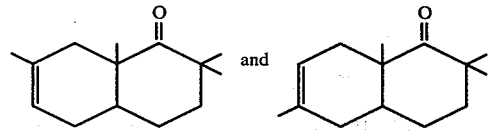

(fraction 2 of one-plate distillation, "Rushover")

Figure 10:
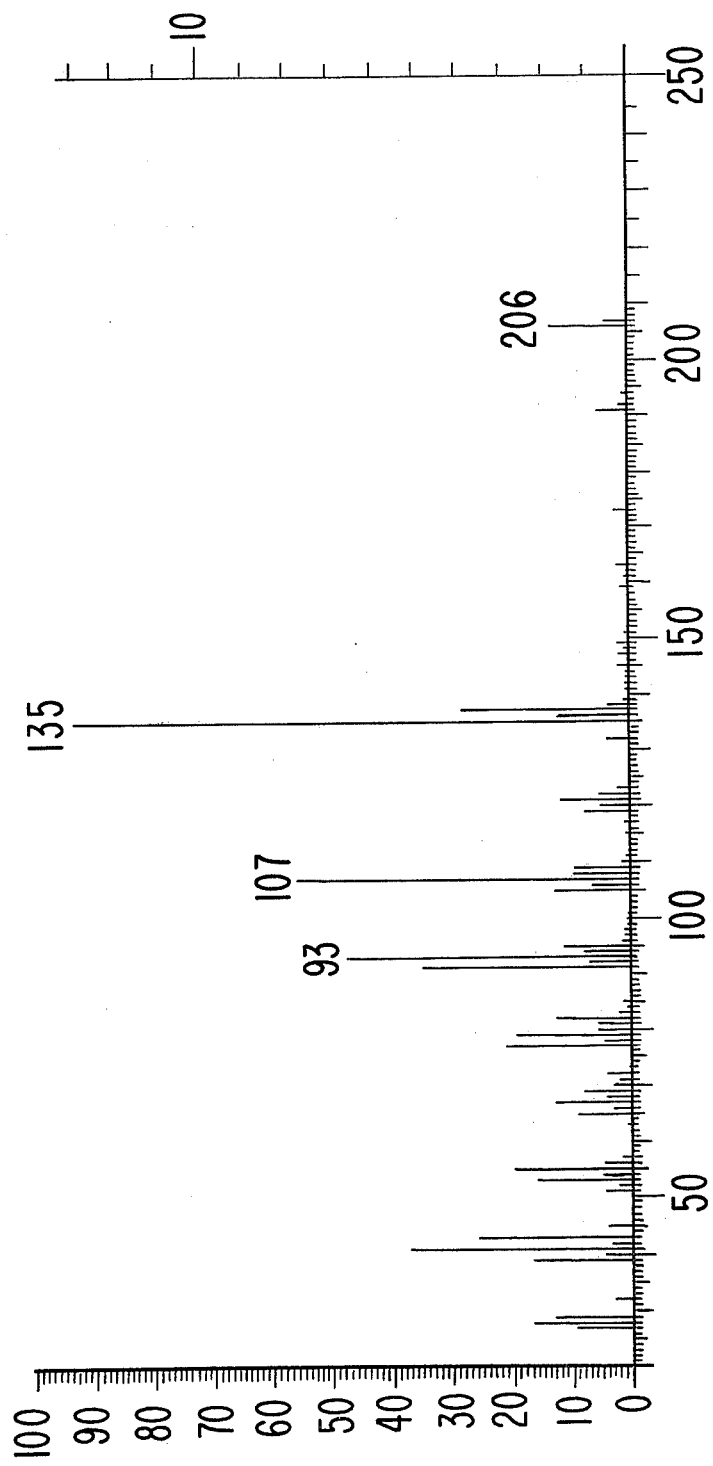

FIG. 10 is the mass spectrum for the product of Example III having the structures:

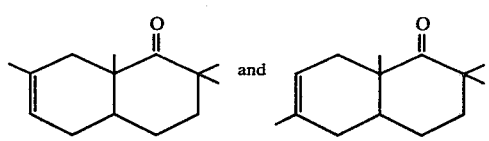

FIG. 11 is the NMR spectrum for the product of Example III having the structures:

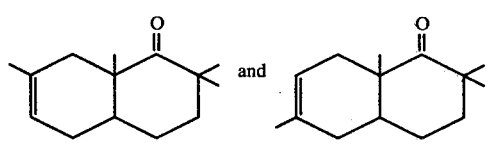

FIG. 12 is the infrared spectrum for the product of Example III having the structures:

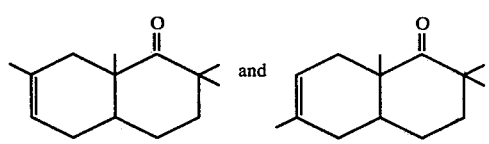

FIG. 13A is the GLC profile for the reaction mixture of Example IV (fraction 3, "cis-isomer") containing the compounds having the structures:

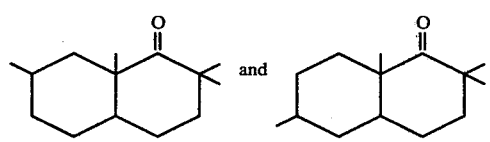

FIG. 13B is the GLC profile for the reaction mixture of Example IV spiked with reactant and thus containing the compounds having the structures:

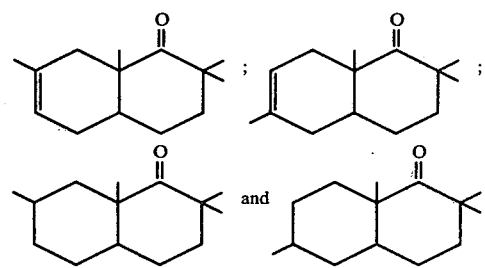

FIG. 14 is the mass spectrum for the reaction product of Example IV, fraction 3, containing the compounds having the structure:

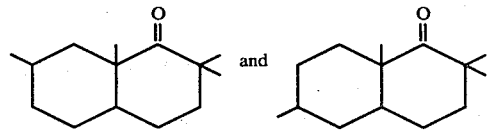

FIG. 15 is the NMR spectrum for the reaction product of Example IV, containing the compounds having the structures:

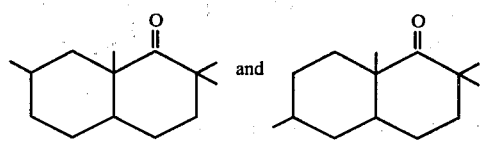

FIG. 16 is the infrared spectrum for the reaction product of Example IV, fraction 3, containing the compounds having the structures:

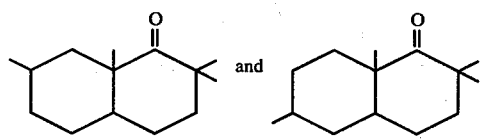

Figure 17:
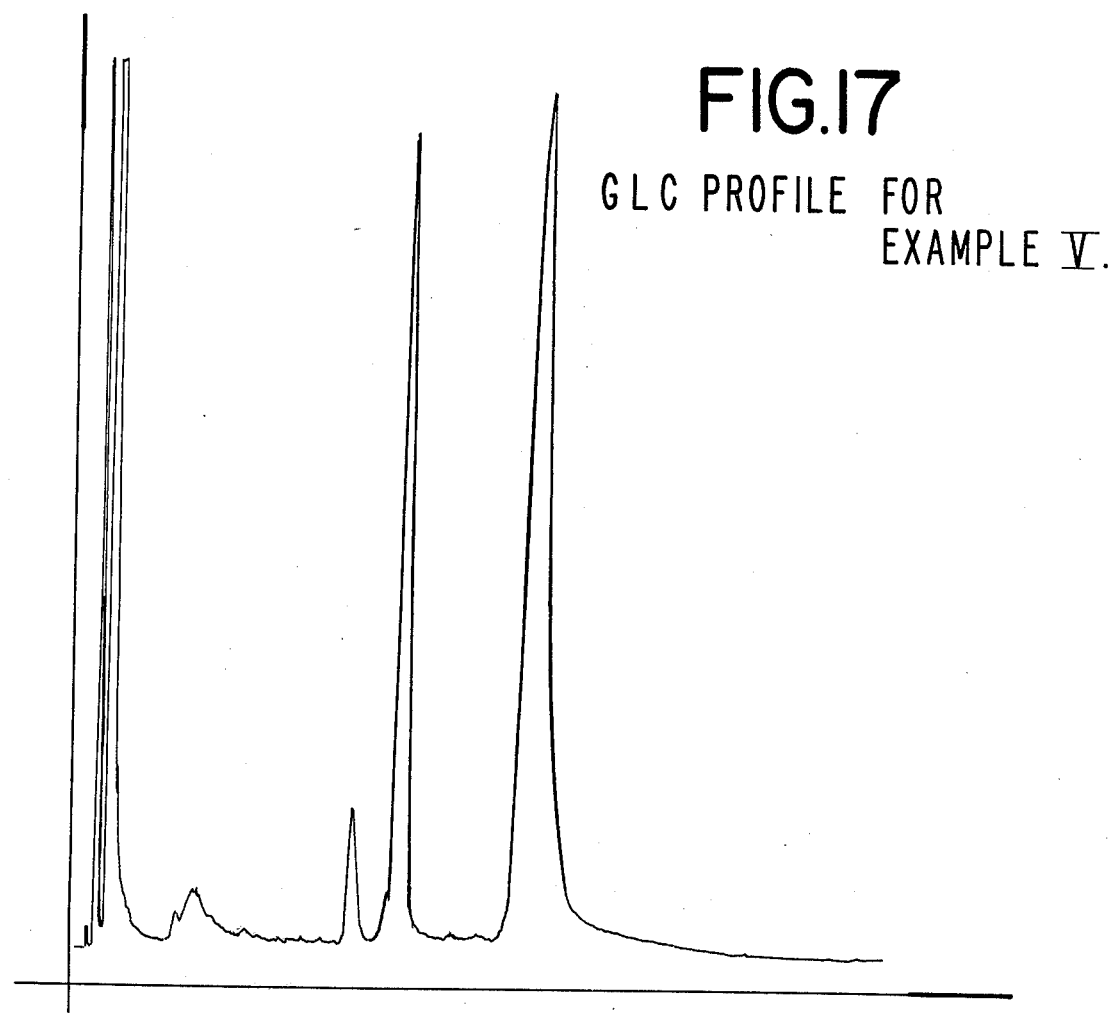

FIG. 17 is the GLC profile for the reaction product of Example V containing the compounds having the structures:

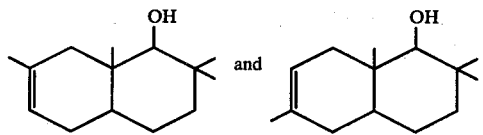

Figure 18:
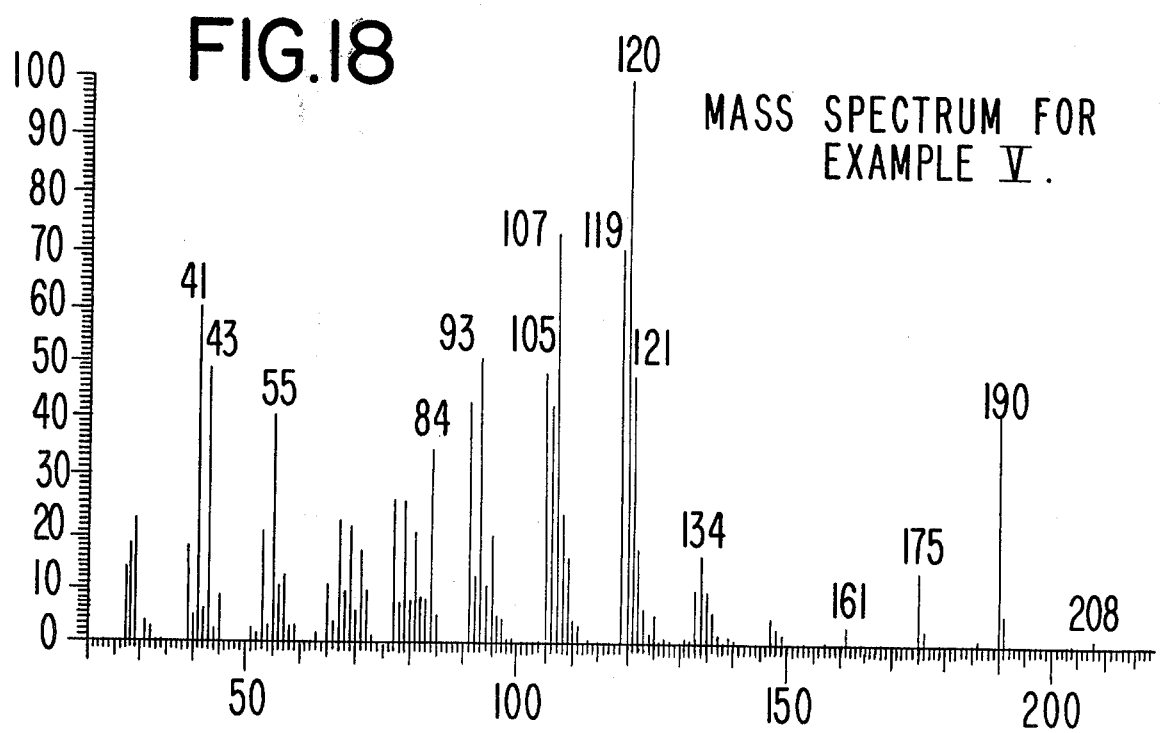

FIG. 18 is the mass spectrum for the reaction product of Example V containing the cis-isomer of the compounds having the structures:

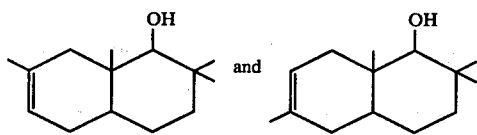

Figure 19:
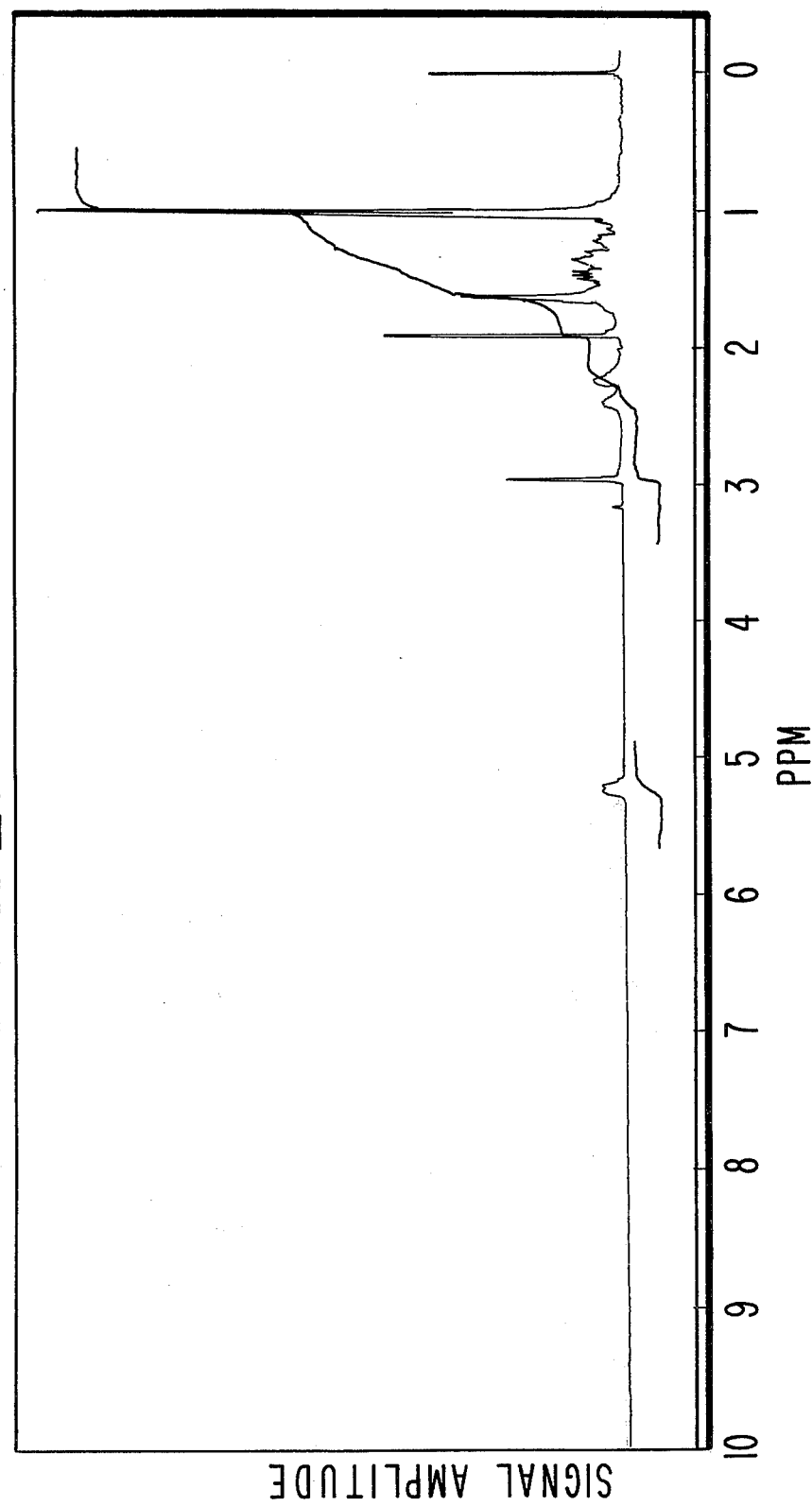

FIG. 19 is the NMR spectrum for the reaction product of Example V containing the cis-isomer of the compounds having the structures:

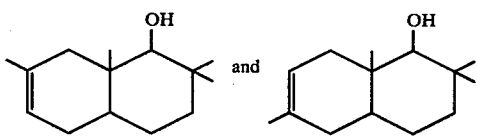

Figure 20:
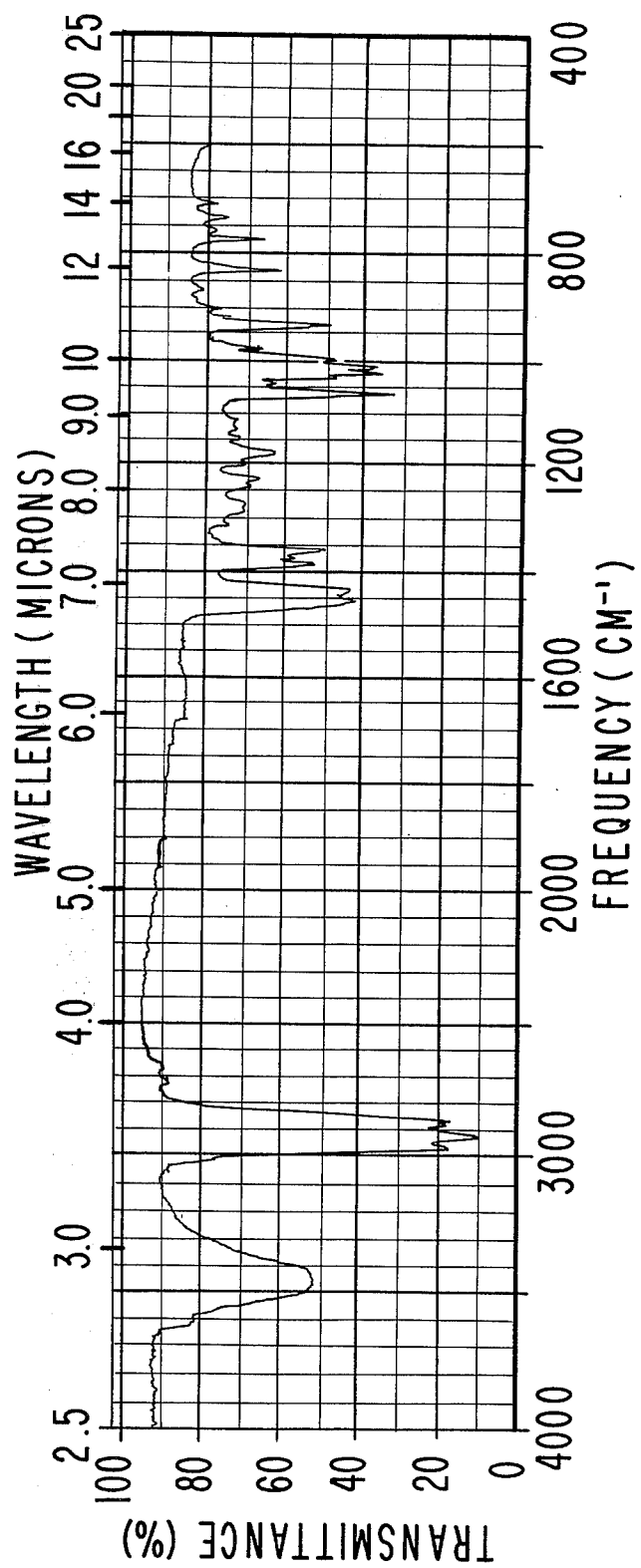

FIG. 20 is the infrared spectrum for the reaction product of Example V containing the cis-isomer of the compounds having the structures:

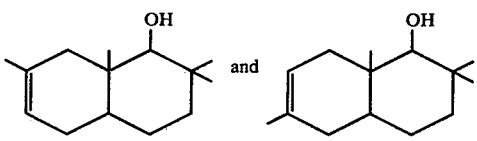

FIG. 21 is the GLC profile for the reaction product of Example VI(A), fraction 7, containing the compounds having the structures:

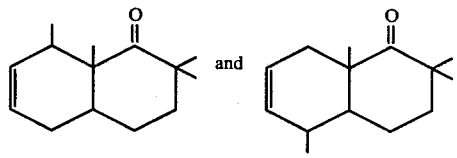

FIG. 22 is the mass spectrum for the reaction product of Example VI(A), fraction 7, containing the compounds having the structures:

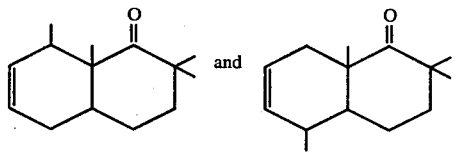

FIG. 23 is the NMR spectrum for the reaction product of Example VI(A) containing the compounds having the structures:

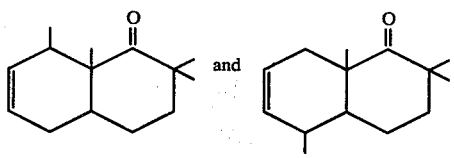

Figure 24:
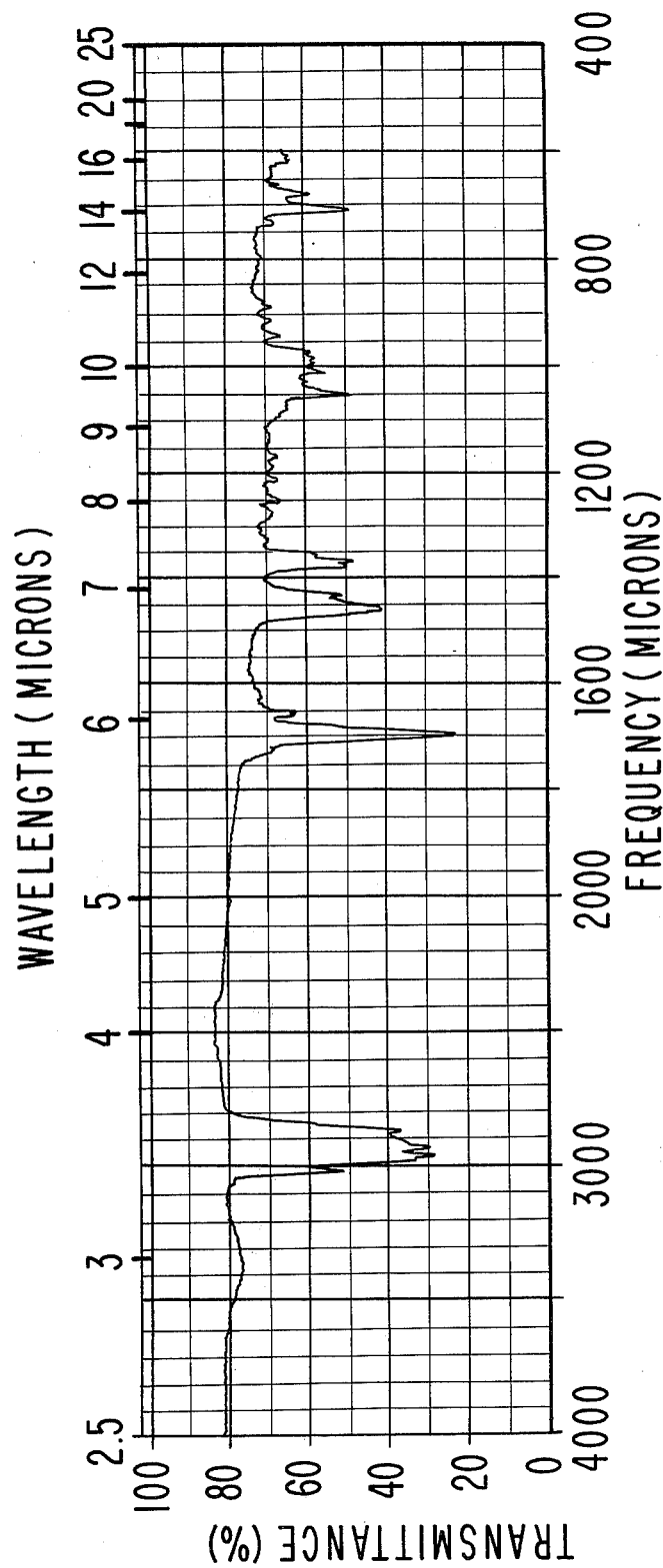

FIG. 24 is the infrared spectrum for the reaction product of Example VI(A) containing the compounds having the structures:

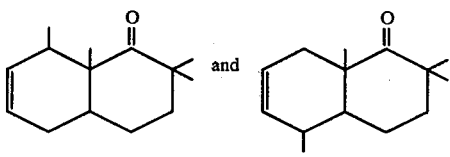

Figure 25:
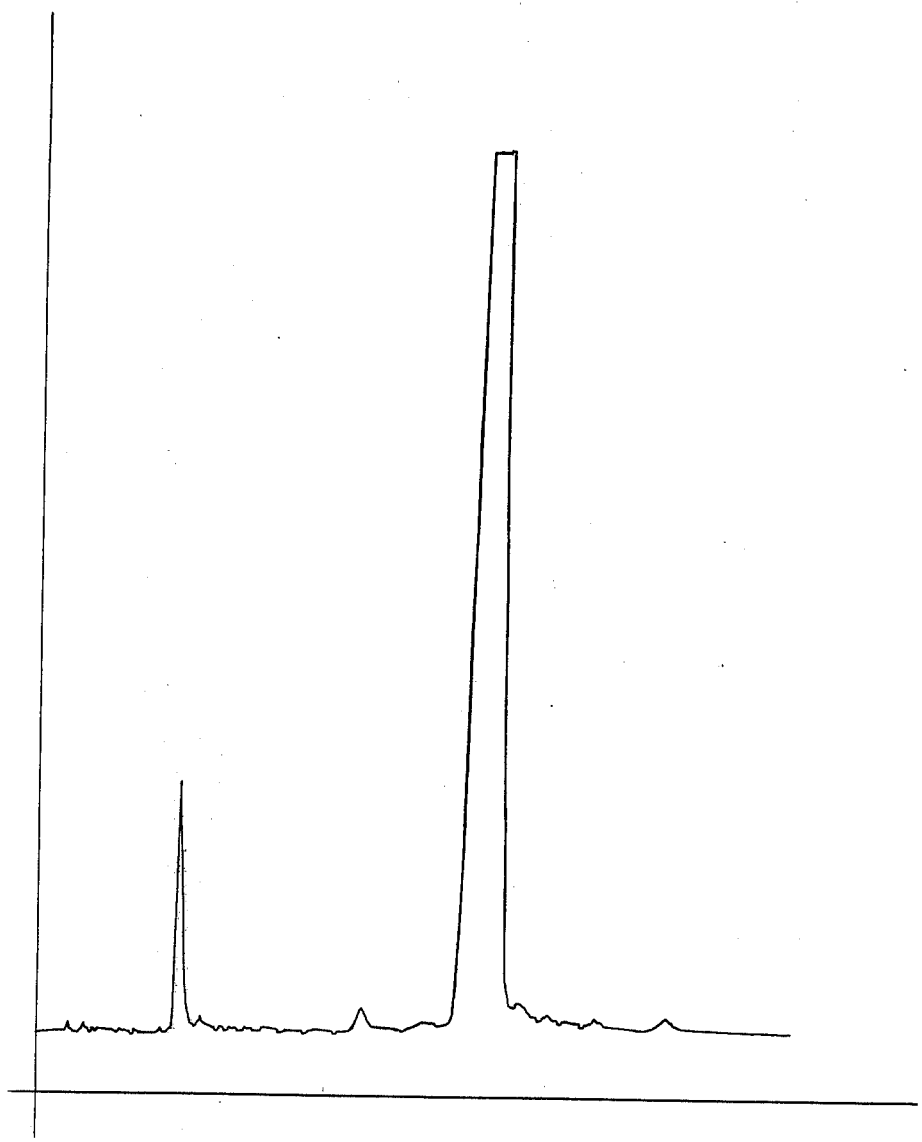

FIG. 25 is the GLC profile for the reaction product of Example VI(B) (bulked fractions 2-7) containing the compounds having the structures:

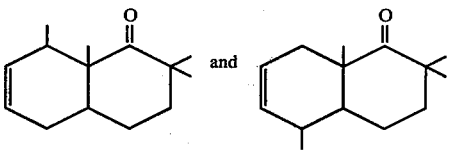

FIG. 26A is the GLC profile for the crude product of the reaction of Example VII(A) containing the compound having the structure:

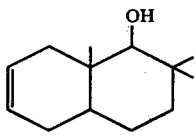

FIG. 26B is the GLC profile for bulked fractions 1-3 of the distillation product of the reaction product of Example VII(A) containing the compound having the structure:

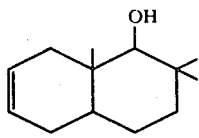

FIG. 27 is the mass spectrum for the reaction product of Example VII(A), bulked fractions 1-3, containing the compound having the structure:

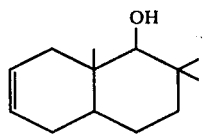

Figure 28:
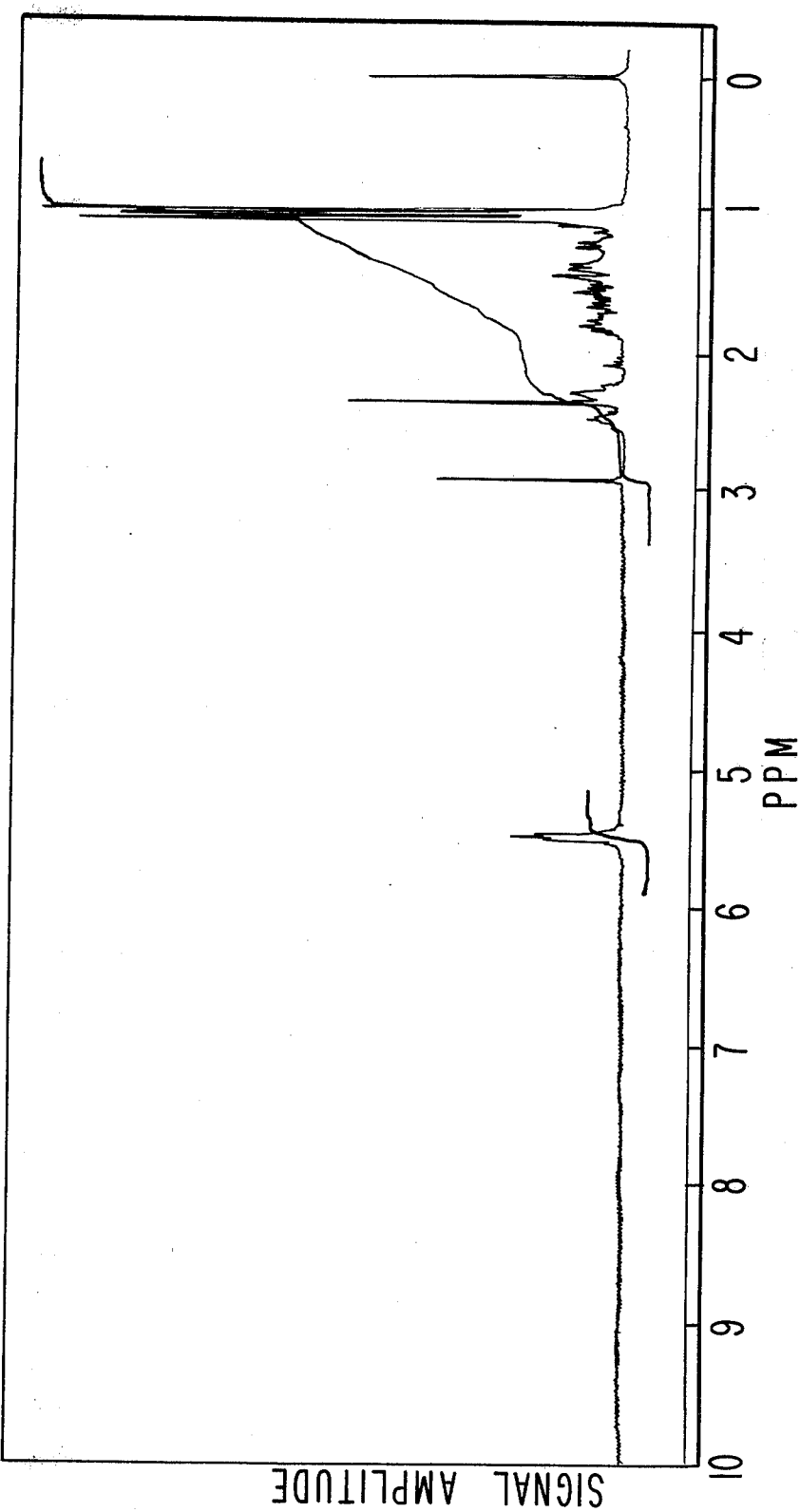

FIG. 28 is the NMR spectrum for the reaction product of Example VII(A), bulked fractions 1-3, containing the compound having the structure:

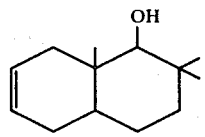

Figure 29:
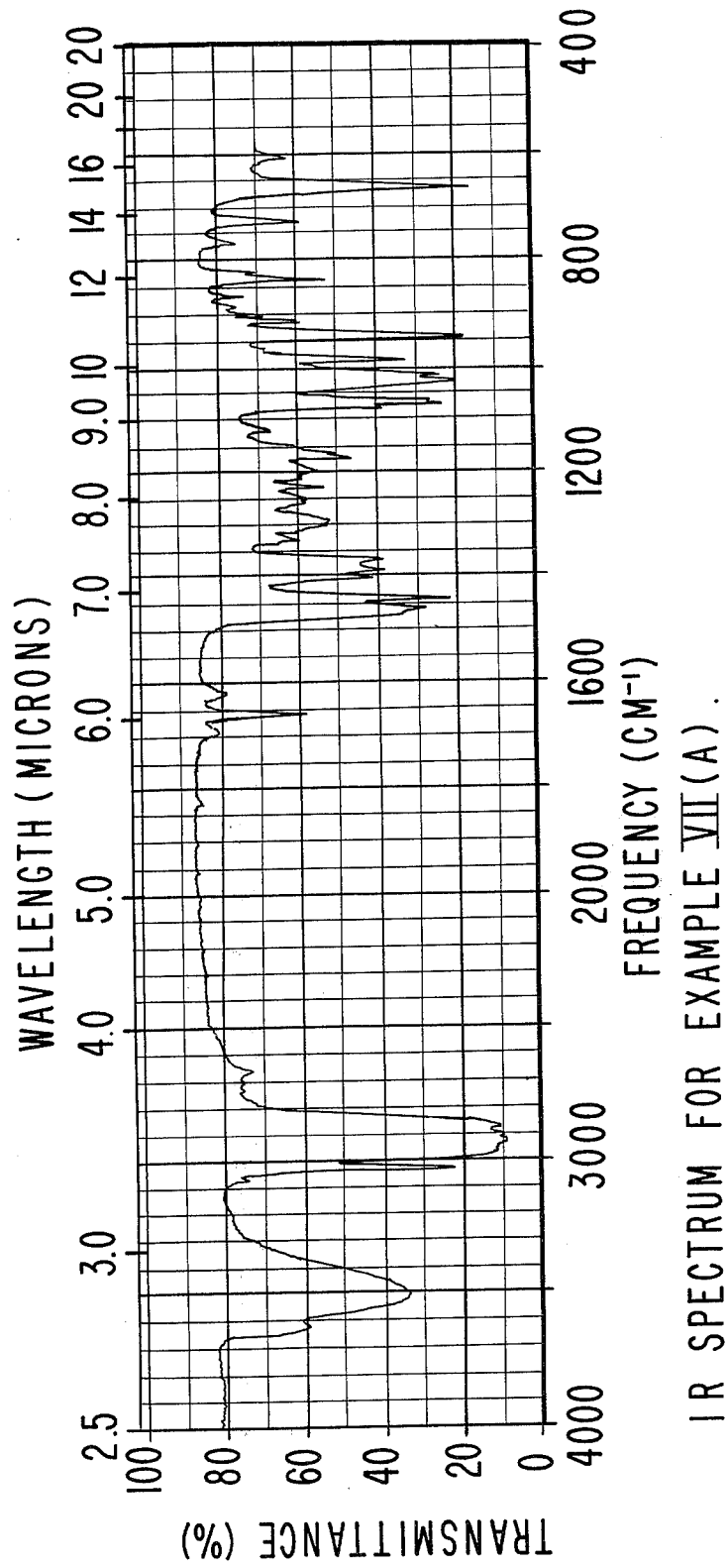

FIG. 29 is the infrared spectrum for the reaction product of Example VII(A), bulked fractions 1-3, containing the compound having the structure:

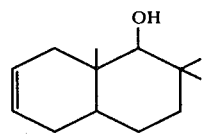

Figure 30:
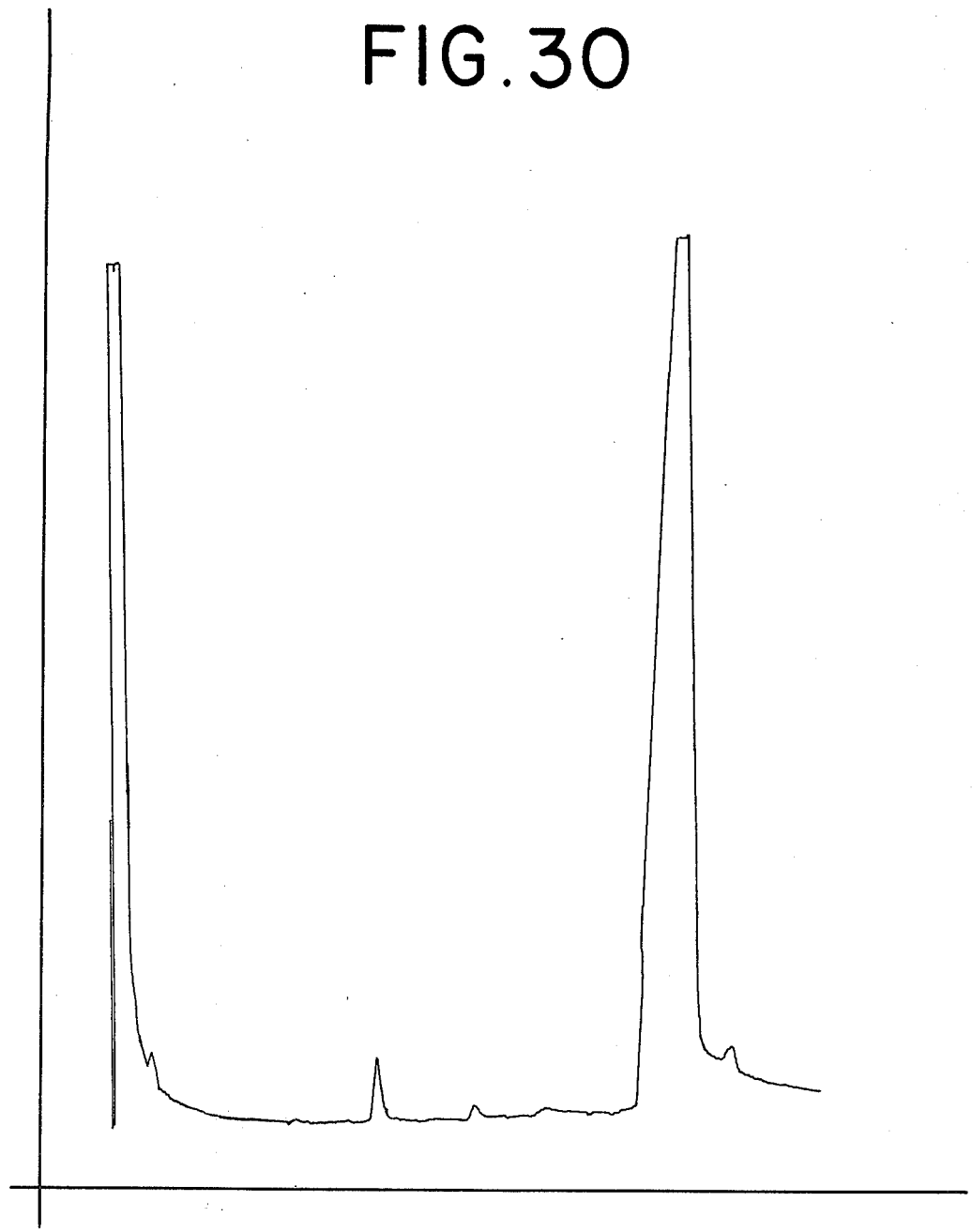

FIG. 30 is the GLC profile for the reaction product, after 1.5 hours of Example VII(B) containing the compound having the structure:

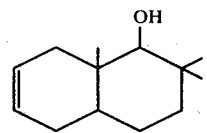

Figure 31:
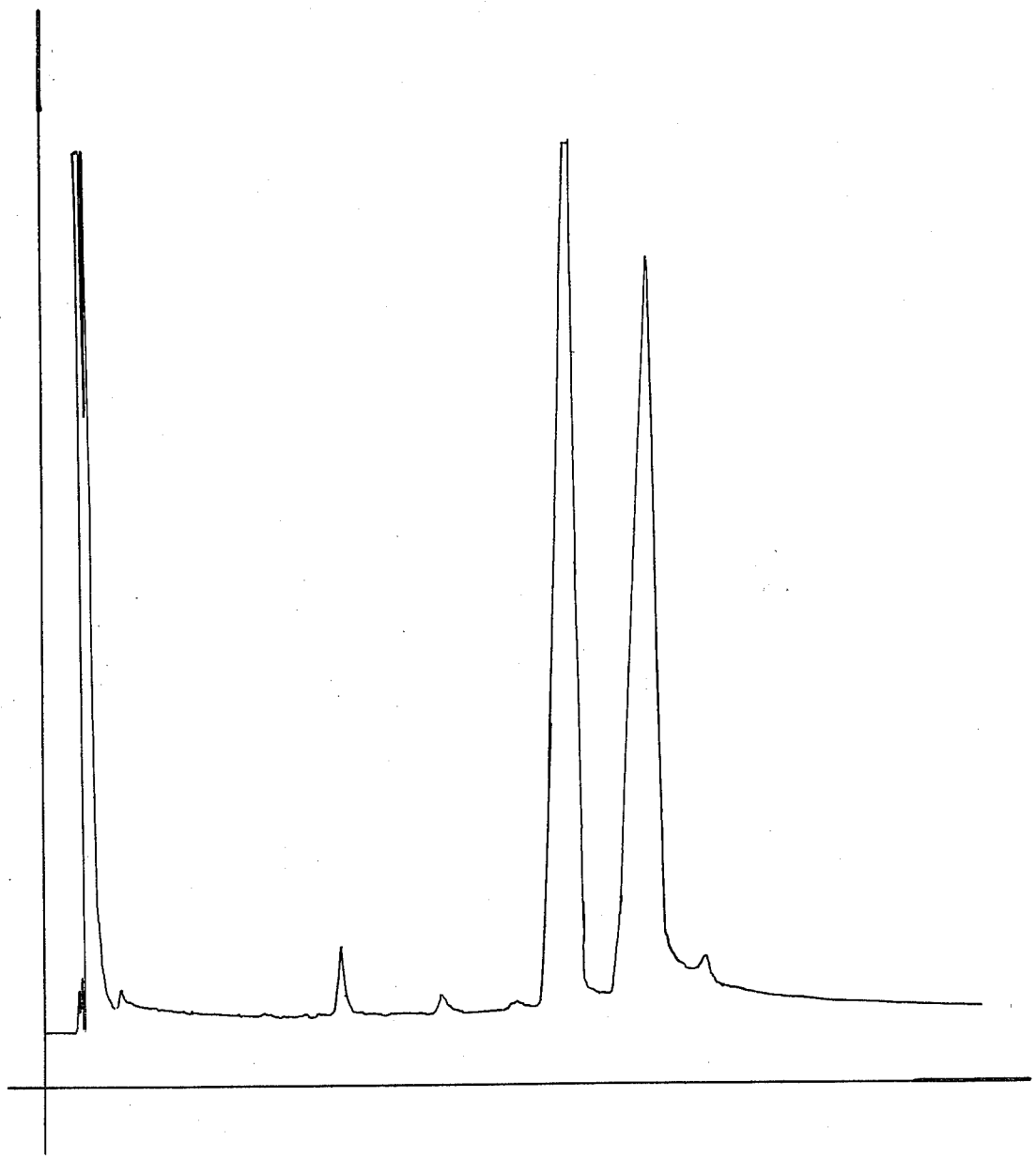

FIG. 31 is the GLC profile for the reaction products, of Example VII(B), spiked with reactant, containing the compounds having the structures:

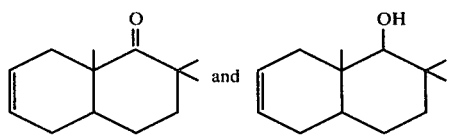

Figure 32:
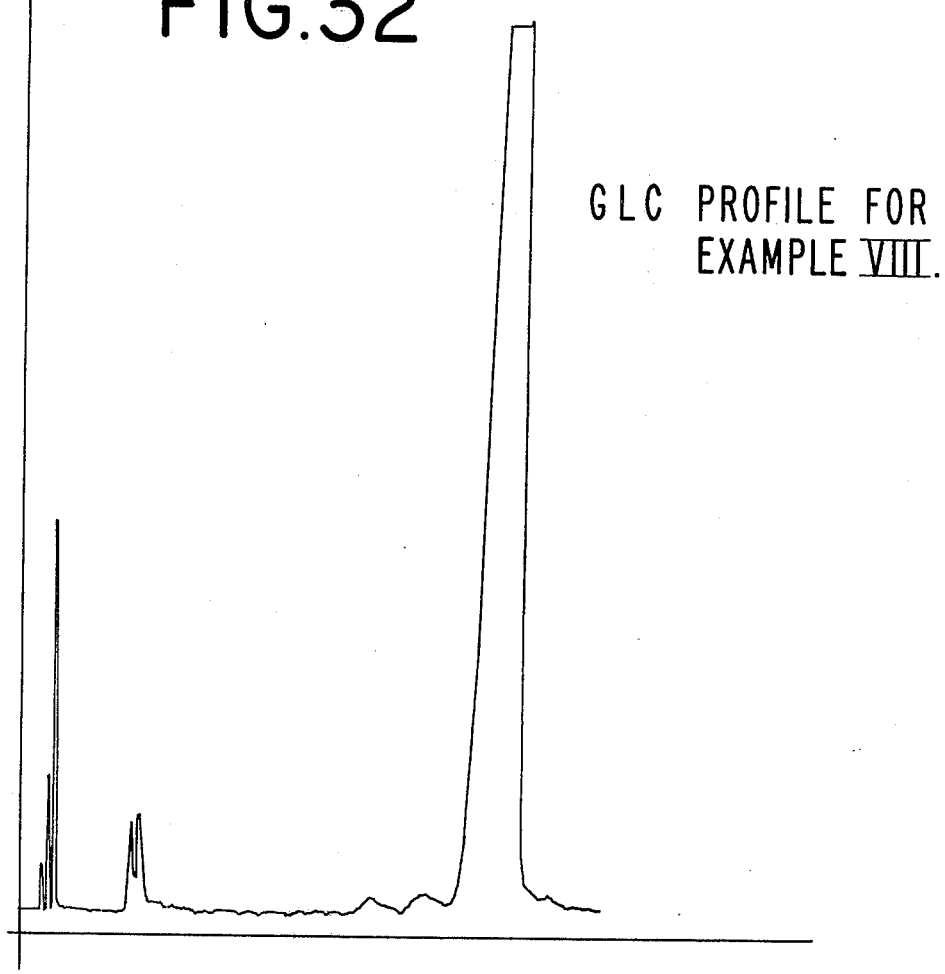

FIG. 32 is the GLC profile for the reaction product of Example VIII containing the compounds having the structures:

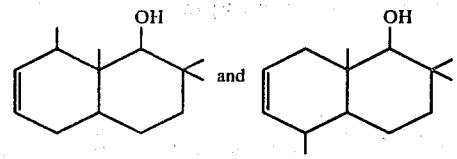

Figure 33:
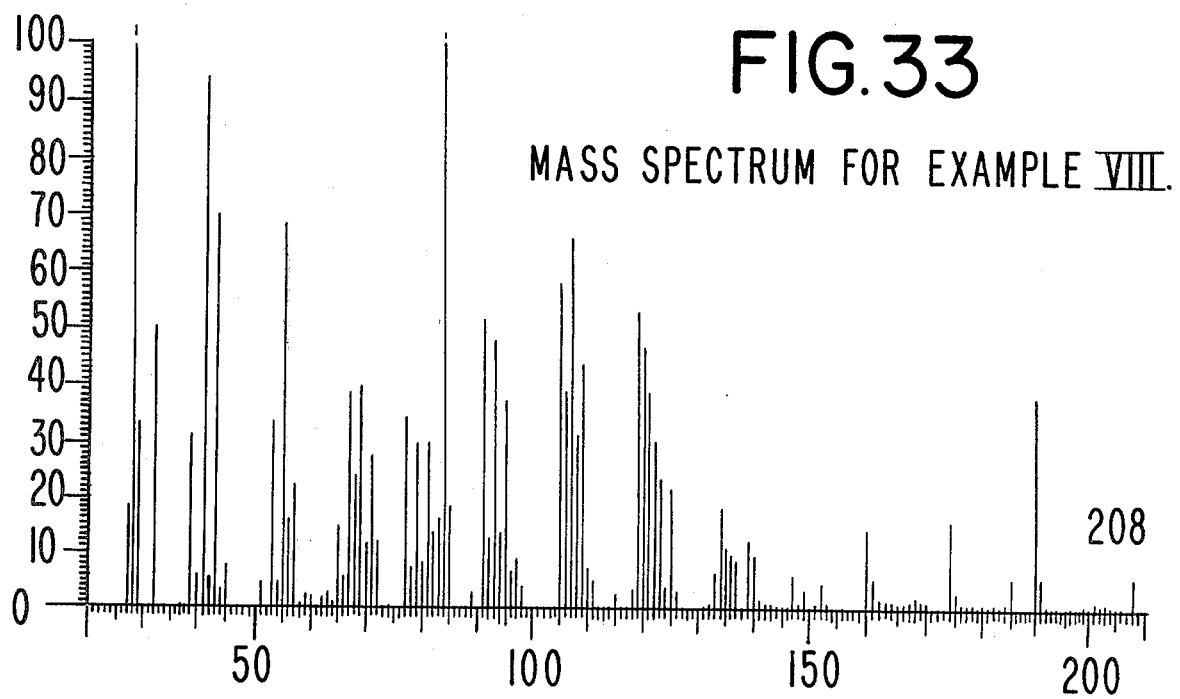

FIG. 33 is the mass spectrum for the reaction product of Example VIII containing the compounds having the structures:

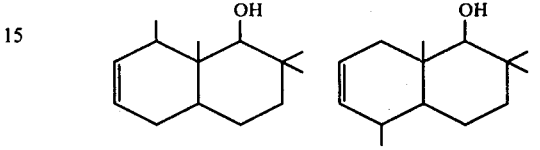

Figure 34:
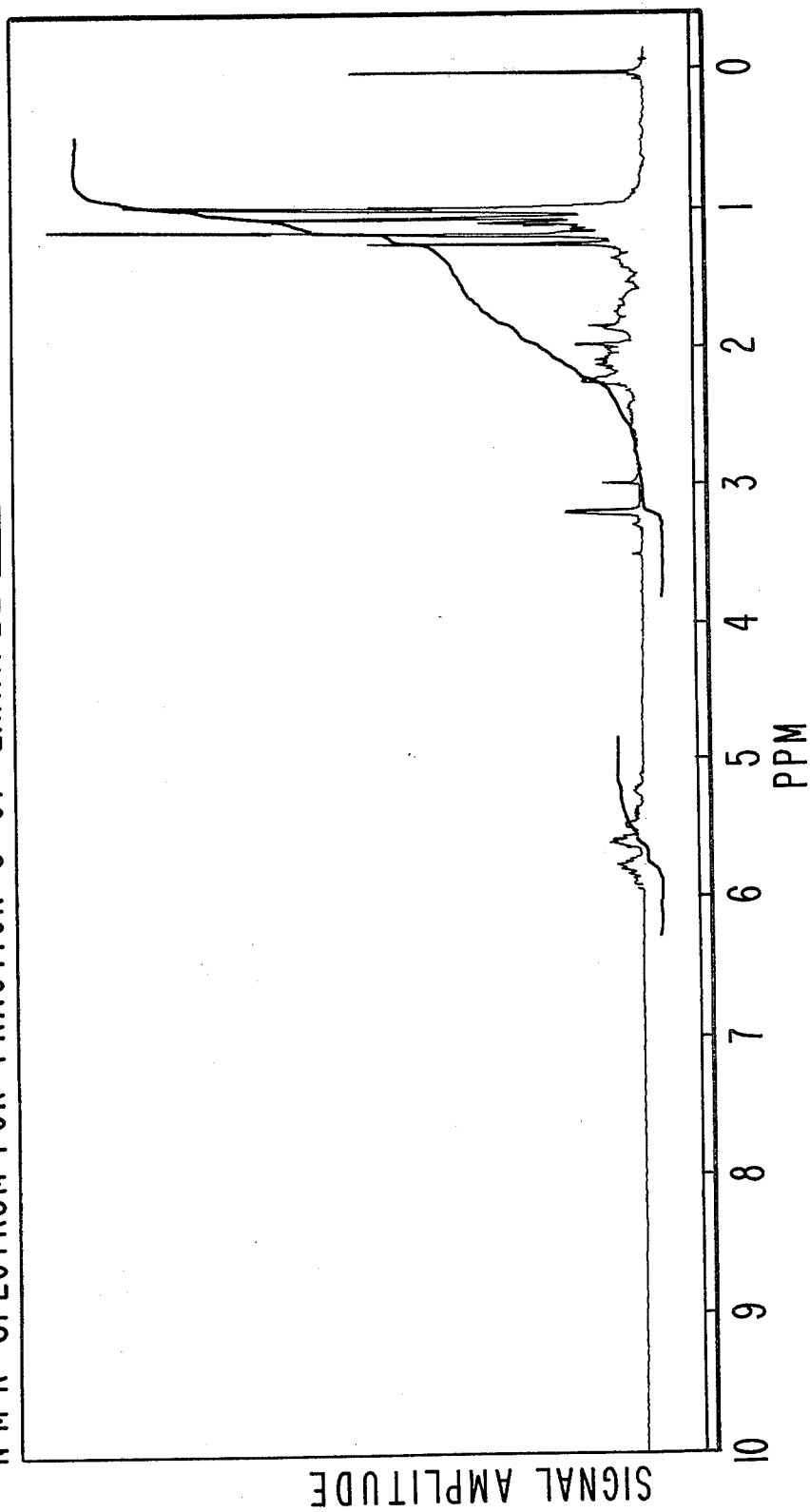

FIG. 34 is the NMR spectrum for the reaction product of Example VIII, fraction 3, containing the compounds having the structures:

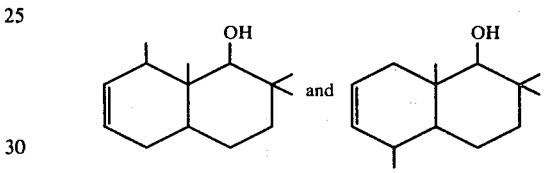

Figure 35:
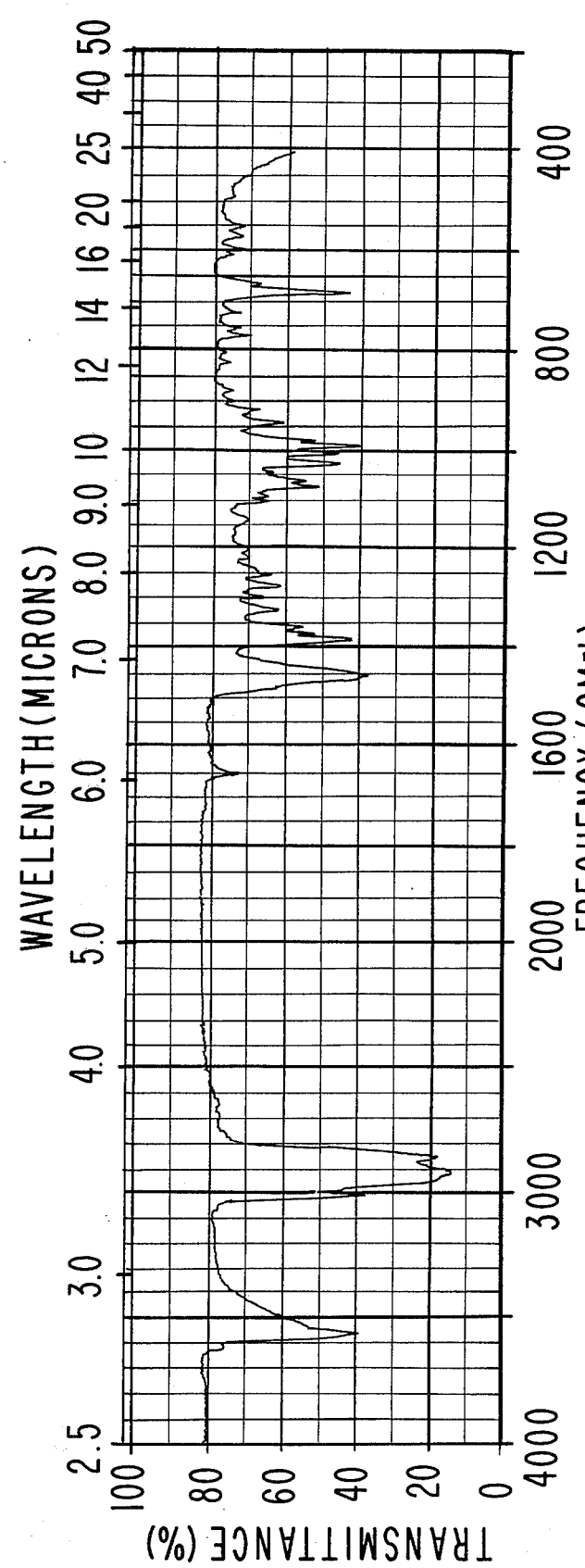

FIG. 35 is the infrared spectrum for fraction 3 of the distillation product of the reaction product of Example VIII containing the compounds having the structures:

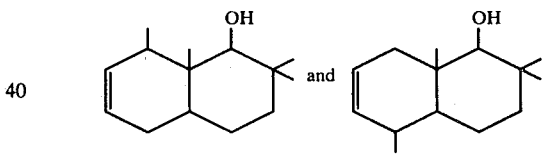

Figure 36:
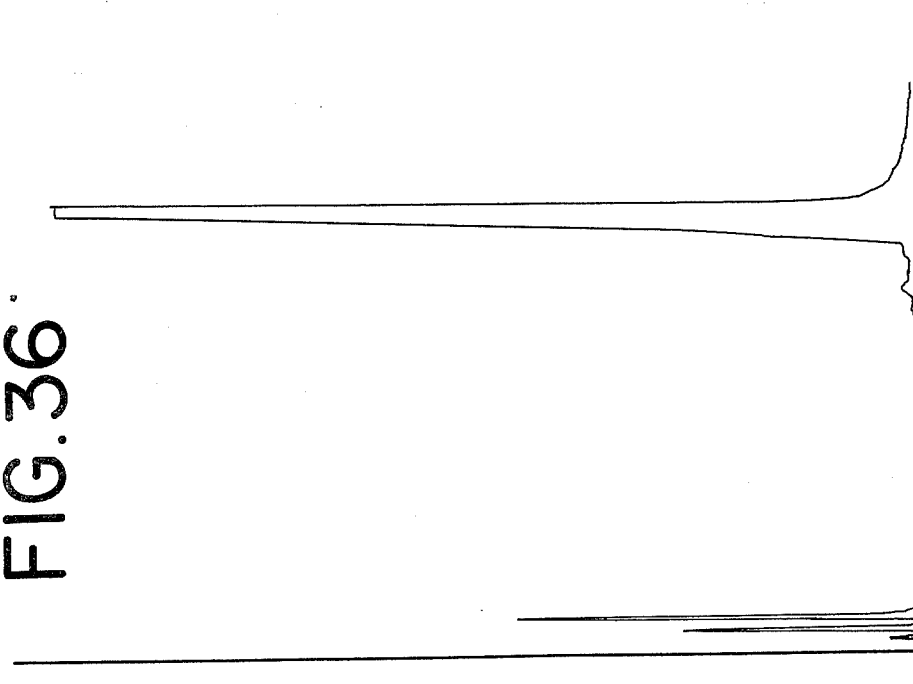

FIG. 36 is the GLC profile for the reaction product of Example IX containing the compounds having the structures:

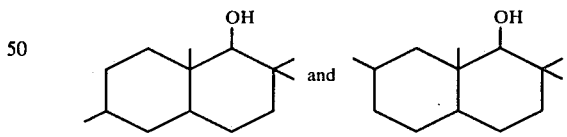

Figure 37:
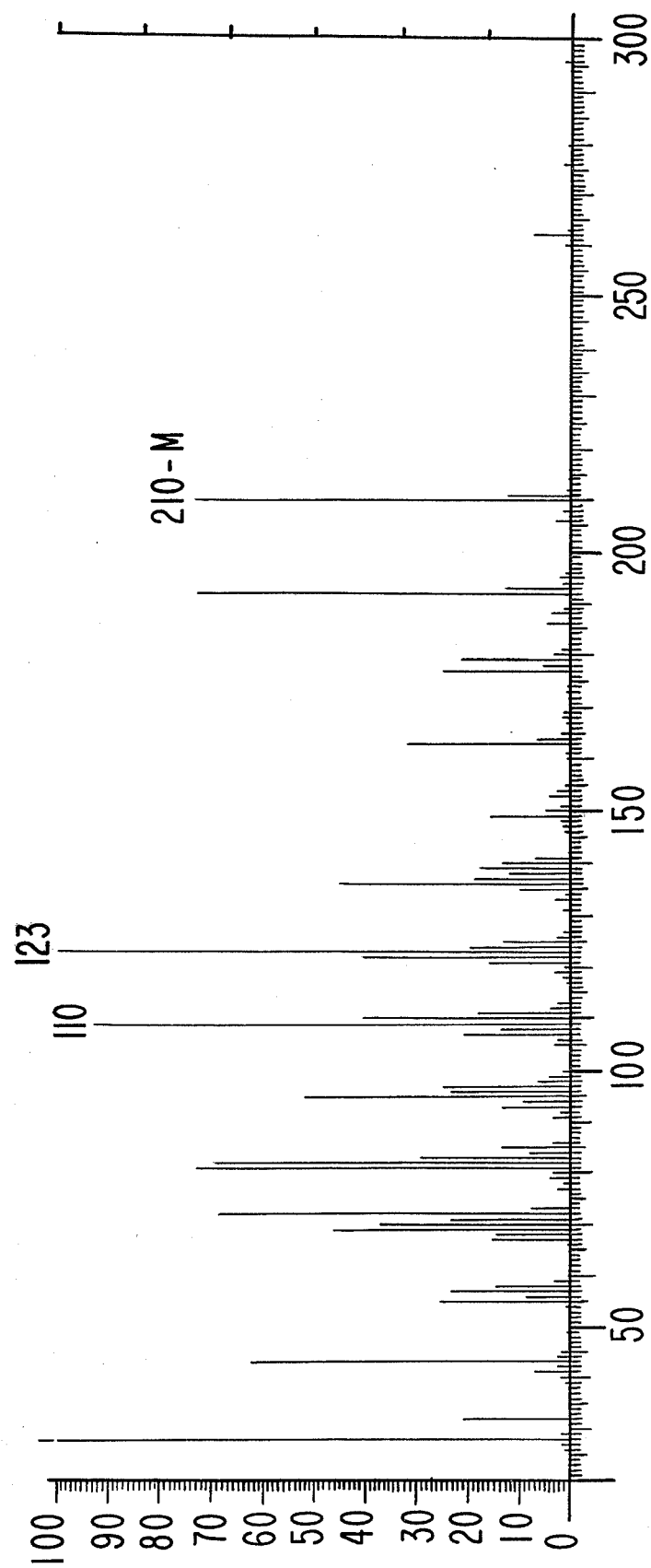

FIG. 37 is the mass spectrum for the reaction product of Example IX containing the compounds having the structures:

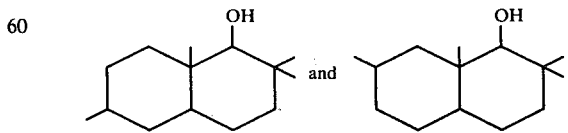

Figure 38:
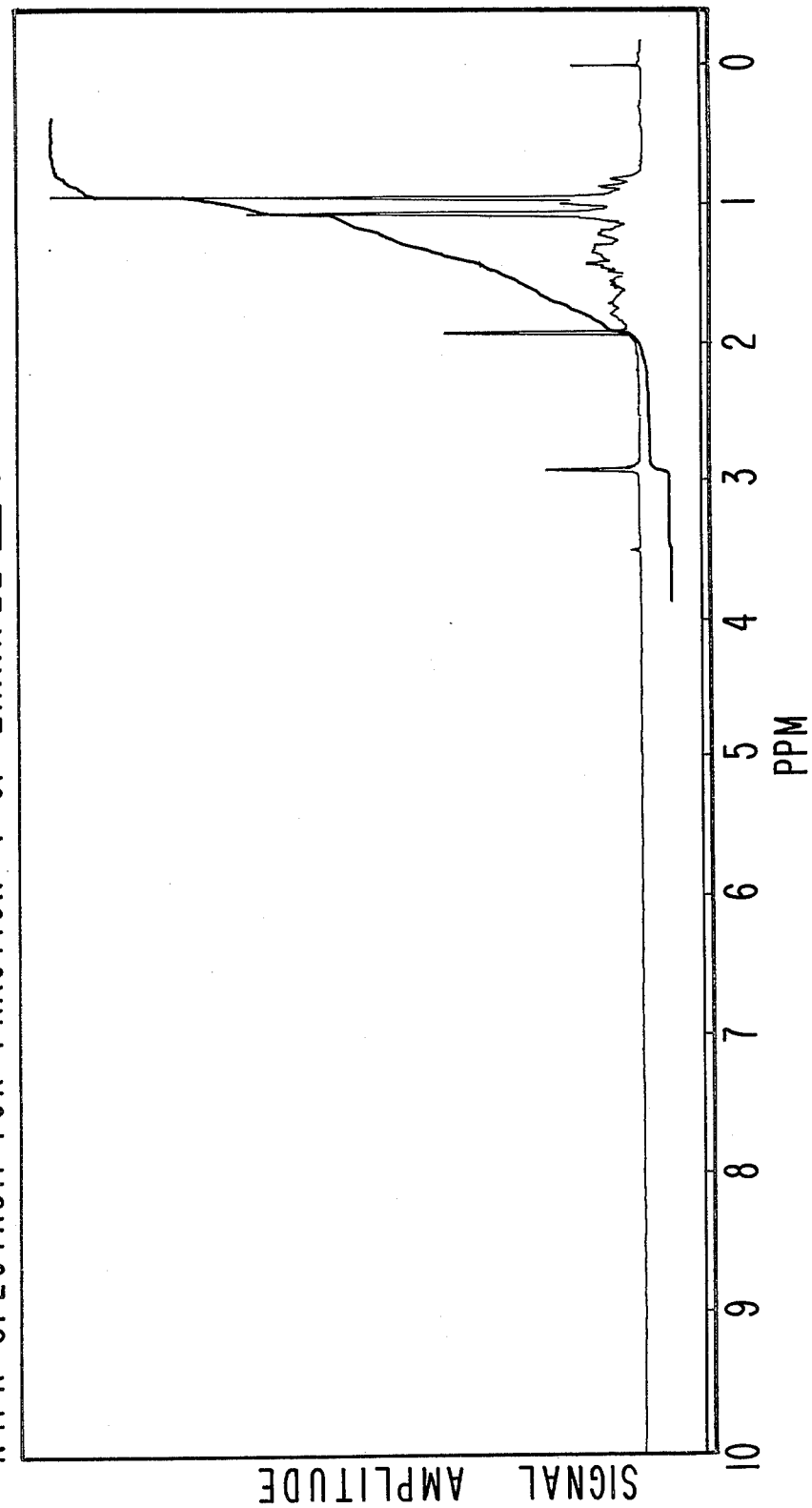

FIG. 38 is the NMR spectrum for the distillation product, fraction 4, of the reaction product of Example IX containing the compounds having the structures:

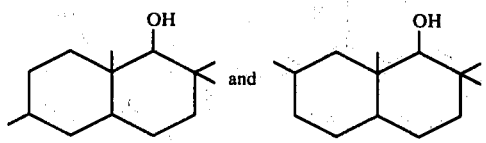

Figure 39:
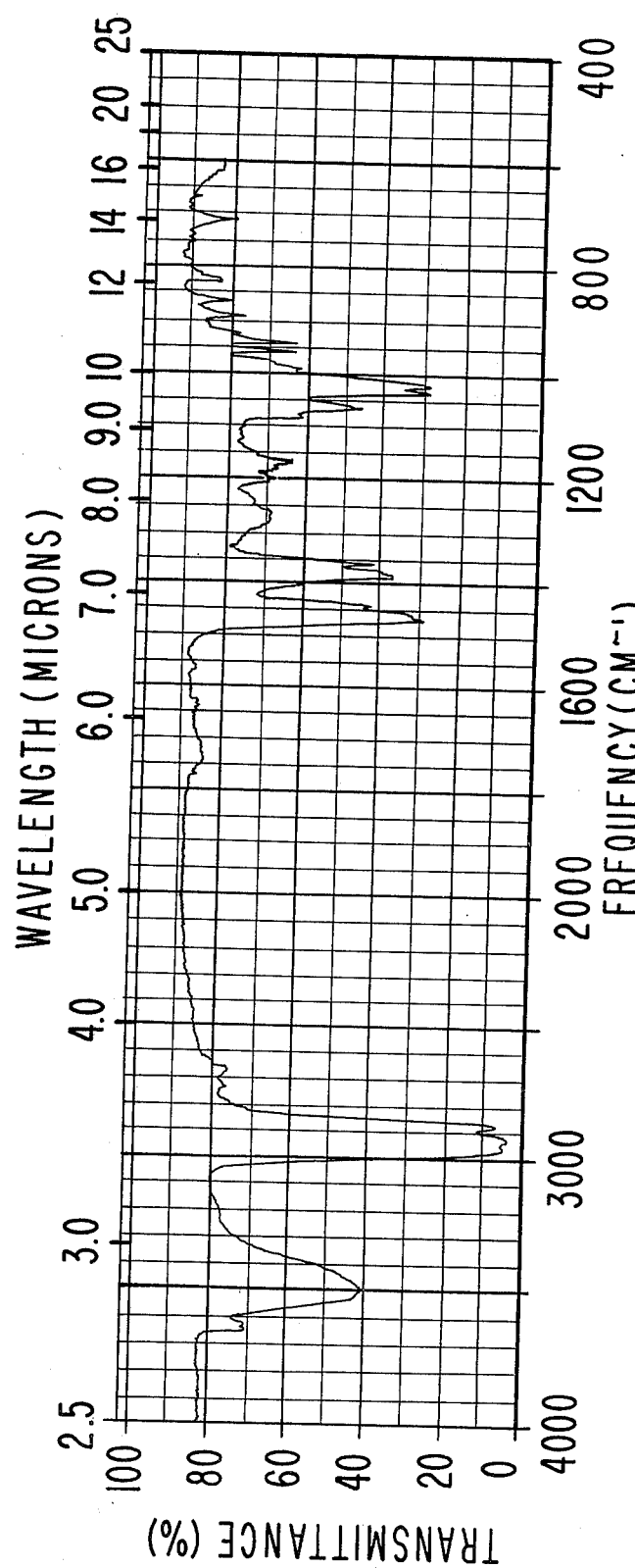

FIG. 39 is the infrared spectrum for fraction 4 of the distillation product of the reaction product of Example IX containing the compounds having the structures:

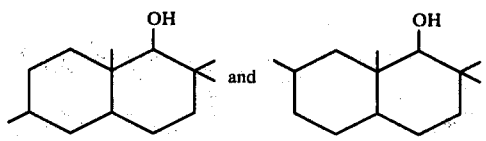

Figure 40:
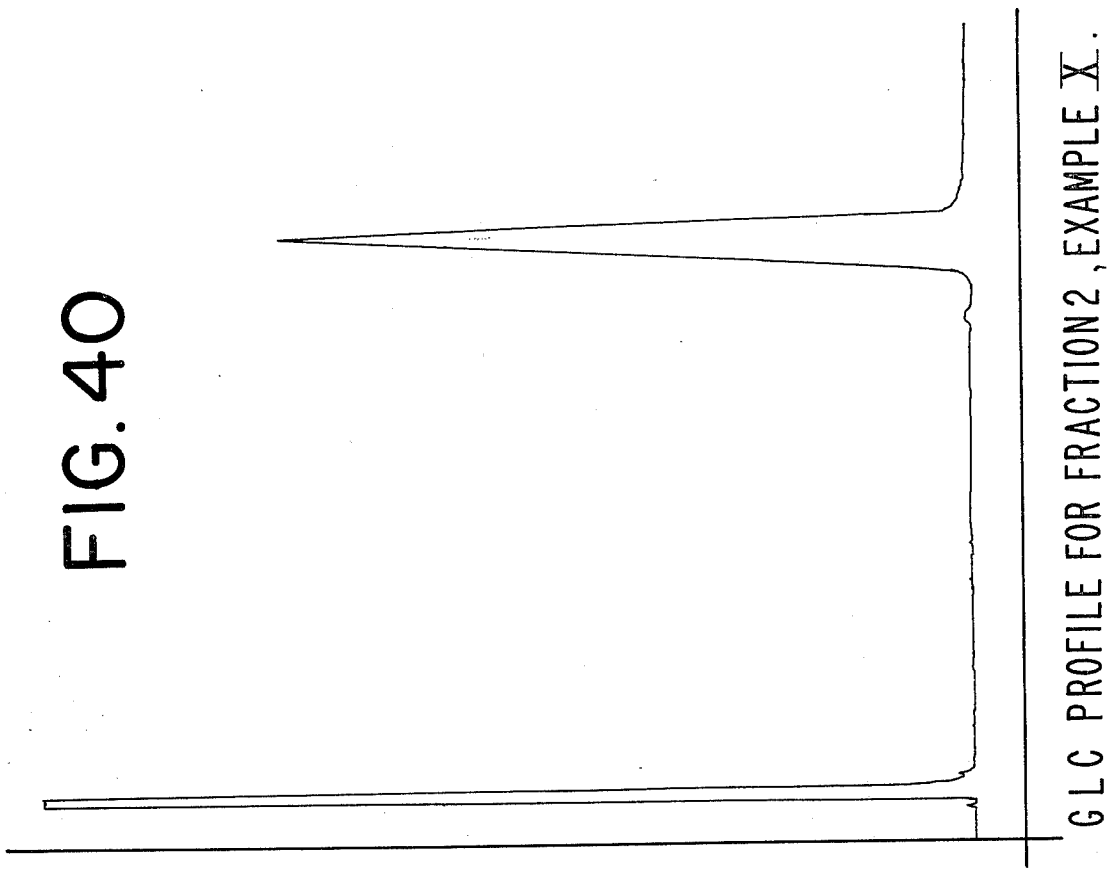

FIG. 40 is the GLC profile for the reaction product of Example X, containing the compound having the structure:

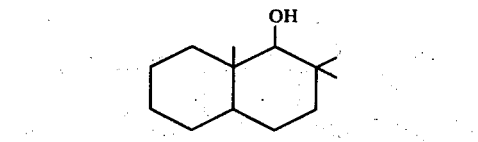

FIG. 41 is the mass spectrum for the reaction product of Example X, containing the compound having the structure:

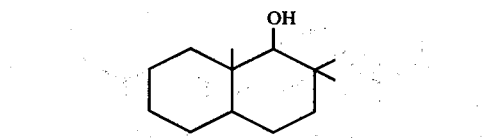

Figure 42:
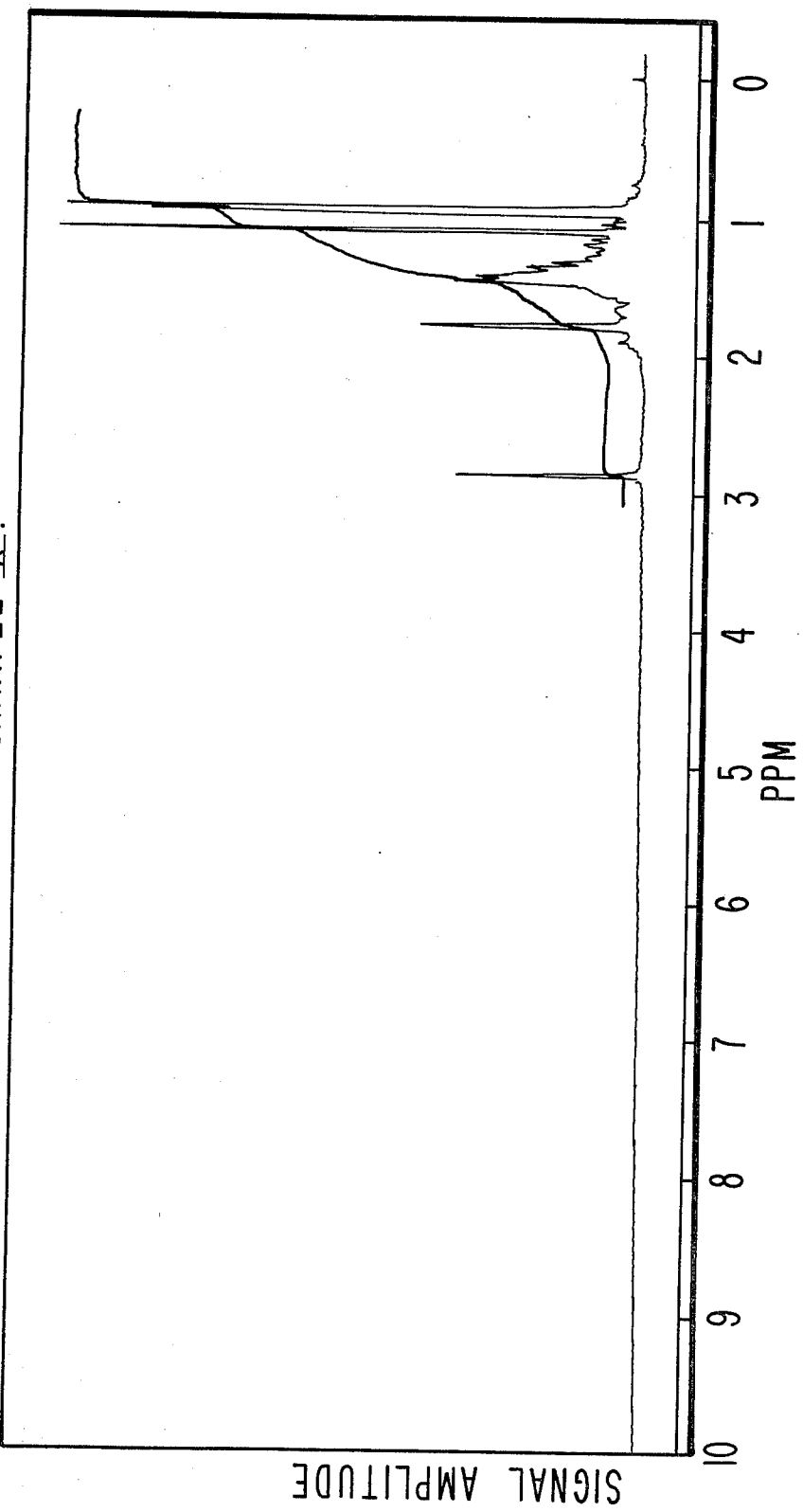

FIG. 42 is the NMR spectrum for fraction 1 of the distillation product of the reaction product of Example X, containing the compound having the structure:

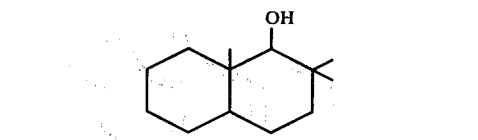

FIG. 43 is the infrared spectrum for fraction 1 of the distillation product of the reaction product of Example X, containing the compound having the structure:

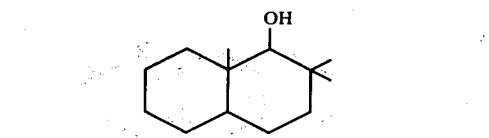

Figure 44:
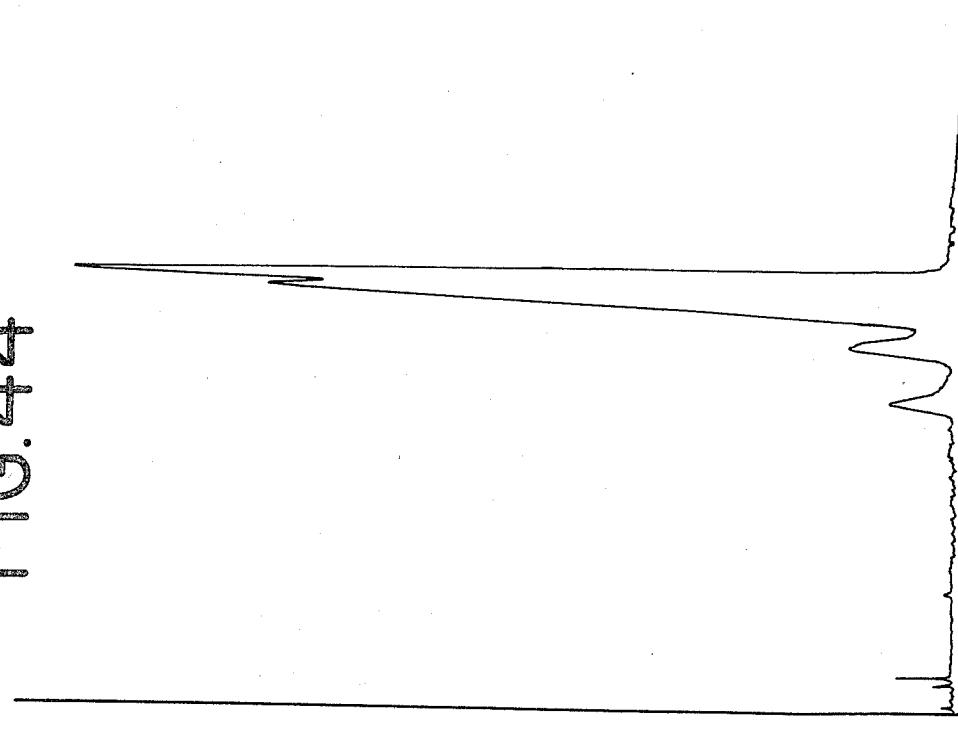

FIG. 44 is the GLC profile (fraction 3) for the reaction product of Example XI containing the compounds having the structures:

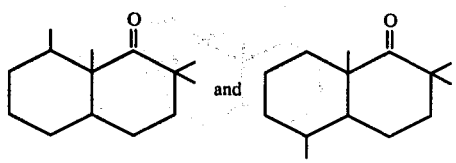

Figure 45:
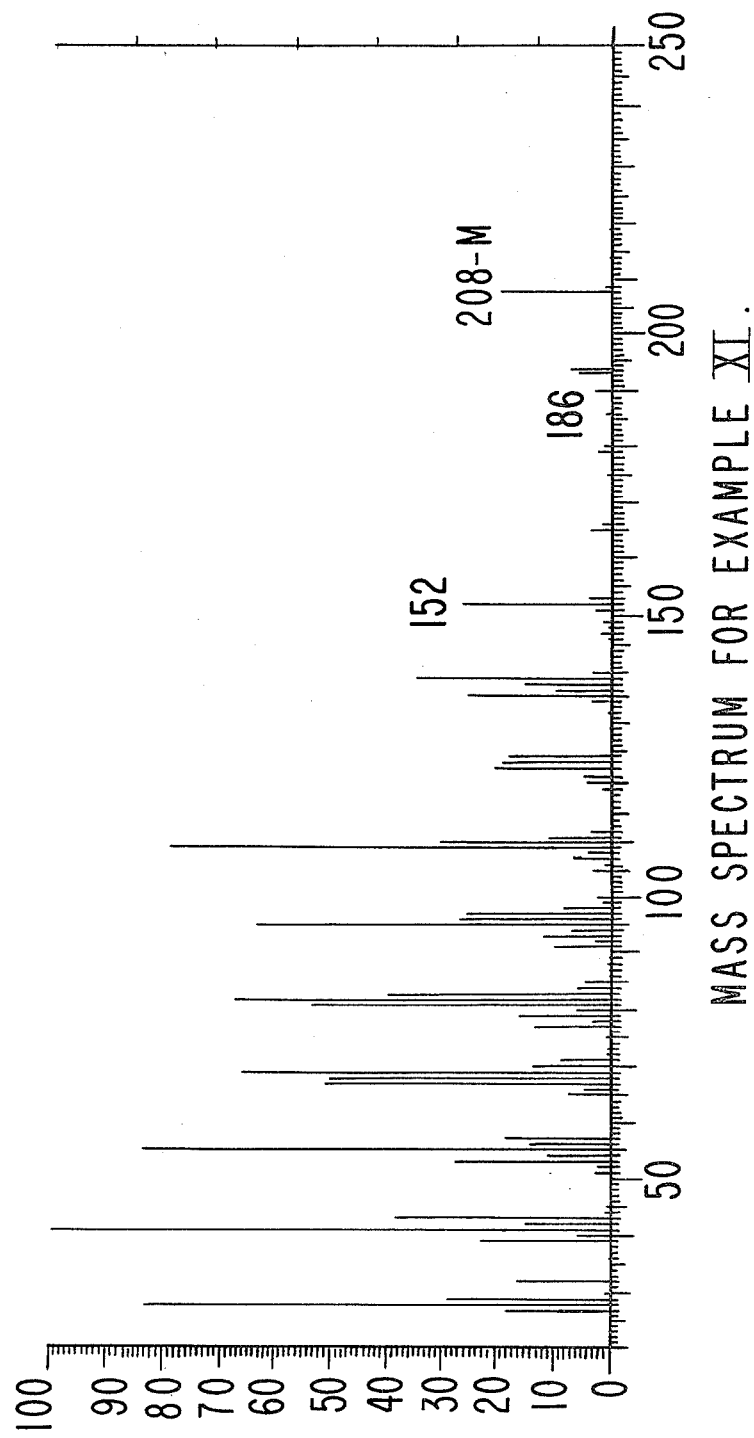

FIG. 45 is the mass spectrum for the reaction product of Example XI, containing the compounds having the structures:

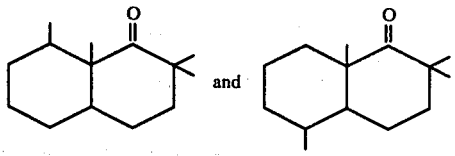

Figure 46:
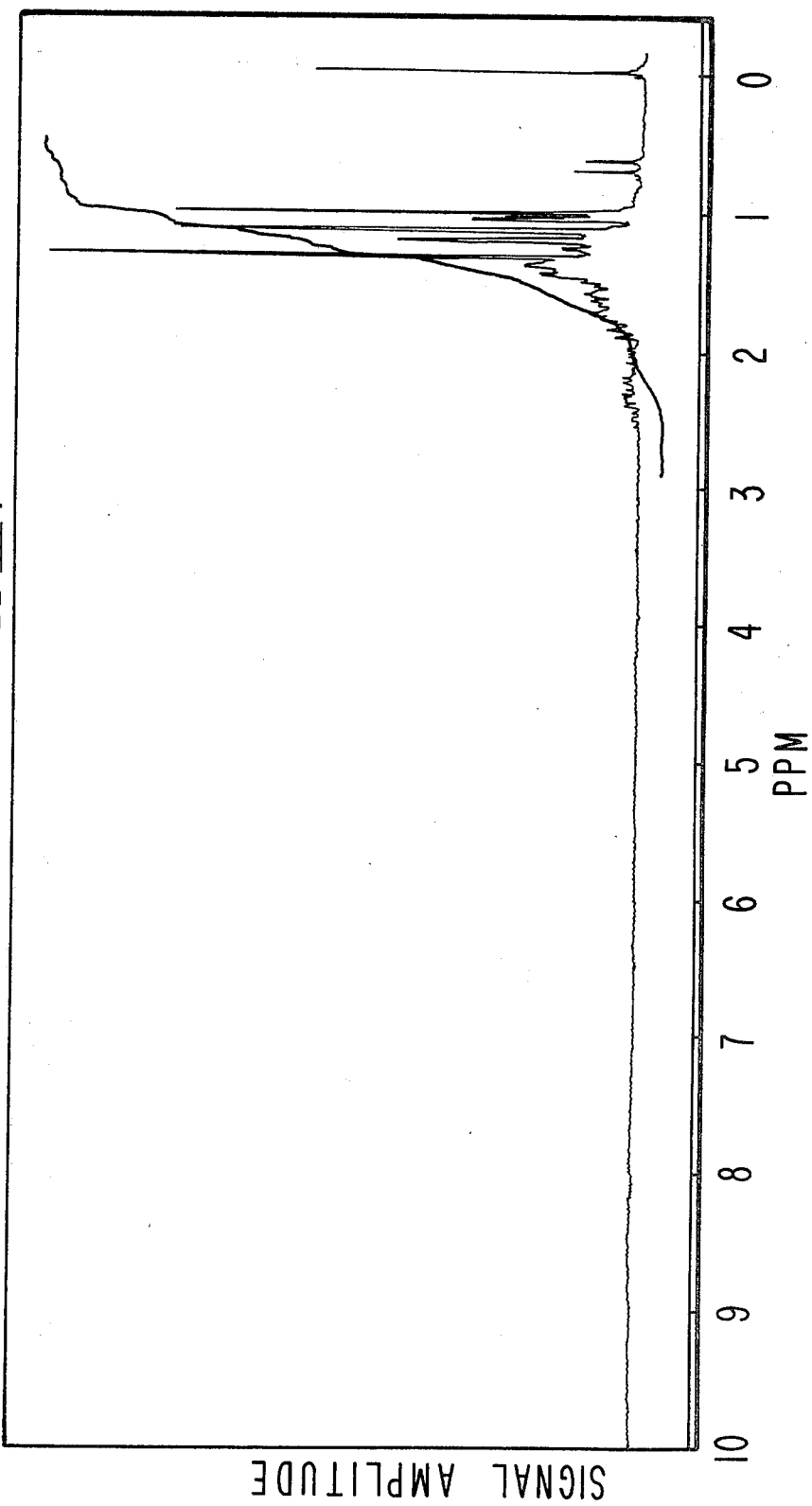

FIG. 46 is the NMR spectrum for fraction 4 of the distillation product of the reaction product of Example XI containing the compounds having the structures:

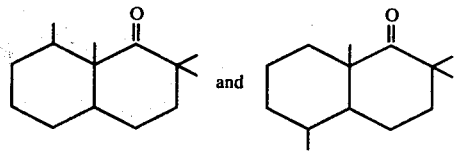

FIG. 47 is the infrared spectrum for fraction 4 of the distillation product of the reaction product of Example XI containing the compounds having the structures:

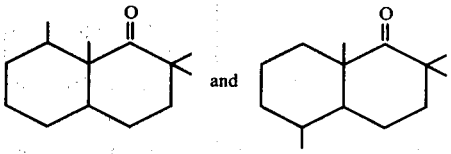

Figure 48:
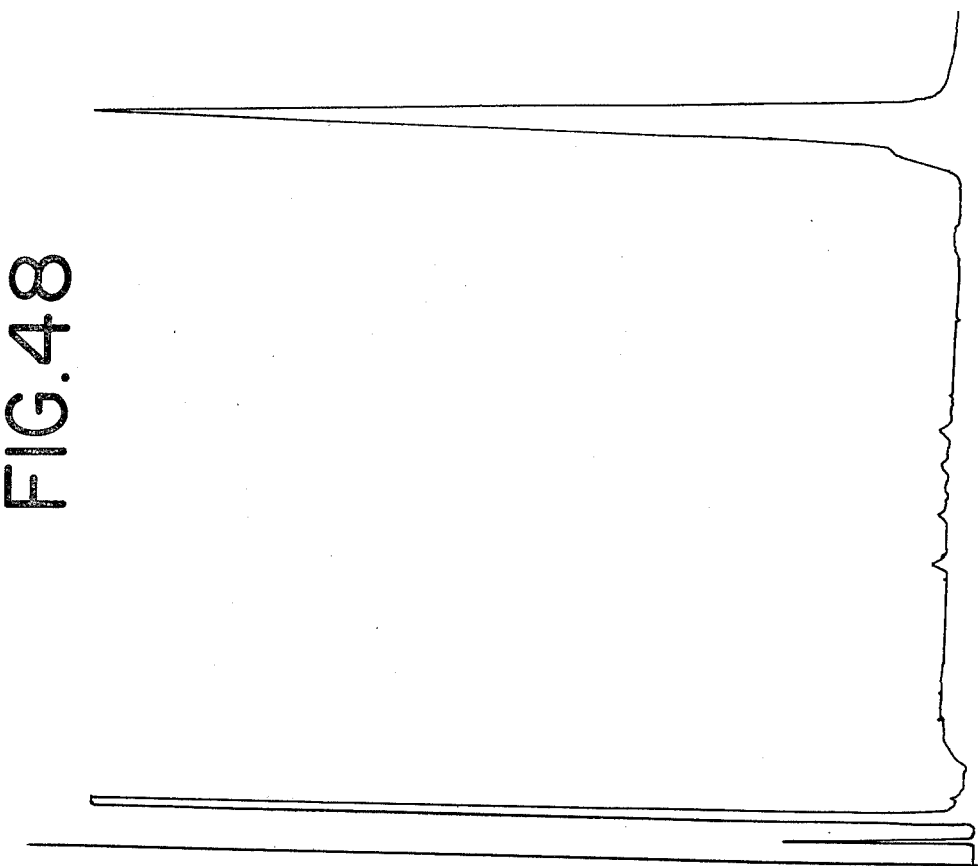

FIG. 48 is the GLC profile for the crude reaction product after initial workup of Example XII containing the compound having the structure:

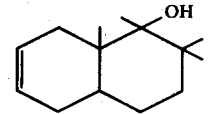

FIG. 49 is the mass spectrum for the reaction product of Example XII containing the compound having the structure:

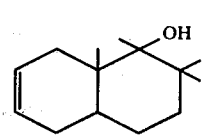

FIG. 50 is the NMR spectrum for fraction 6 of the distillation product of the reaction product of Example XII containing the compound having the structure:

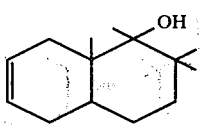

FIG. 51 is the infrared spectrum for fraction 6 of the distillation product of the reaction product of Example XII containing the compound having the structure:

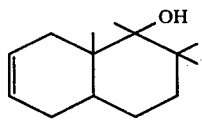

Figure 52:
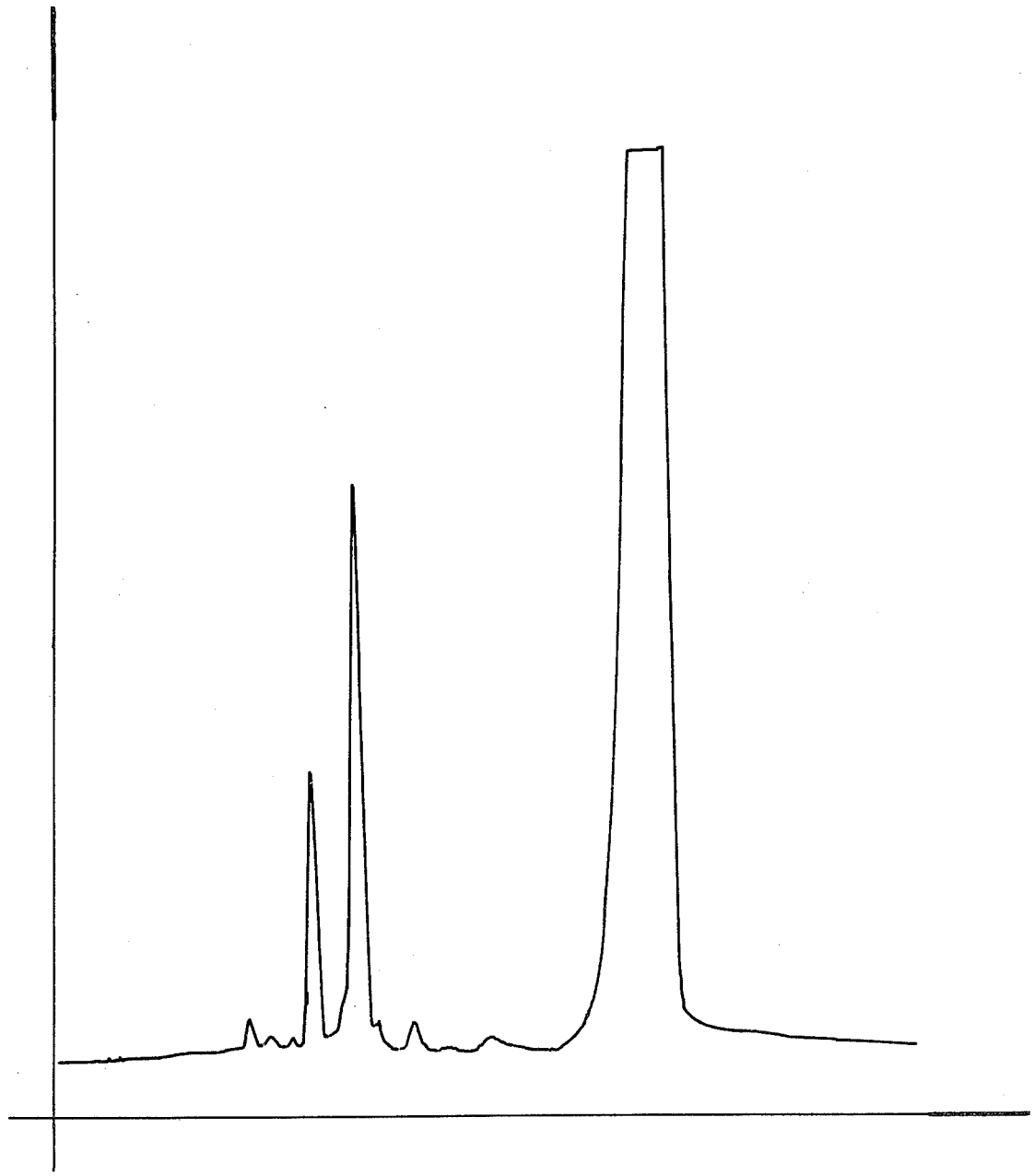

FIG. 52 is the GLC profile for fraction 2 of the one-plate distillation product of the reaction product of Example XIII containing the compounds having the structures:

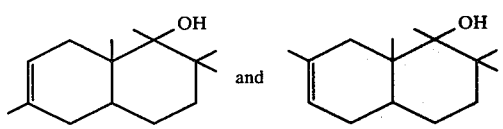

Figure 53:
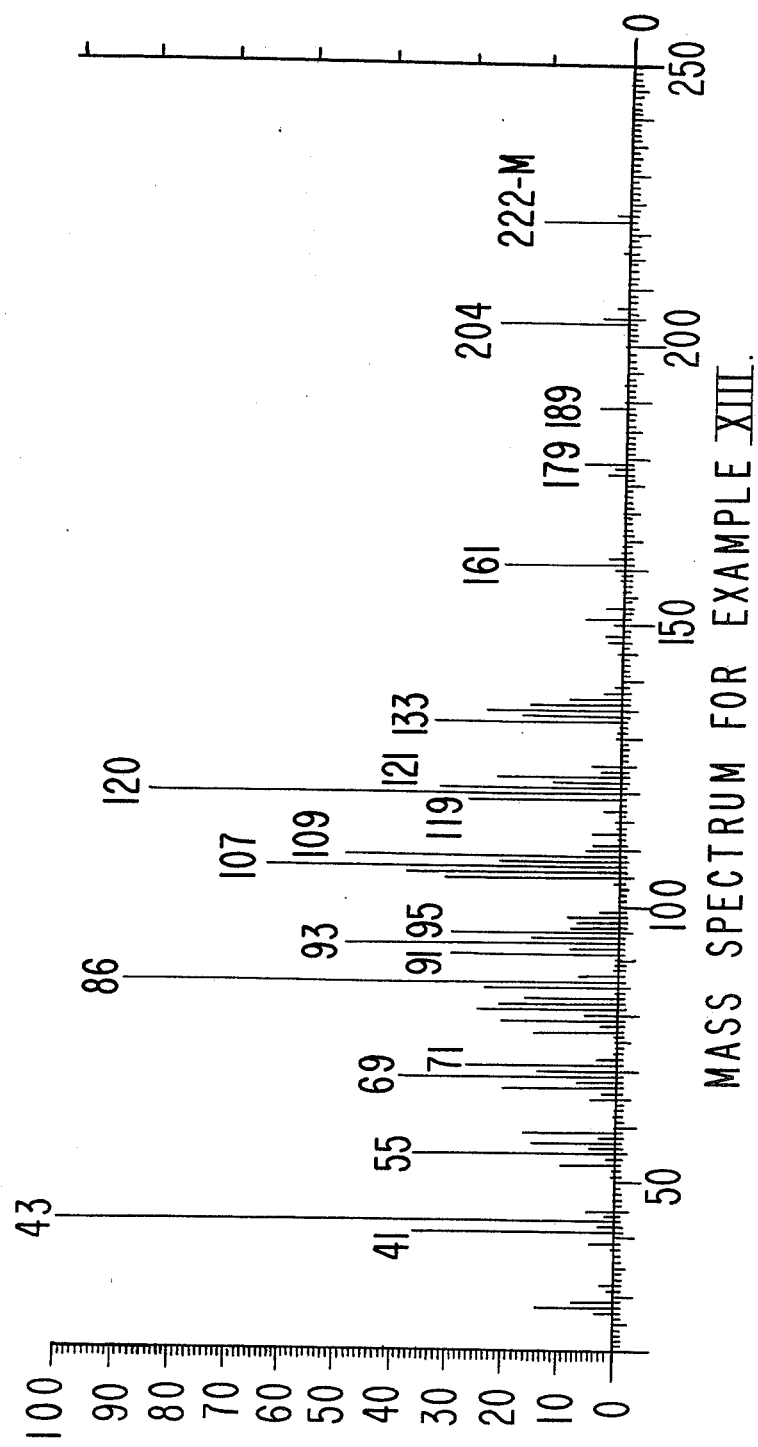

FIG. 53 is the mass spectrum for the reaction product of Example XIII containing the compounds having the structures:

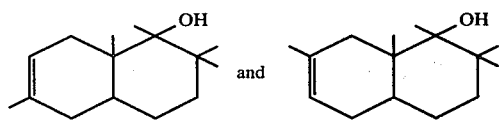

Figure 54:
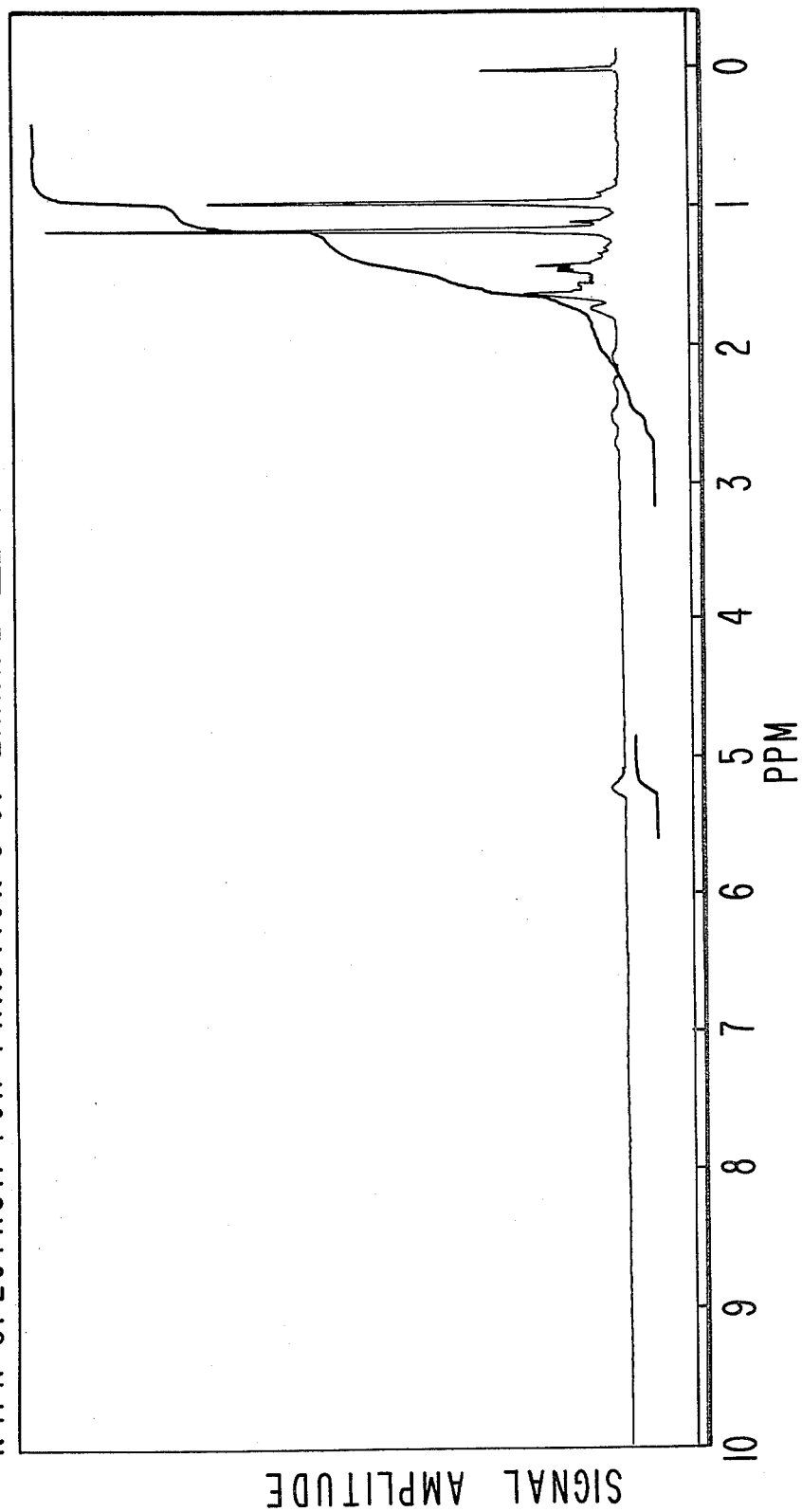

FIG. 54 is the NMR spectrum for fraction 6 of the distillation product of the reaction product of Example XIII containing the compounds having the structures:

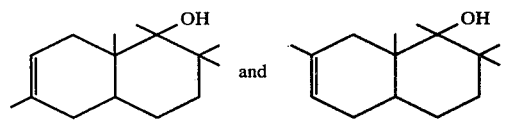

Figure 55:
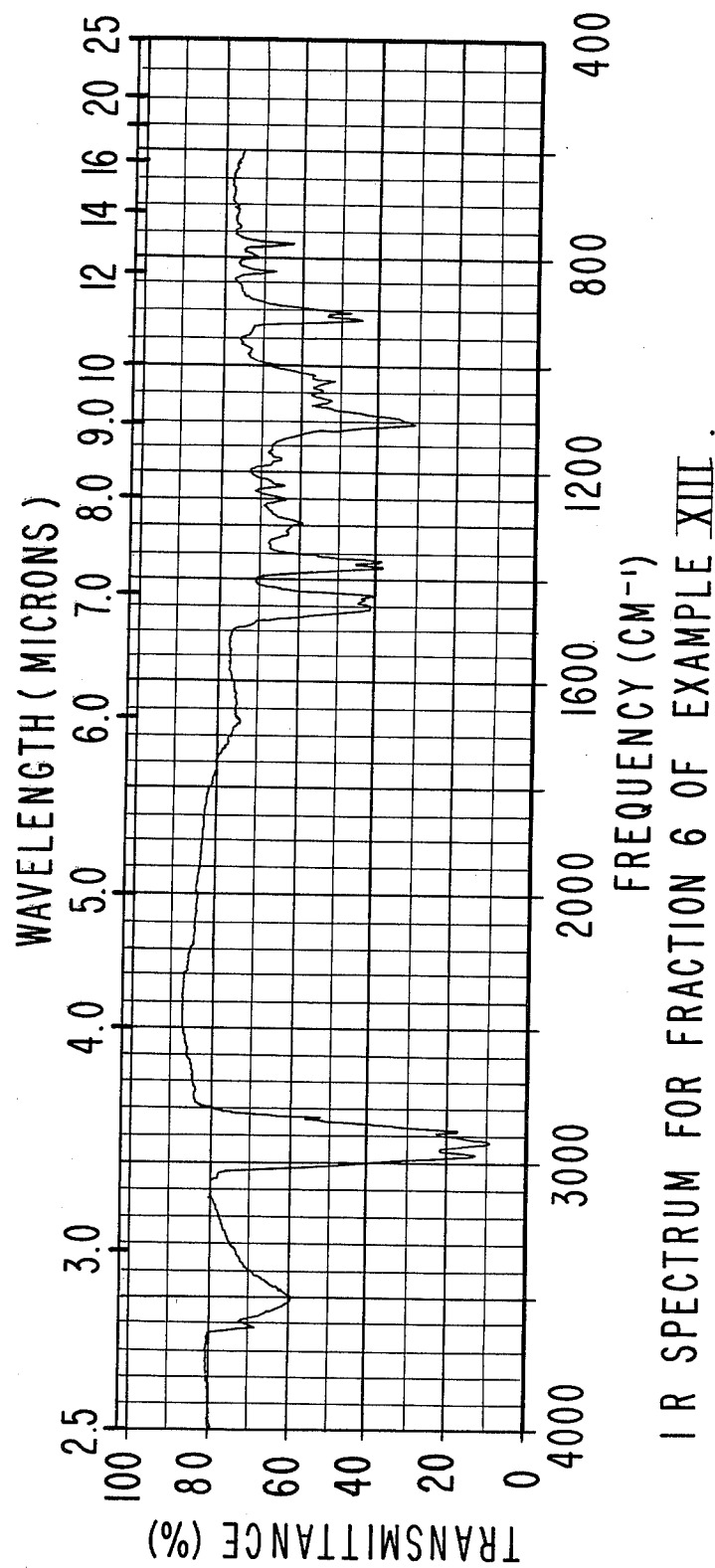

FIG. 55 is the infrared spectrum for fraction 6 of the distillation product of the reaction product of Example XIII containing the compounds having the structures:

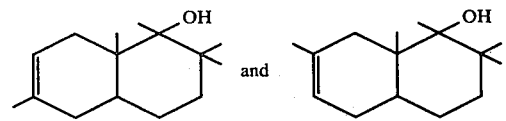

Figure 56:
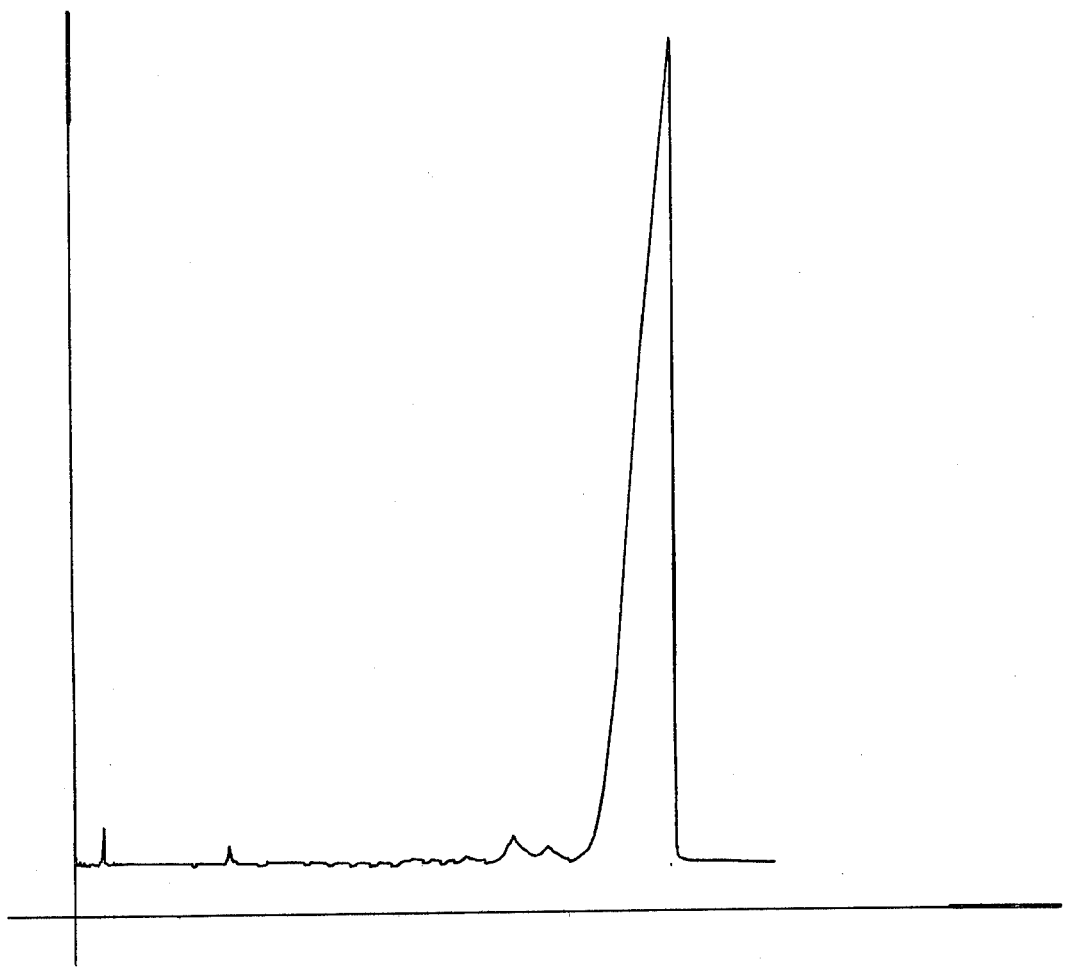

FIG. 56 is the GLC profile for fraction 3 of the distillation product of the reaction product of Example XIV containing the compounds having the structures:

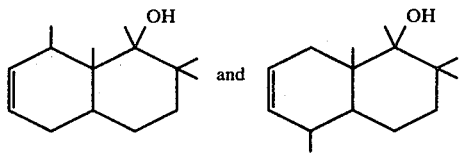

Figure 57:
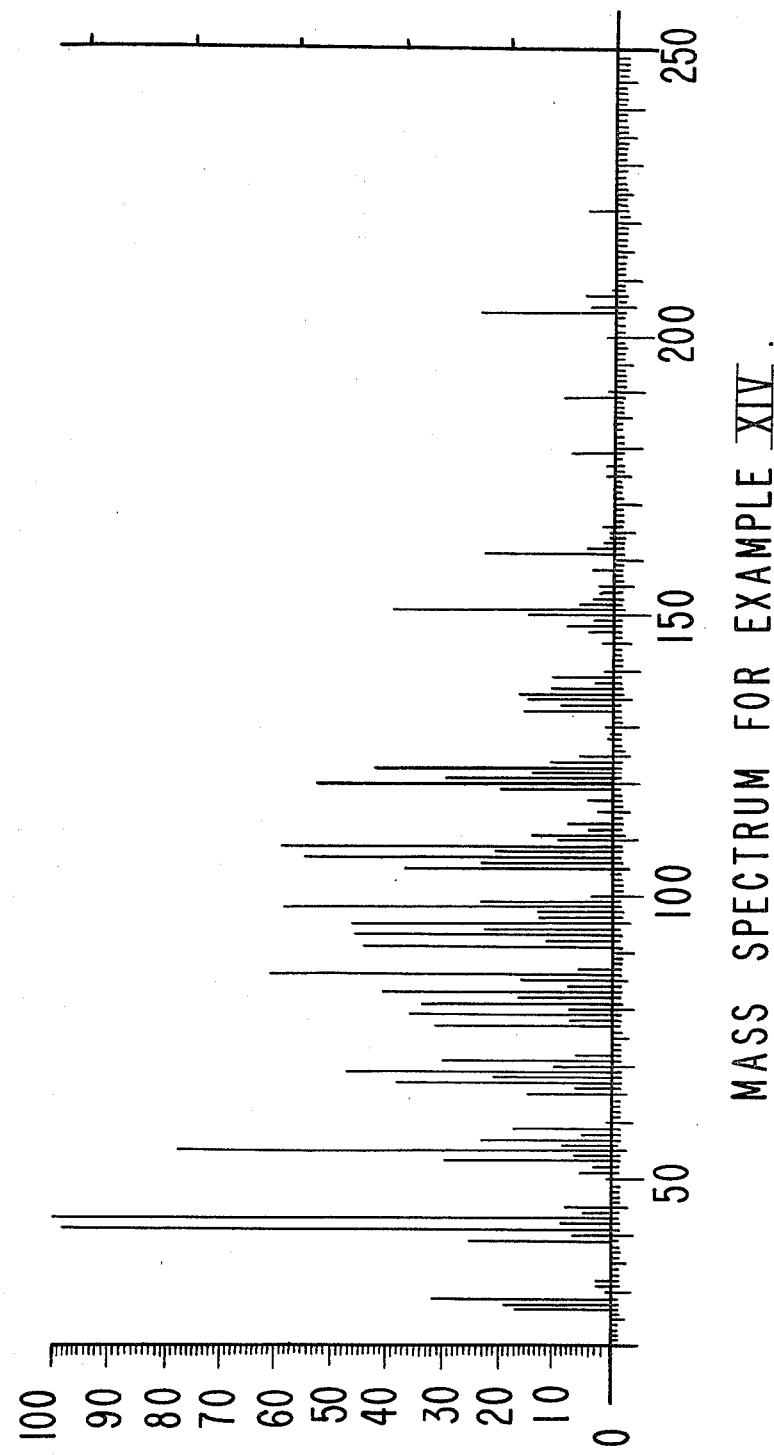

FIG. 57 is the mass spectrum for the reaction product of Example XIV containing the compounds having the structures:

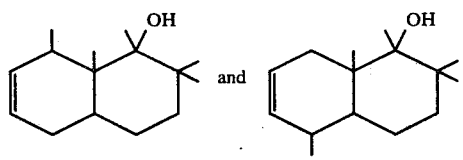

Figure 58:
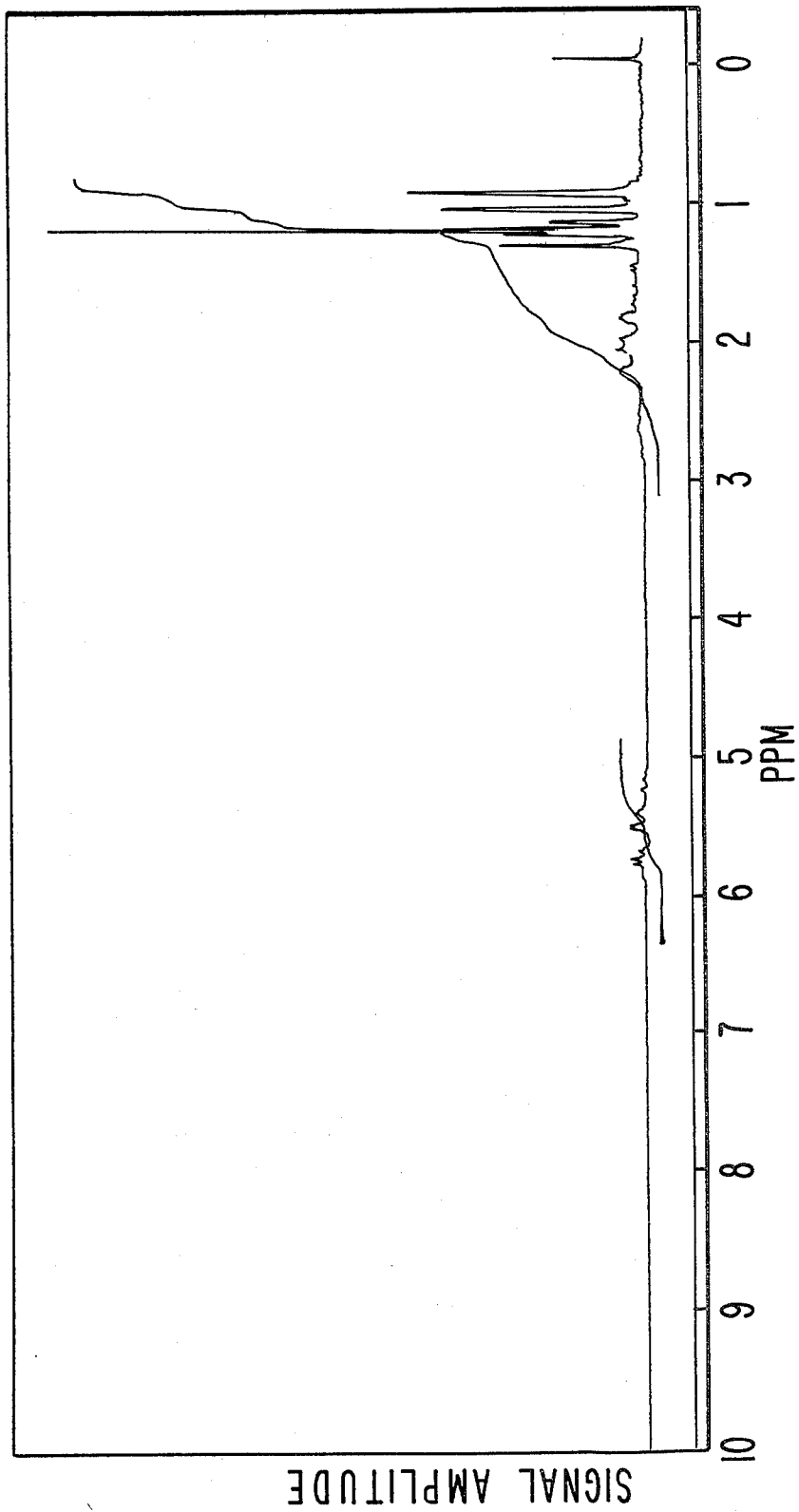

FIG. 58 is the NMR spectrum for fraction 4 of the distillation product of the reaction product of Example XIV containing the compounds having the structures:

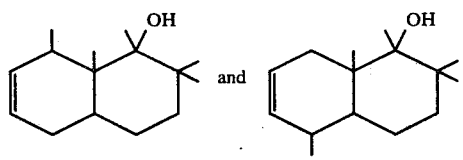

Figure 59:
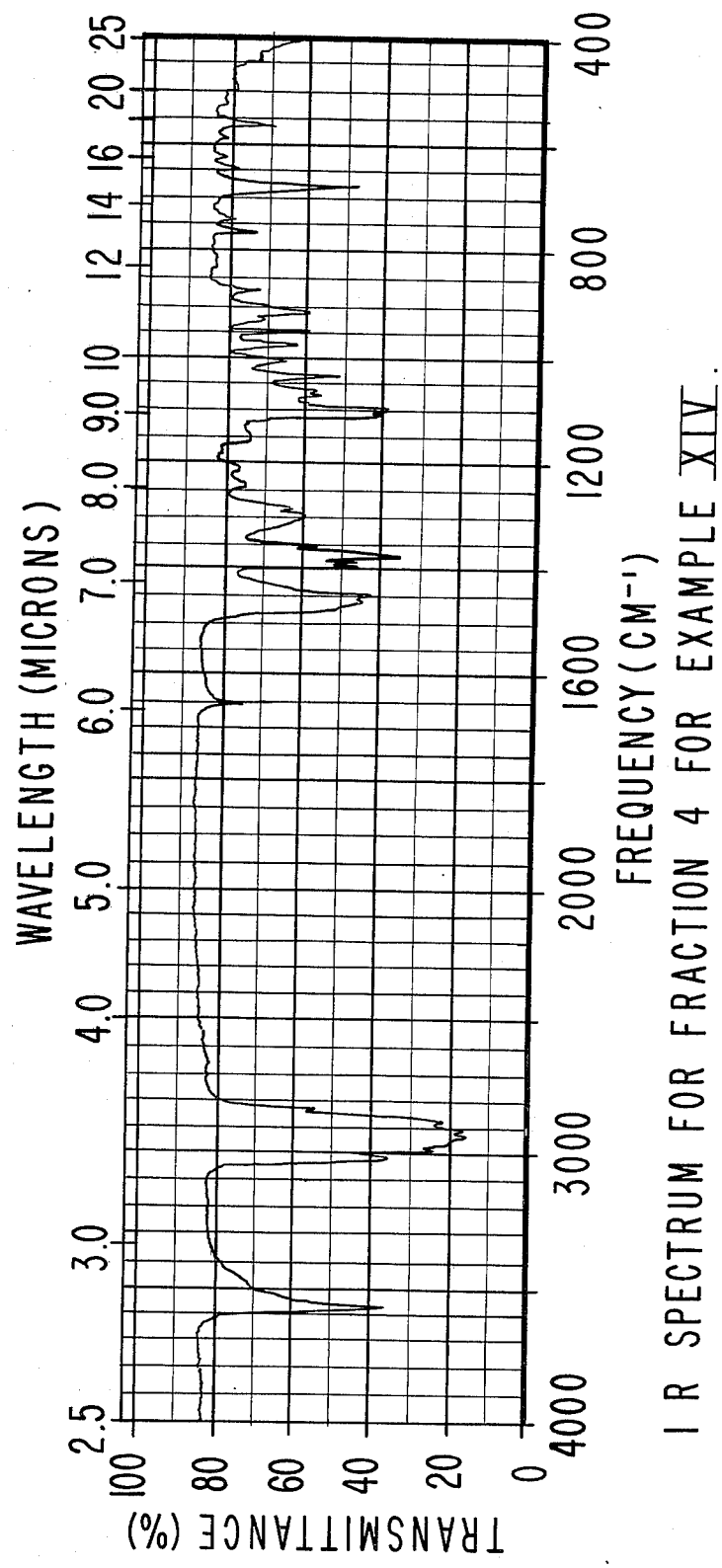

FIG. 59 is the infrared spectrum for fraction 4 of the distillation product of the reaction product of Example XIV containing the compounds having the structures:

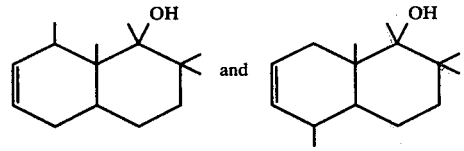

Figure 60:
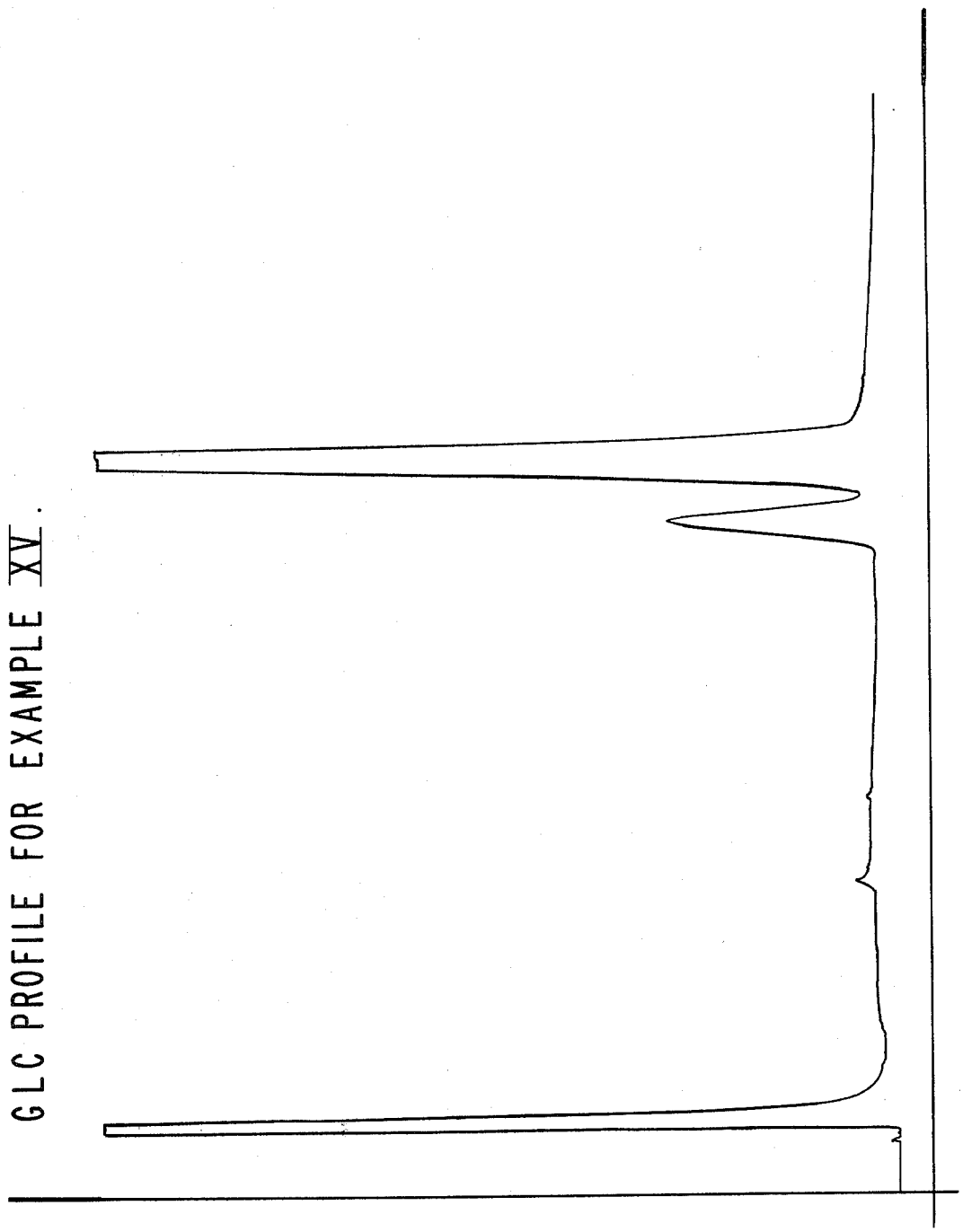

FIG. 60 is the GLC profile for the reaction product of Example XV containing the compound having the structure:

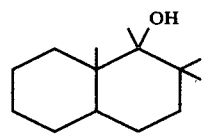

Figure 61:
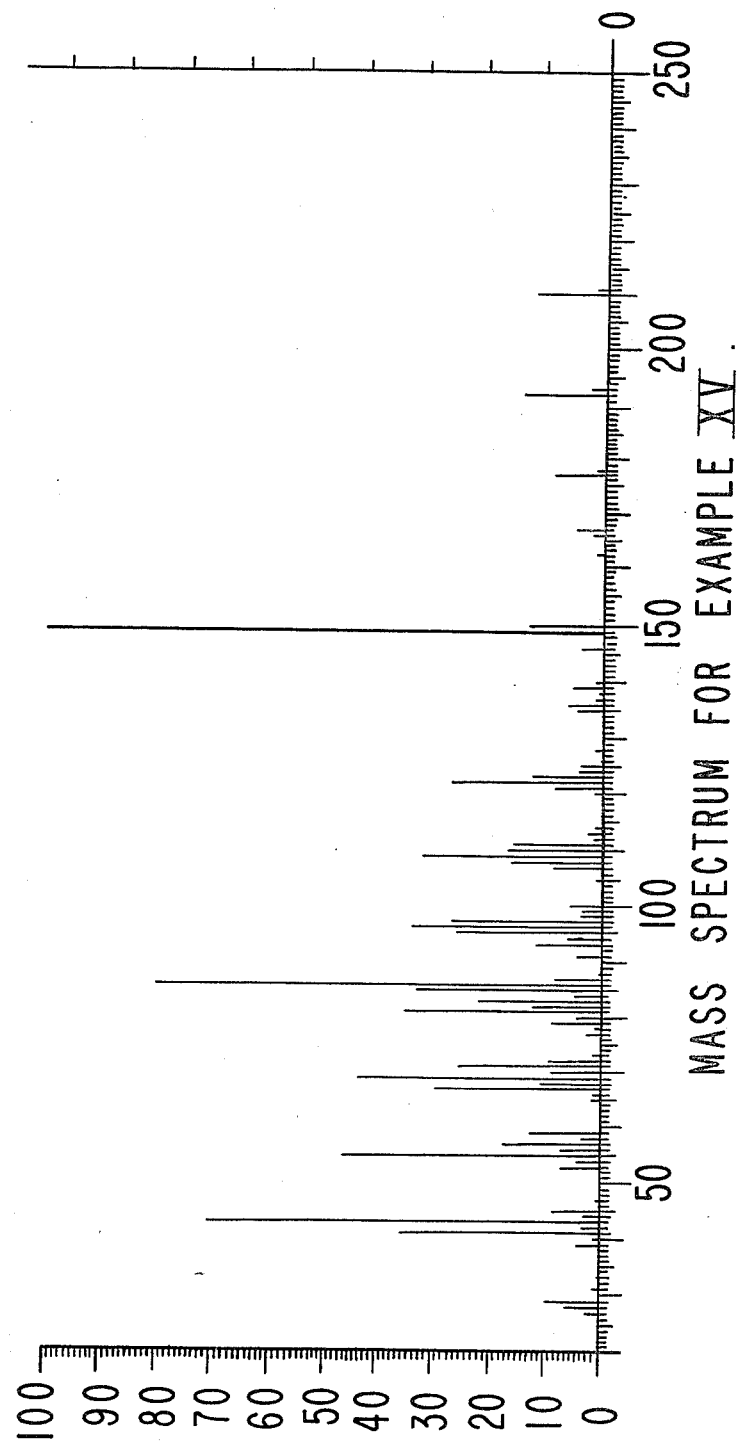

FIG. 61 is the mass spectrum for the reaction product of Example XV containing the compound having the structure:

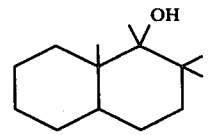

Figure 62:
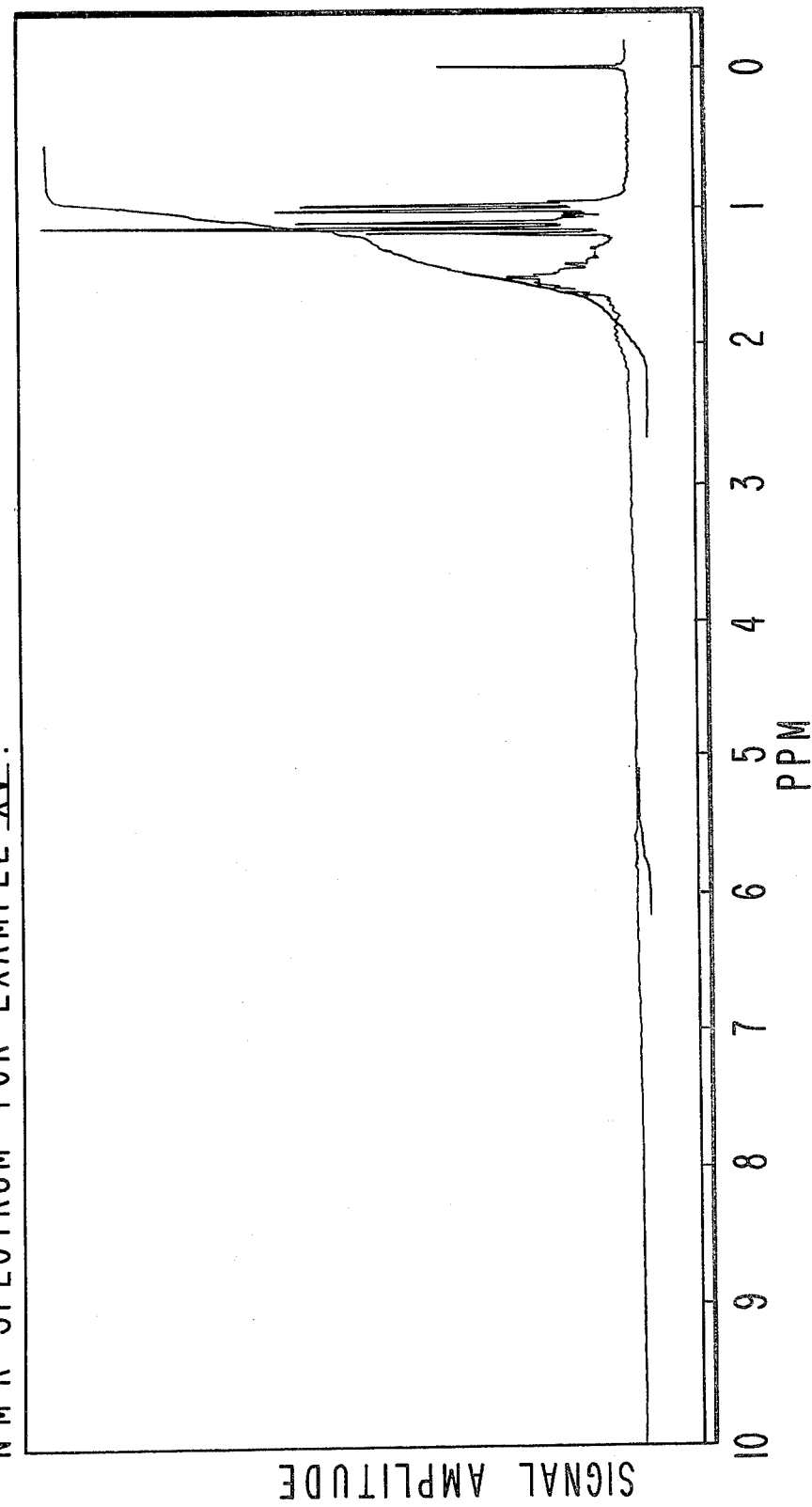

FIG. 62 is the NMR spectrum for the reaction product of Example XV containng the compound having the structure:

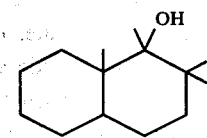

Figure 63:
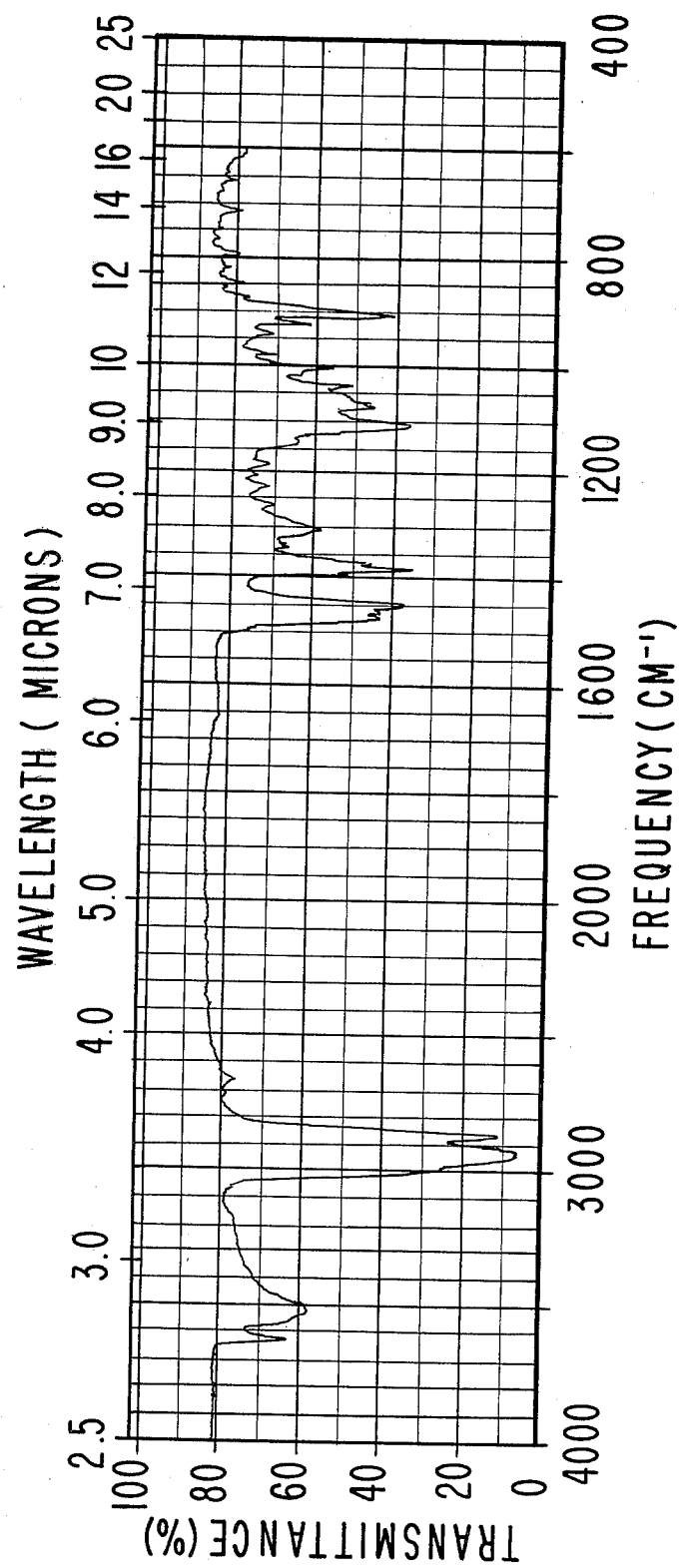

FIG. 63 is the infrared spectrum for the reaction product of Example XV containing the compound having the structure:

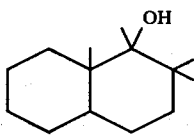

Figure 64:
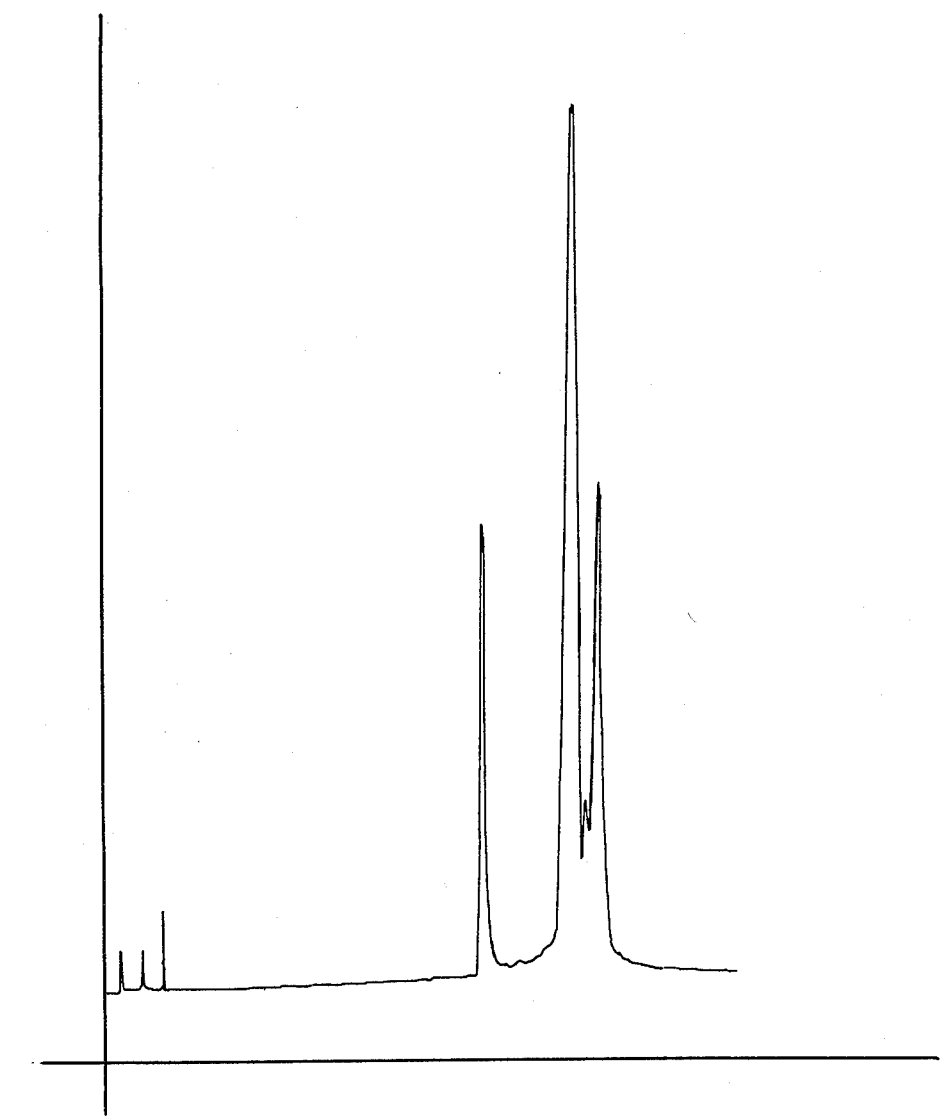

FIG. 64 is the GLC profile of the reaction product (after 8 hours reflux) for Example XVI containing the compounds having the structures:

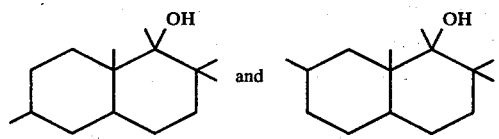

FIG. 65 is the mass spectrum for the reaction product of Example XVI containing the compounds having the structures:

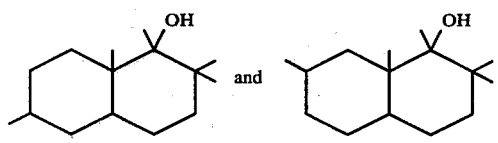

FIG. 66 is the NMR spectrum of fraction 4 of the distillation product of the reaction product of Example XVI containing the compounds having the structures:

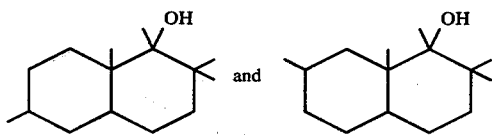

FIG. 67 is the infrared spectrum for fraction 4 of the distillation product of the reaction product of Example XVI containing the compounds having the structures:

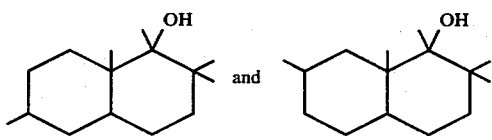

THE INVENTION

It has now been discovered that novel solid and liquid foodstuff, chewing gum, medicinal product and toothpaste compositions and flavoring compositions therefor having oriental, incense-like, peppery, blueberry-like, eucalyptol-like, minty, campohoraceous, floral, musk-like, rose-like, black pepper, spicey, patchouli, cooling, sandalwood-like, woody and walnut-like aromas with oriental, black pepper-like, peppery, minty, eucalyptol-like, camphoraceous, floral, rosey and patchouli-like tastes; as well as novel smoking tobacco and smoking tobacco flavoring compositions having sweet, fruity, berry-like, cooling, woody and floral aromas prior to smoking and on smoking in both the mainstream and the sidestream; as well as novel perfume compositions, colognes and perfumed articles (e.g. solid or liquid anionic, cationic, nonionic and zwitterionic detergents, fabric softener compositions, cosmetic powders and prior-added fabric softener articles) having intense and pleasant minty, camphoraceous, dry woody, sweet fruity, patchouli, woody patchouli, green, herbaceous, basil-like, citrus-like, bergamot-like, lime-like, grapefruit-like, peppery, precious woody, vetiver, fresh, musky, lavender, thyme, rosemary, sweaty, rooty and earthy aromas with floral, citrus, lavender, and amber-like top-notes and undertones may be provided by the utilization of one or more methyl substituted oxobicyclo-4,4,0-decane derivatives of our invention having the generic structure:

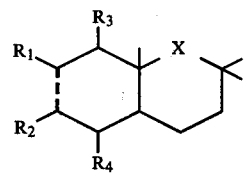

wherein X is a moiety which is either:

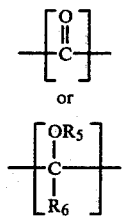

wherein the dashed line represents a carbon-carbon single bond or a carbon-carbon double bond; wherein $R_1$, $R_2$, $R_3$ and $R_4$ represent hydrogen or methyl with the provisos (i) that at least three of $R_1$, $R_2$, $R_3$ and $R_4$ represent hydrogen and the other of $R_1$, $R_2$, $R_3$ and $R_4$ is methyl and (ii) that when the dashed line is a carbon-carbon single bond and X is the moiety:

then one of $R_1$, $R_2$, $R_3$ or $R_4$ is methyl and the other of $R_1$, $R_2$, $R_3$ or $R_4$ is hydrogen; wherein $R_5$ represents hydrogen and $R_6$ represents hydrogen or methyl in foodstuffs, chewing gums, toothpasts, medicinal products, perfume compositions, perfumed articles, colognes and smoking tobaccos as well as smoking tobacco substitutes.

Unless otherwise specified, representations herein of organic structures are intended to indicate a "cis" isomer a "trans" isomer, or a mixture of "cis" and "trans" isomers with respect to the plane of the cyclohexane ring. Thus, the generic structure:

may either be a "cis" isomer, for example, having the structure:

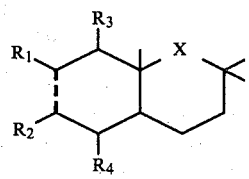

or a "trans" isomer having the structure:

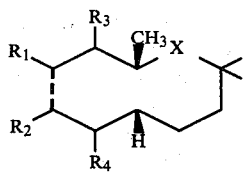

Furthermore, the "trans" structure:

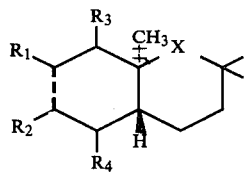

with respect to the methyl moiety at the "-9, 10-" position may further be specified, for example, by the structure:

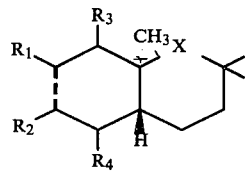

wherein X is >CHOH.

The methyl substituted oxobicyclo-4,4,0-decane derivatives of our invention may be prepared by first reacting 2,6,6-trimethylcyclohex-2-enone with a substituted butadiene such as butadiene, isoprene or piperylene according to the reaction:

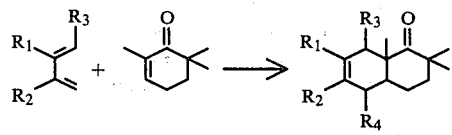

The ratio of diene:ketone may be in the range of from about 1:1 (mole ratio) up to about 10:1 with a mole ratio of diene:ketone preferably being about 1.5:1. The reaction may be carried out in the presence of a Lewis acid catalyst such as aluminum thrichloride, zinc chloride, titanium tetrachloride, BF$_3$.etherate, ethyl aluminum dichloride, diethyl aluminum chloride, and other Lewis acid catalysts. Reaction may be carried out in the presence of or in the absence of a solvent. When using a solvent, solvents such as toluene, xylene and chlorinated solvents may be used which are inert to the reactants.

The reaction may be carried out at the temperatures of between $-15°$ C. and $100°$ C.; preferably at $-10°$ C. up to about $50°$ C. The reaction may be carried out at atmospheric pressure, super atmospheric pressures and subatmospheric pressures. Most conveniently, economically and preferably the reaction is carried out at atmospheric pressure.

The resulting ketone may be used as is for its organoleptic properties, in which case, the resulting ketone is purified as by standard extraction and fractional distillation processes. The isomers resulting may be commerically separated as by means of high pressure liquid chrometography.

The resulting ketone may, however, be further reacted either (i) by means of a reduction reaction to form a saturated ketone according to the reaction:

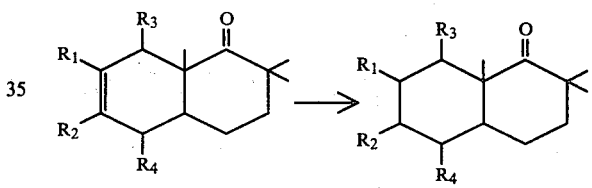

or (ii) by reduction of the ketone moiety to form an alcohol by means of the reaction:

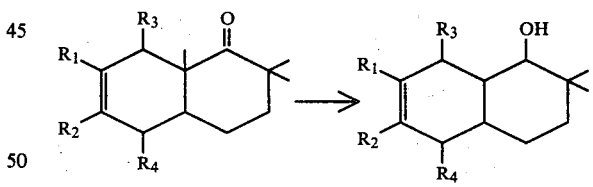

or (iii) by means of reaction with an organometallic compound such as a Grignard reagent followed by subsequent hydrolysis whereby the 1-methyl-1-hydroxy derivative is formed according to the reaction scheme:

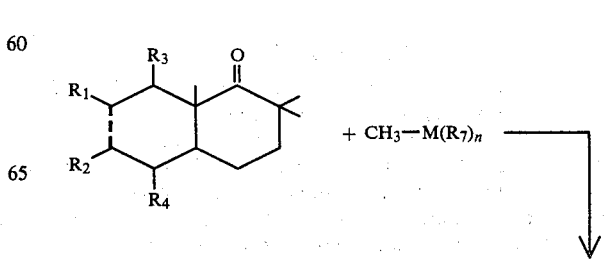

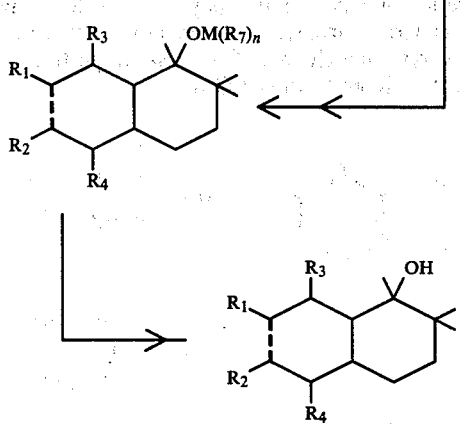

wherein M is either of MgX, Na, K, Li, Cd, Mg or Zn; wherein X is chloro, bromo or iodo; wherein $R_7$ is lower alkyl; wherein when M is Cd, Mg or Zn, $N=1$ and when m is MgX, Na, K or Li, $n=0$.

The resulting unsaturated alcohol may further be reduced as by hydrogenation, for example, according to the reaction:

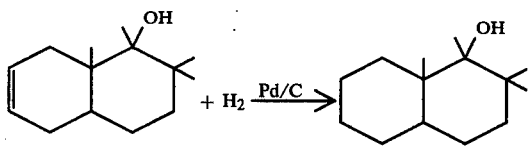

When a hydrogenation reaction is carried out, e.g.:

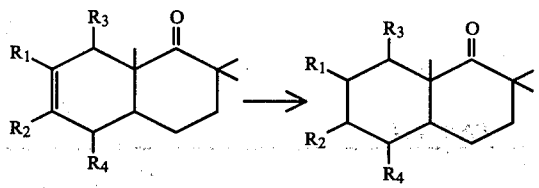

a hydrogenation catalyst is used, for example, a palladium catalyst or a palladium-on-carbon catalyst whereby a saturated ketone is formed. The hydrogenation is preferably carried out at temperatures in the range of from about 20° C. up to about 100° C. at pressures of between about 30 psig and about 300 psig; preferably at pressures of between 40 psig and 60 psig. At the end of the hydrogenation, the resulting ketone may be used for its organoleptic properties in which case the resulting ketone is purified by means of standard extraction procedures and standard fractional distillation procedures. In the event that two or more isomers are formed as a result of the reaction, the resulting isomers may be separated as by means of fractional distillation or even by means of high pressure liquid chomotography.

When the ketone moiety is reduced to the alcohol as by means of the reaction:

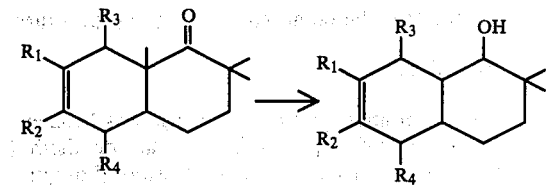

this reaction takes place using a reducing agent such as lithium aluminum hydride, sodium boro hydride, lithium borohydride. Al(isobutyl)$_2$H or "Vitride ®" which is NaAlH$_2$(OCH$_2$CH$_2$OCH$_3$)$_2$. However, the ketone moiety may be reduced to the alcohol moiety by means of high pressure and high temperature hydrogenation, e.g. carrying out a hydrogenation at about 90°-150° C. at pressure of between 50 and 5,000 psig. The higher pressure and higher temperature range will give rise to shorter reaction time.

The resulting ketone may be used as is or may be further reacted with an organometallic compound which is subsequently hydrolyzed. Thus, in the resulting ketone is to be used "as is" for its organoleptic properties, said ketone will be further "workup" as by means of standard extraction procedures and/or fractional distillation procedures. In the event that pure isomers are desired and indeed pure stereoisomers are desired, high pressure liquid chromotographic techniques may be used as well as standard stereoisomer-separation techniques using pure stereoisomers which will react with a functional group followed by decomposition after fractional crystallization, for example.

When the resulting ketone is reacted with an organometallic compound to form a second organometallic compound which is subsequently hydrolized according to the reaction procedure:

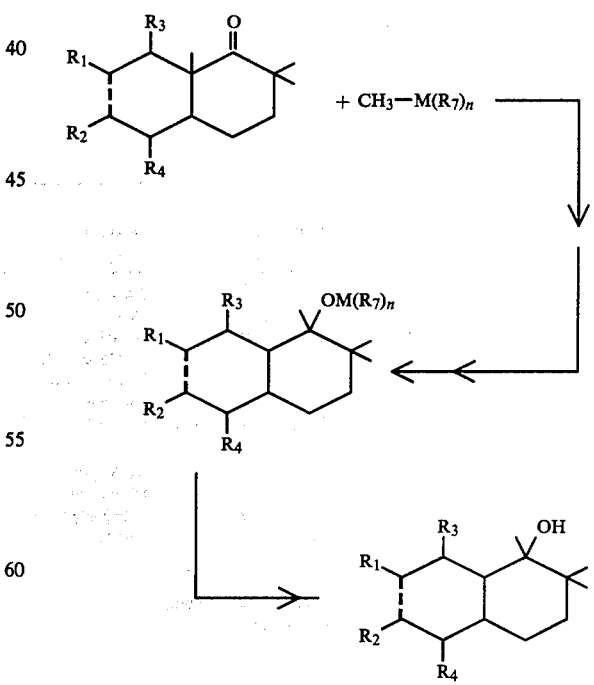

In the reaction of the oxabicyclic ketone with the organometallic compound having the structure:

CH₃—M(R₇)ₙ it is preferred that the compound having the structure:

CH₃—M(R₇)ₙ be reacted in an appropriate solvent such as benzene, benzene/tetrahydrofuran, tetrahydrofuran or diethyl ether. It is also preferred that the mole ratio of organometallic compound having the structure:

CH₃—M(R₇)ₙ:Ketone be about 1:1. It is further preferred that the reaction temperature be from about −5° C. up to about 40° C. with the most preferred temperature being 20° C.-30° C.

The hydrolysis of the organometallic compound to form the resulting alcohol is carried out using a mineral acid such as dilute aqueous hydrochloric acid, sulfuric acid or phosphoric acid or other protonic acids such as paratoluenesulfonic acid. The hydrolysis preferably takes place at 0°–20° C. At the end of this reaction, the reaction product is isolated by means of standard isolation techniques such as fractional distillation and, if desired, preparative GLC or high pressure GLC for isolation of the end product.

An alternative method for preparing unsaturated alcohols of our invention is to react the ketones resulting from the Diels-Alder reaction with isopropyl magnisium halide. In view of the sterically hindered position of the ketone (as a result of the methyl groups "alpha" to the ketone moity), an oxygrignard is formed from the ketone without alkylation at the ketone moity. The resulting oxygrignard may then be hydrolized using standard hydrolisis conditions as set forth above to yield the resulting alcohol. The reaction illustrating this procedure is set forth as follows:

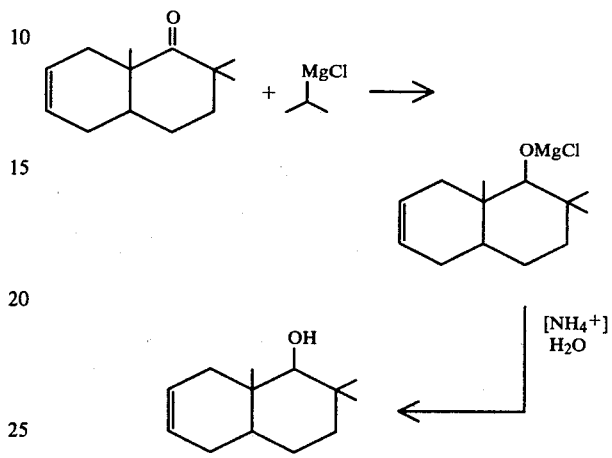

Specific examples of compounds produced according to the foregoing process are set forth in Table I below:

TABLE I

| Structure of Compound | Name of Compound | Perfumery Evaluation | Flavor Evaluation | Smoking Tobacco Evaluation |
|---|---|---|---|---|
| Produced according to Example I | 3,4,4A,5,8,8A-Hexahydro-2,2,8A-trimethyl-1(2H)-naphthalenone (majority: "cis" isomer). | Minty, camphoraceous, dry woody with floral citrus background. | An oriental incense, peppery aroma with an oriental and peppery flavor characteristic at 1 ppm. | |
| Produced according to Example II | Octahydro-2,2,8A-trimethyl-1(2H)-naphthalenone. | A sweet, fruity, minty camphoraceous aroma with a woody patchouli undertone flavor characteristic. | A blueberry-like, oriental, minty, camphoraceous, eucalyptol-like aroma character with a camphoraceous, oriental, minty, eucalyptol flavor characteristic at 2 ppm making it useful for oral hygiene and cough drops flavors. | A sweet, woody, citrusy aroma with cooling nuances prior to and on smoking in the mainstream and in the sidestream. |

TABLE I-continued

| Structure of Compound | Name of Compound | Perfumery Evaluation | Flavor Evaluation | Smoking Tobacco Evaluation |
|---|---|---|---|---|
| Mixture of: [structure with C=O] and [structure with C=O] Produced according to Example III | 3,4,4A,5,8,8A-Hexahydro-2,2,5,6(and 7),8A-tetramethyl-1(2H)-naphthalenone (majority: "cis" isomer). | A green, herbaceous aroma with a lavender top-note and a basil/citrus undertone with bergamot-like nuances. | A sweet, floral, musk-like, fresh rosey aroma with a floral rosey flavor characteristic at 0.2 ppm, causing it to be useful in rose and raspberry flavors. | |
| Mixture of compounds having the structures: [structure with C=O] and [structure with C=O] produced according to Example IV | Octahydro-2,2,6(and 7),8A tetramethyl-1(2H)-naphthalenone (Majority: "cis" isomer). | A peppery dry woody aroma with a precious woody background and vetiver-like and ambery nuances. | An oriental black pepper-like, spicey aroma with a black pepper flavor characteristic at 1 ppm, causing it to be useful in black pepper flavors. | |
| Mixture of compounds having the structures: [structure with OH] and [structure with OH] produced according to Example V | 1,2,3,4,4A,5,8,8A-Octahydro-2,2,6(& 7),8A-tetrahydro-1-naphthol (Majority: "cis" isomer). | A citrus (lime) aroma with dry woody and patchouli undertones. | A citrus, fresh, musky, floral aroma with a perfumery flavor characteristics at 0.1 ppm. | |

TABLE I-continued

| Structure of Compound | Name of Compound | Perfumery Evaluation | Flavor Evaluation | Smoking Tobacco Evaluation |
|---|---|---|---|---|
| Mixture of compounds having the structures: 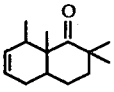 and 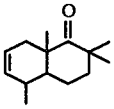<br><br>Produced according to either of Examples VI(A) or VI(B) | 3,4,4A,5,8,8A-Hexahydro-2,2,8(and 5),8A-tetramethyl-1(2H)-naphthalenone (Majority: "cis isomer). | A rich herbaceous, lavender, thyme/rosemary aroma which becomes sweaty on dry out. | A floral, oriental, patchouli-like, camphoraceous, incense-like aroma characteristic with an oriental, patchouli, camphoraceous flavor profile at 2 ppm. | A sweet, fruity, berry, cooling, woody, floral aroma both prior to and on smoking in the main steam and in the side stream. |
| 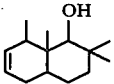<br><br>Produced according to Example VII(A) or VII(B) | 1,2,3,4,4A,5,8,8A-Octahydro-2,2,8A-trimethyl-1-naphthol. | A patchouli, woody, camphoraceous aroma with a borneol-like undertone. | A patchouli, camphoraceous, earthy aroma characteristic with a patchouli, camphoraceous, earthy flavor characteristic at 1 ppm. | A sweet, woody, vetiver-like aroma and taste, both prior to and on smoking in the mainstream and the sidestream. |
| Mixture of compounds having the structures: 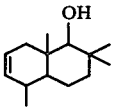 and<br><br>Produced according to Example VIII | 1,2,3,4,4A,5,8,8A-Octahydro-2,2,8 (and 5), 8A-tetramethyl-1-naphthol. | An intense patchouli-like aroma with a woody background. | An oriental ionone-like, minty, eucalyptus, cooling aroma with an oriental flavor characteristic at 1 ppm | A woody, patchouli-like, oriental-like aroma both to and on smoking causing virginia-like tobacco to attain a turkish tobacco aroma and taste |

TABLE I-continued

| Structure of Compound | Name of Compound | Perfumery Evaluation | Flavor Evaluation | Smoking Tobacco Evaluation |
|---|---|---|---|---|
| Mixture of compounds having the structures: [OH structure] and [OH structure] Produced according to Example IX | 2,2,6(and 7), 8A-tetramethyl-1-naphthol | Sandalwood, patchouli-like aroma with incense-like undertones. | A sandalwood, patchouli, incense, ionoe and eucalyptol aroma character with incense flavor characteristics at 1 ppm. | |
| [OH structure] Produced according to Example X | Decahydro-2,2,8A-trimethyl-1-naphthol | An earthy, camphoraceous, woody, borneol-like, patchouli aroma with precious, woody undertones. | A minty, eucalyptol-like, woody aroma characteristic with minty eucalyptol-like, woody and bitter flavor characteristics at 0.1 ppm causing it to be useful for oral hygiene flavors. | |
| Mixture of compounds having the structures: [O structure] and [O structure] Produced according to Example XI | Octahydro-2,2,8,8A-tetramethyl-1(2H)-naphthalenone | An earthy, camphoraceous, woody, borneol-like, patchouli aroma with precious, woody undertones | A minty, eucalyptol-like woody aroma characteristic with minty eucalyptol-like, woody and bitter flavor characteristics at 0.1 ppm causing it to be useful for oral hygiene flavors. | A sweet, woody aroma and taste both prior to and on smoking. |
| [OH structure] Produced according to Example XII | 1,2,3,4,4A,5,8,8A-Octahydro-1,2,2,8A-tetramethyl-1-naphthol. | A camphoraceous/borneol, earthy, rooty, woody aroma with a patchouli background. | An earthy, patchouli, oriental, walnut-like aroma with an earthy patchouli oriental walnut flavor characteristic causing it to be useful in walnut flavors, at a concentration of 0.002 ppm | A sweet, woody, vetiver-like aroma and taste both prior to and on smoking in the mainsteam and the sidestream. |

TABLE I-continued

| Structure of Compound | Name of Compound | Perfumery Evaluation | Flavor Evaluation | Smoking Tobacco Evaluation |
|---|---|---|---|---|
| Mixture of compounds having the structures: 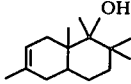 and 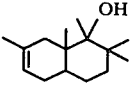 produced according to Example XIII | 1,2,3,4,4A,5,8, 8A-Octahydro-1, 2,2,6(and 7), 8A-pentamethyl- 1-naphthol (Majority: "cis" isomer). | A dry woody, rooty, patchouli aroma with camphoraceous and borneol undertones. | A patchouli, oriental and earthy aroma characteristic with a patchouli earthy flavor characteristic making it useful for walnut flavors at 1 ppm | |
| Mixture of compounds having the structures: 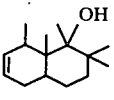 and 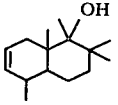 Produced according to Example XIV | 1,2,3,4,4A,5,8, 8A-Octahydro-1, 2,2,8(and 5), 8A-pentamethyl- 1-naphthol. | A patchouli aroma with minty topnotes. | An oriental, ionone-like, minty, eucalyptol-like, patchouli-like aroma with a patchouli-like flavor characteristic at 1 ppm | A woody, patchouli-like aroma and taste both prior to and on smoking yielding a cigar-type taste in the mainstream and the sidestream. |
|  Produced according to Example XV | Decahydro-1,2, 2,8A-tetra- methyl-1-naph- thol. | A patchouli aroma with minty topnotes. | An oriental ionone-like, minty, eucalyptol-like, patchouli-like aroma with a patchouli-like flavor characteristic at 1 ppm. | |

TABLE I-continued

| Structure of Compound | Name of Compound | Perfumery Evaluation | Flavor Evaluation | Smoking Tobacco Evaluation |
|---|---|---|---|---|
| Mixture of: 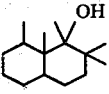 and 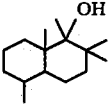<br><br>Prepared by reacting CH₃Li with product of Example XI | Decahydro-1,2,2,8(and 5),8A-pentamethyl-1-naphthol | | | A woody, camphoraceous, and patchuoli-like aroma and taste both prior to and on smoking with woody, oriental notes in the smoke flavor causing it to be useful in the production of Turkish tobacco flavor, this material imparts a Turkish tobacco aroma and taste nuance to Virginia tobaccos in both the mainstream and the sidestreams. |
| Mixture of compounds having the structures: 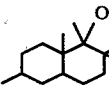 and 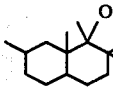<br><br>Prepared according to Example XVI | Decahydro-1,2,2,6(and 7),8A-pentamethyl-1-naphthol. | An earthy, camphoreceous aroma with patchouli background. | A patchouli, camphoraceous aroma and flavor profile at 2 ppm. | A woody, patchouli-like aroma and taste both prior to and on smoking. |

When the methyl substituted oxobicyclo-4,4,0-decane derivatives of our invention are used as food flavor adjuvants, the nature of the co-ingredients included with each of the said methyl substituted oxobicyclo-4,4,0-decane derivatives in formulating the product composition will also serve to alter, modify, augment or enhance the organoleptic characteristics of the ultimate foodstuff treated therewith.

As used herein in regard to flavors, the terms "alter", "modify" and "augment" in their various forms means "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs, include soups, convenience foods, beverages, dairy products, candies, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to means a composition which comprises a substantially water-insoluble, chewable plastic gum base such chicle, or substitutes therefor, including jelutong, guttakay, rubber or certain comestible natural or synthetic resins or waxes. Incorporated with the gum base in admixture therewith may be plasticizers or softening agents, e.g., glycerine; and a flavoring composition which incorporates one or more of the methyl substituted oxobicyclo-4,4,0-decane derivatives of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxytoluene (2,6-di-tertiary-butyl-4-methylphenol), propyl gallate and the like and sequestrants, e.g., citric acid.

Thickener compounds include carriers, binders, protective colloids, suspending agents emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectines, and emulsifiers, e.g., mono- and diglycerides of fatty acids, skim milk powder, hexoses, pentoses, disaccharides, e.g., sucrose corn syrup and the like.

Surface active agents includes emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g. benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anticaking agents, e.g., aluminum calcium sulfate and tribasic calsium phosphate; enzymes; yeast foods, e.g., calcium lactate and caldium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methylbutyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol acrolein, n-butanal, crotonal, diacetyl, 2-methylbutanal, beta,-beta-dimethylacrolein, methyl n-amyl ketone, n-hexanal, 2-hexenal, isopentanal, hydrocinnamic aldehyde, cis-3-hexenal, 2-heptenal, nonyl aldehyde, 4-(p-hydroxyphenyl)-2-butanone, alpha-ionone, beta-ionone, 2-methyl-3-butanone, benzaldehyde, damascone, α-damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methylfurfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpin hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl carpylate, ethyl cinnamate, ethyl crotonate, ethyl formate, ethyl isobutyrate, ethyl isovalerate, ethyl laurate, ethyl myristate, ethyl alphamethylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyldiphenyl, methyl naphthalene, myrcene, naphthalene, octadecane, tetradecane, tetramethylnaphthalene, tridecane, trimethylnaphthalene, undecane, caryophyllene, α-phellandrene, β-phellandrene, p-cymene 1-alpha-pinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils such as jasmine absolute, cassia oil, cinnamon bark oil, black pepper oleoresin, oil of black pepper, rose absolute, orris absolute, oil of cubeb, oil of coriander, oil of pimento leaf, oil of patchouli, oil of nutmeg, lemon essential oil, safran oil, Bulgarian rose, capsicum, yara yara and vanilla; lactones such as γ-nonalactone; sulfides, e.g., methyl sulfide and other materials such as maltol, and acetal (e.g., 1,1-diethoxyethane, 1,1-dimethoxyethane and dimethoxymethane), piperine, chavicine, and piperidine.

The specific flavoring adjuvant selected for use may be either solid or liquid depending upon the desired physical form of the ultimate product, i.e., foodstuff, whether simulated or natural, and should, in any event, (i) be organoleptically compatible with the methyl substituted oxobicyclo-4,4,0-decane derivatives of our invention by not covering or spoiling the organoleptic properties (aroma and/or taste) thereof; (ii) be non-reactive with the methyl substituted oxobicyclo-4,4,0-decane derivatives of our invention and (iii) be capable of providing an environment in which the methyl substituted oxobicyclo-4,4,0-decane derivatives can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of methyl substituted oxobicyclo-4,4,0-decane derivatives employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se, chewing gum, per se, medicinal product per se, toothpaste per se, or flavoring composition.

The use of insufficient quantities of methyl substituted oxobicyclo-4,4,0-decane derivatives will, of course, substantially vitiate any possibility of obtaining the desired results while excess quantities prove needlessly costly and, in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of methyl substituted oxobicyclo-4,4,0-decane derivatives ranging from a small but effective amount, e.g., 0.01 parts per million up to about 100 parts per million based on total composition are suitable. Concentrations in excess of the maximum quantity stated are not normally recommended, since they fail to prove commensurate enhancement of organoleptic properties. In those instances, wherein the methyl substituted oxobicyclo-4,4,0-decane derivatives are added to the foodstuff as an integral component of a flavoring composition, it is, of course, essential that the total quantity of flavoring composition employed be sufficient to yield an effective methyl substituted oxobicyclo-4,4,0-decane derivative concentration in the foodstuff product.

Food flavoring compositions prepared in accordance with the present invention preferably contain the methyl substituted oxobicyclo-4,4,0-decane derivatives in concentrations ranging from about 0.01% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of disperseion, etc. Alternatively, flavoring compositions in the form of particulate solids can be conveniently prepared by mixing the methyl substituted oxobicyclo-4,4,0-decane derivatives with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and methyl substituted oxobicyclo-4,4,0-decane derivatives in a dry blender until the requisite degree of uniformity is achieved.

It is presently preferred to combine with the methyl substituted oxobicyclo-4,4,0-decane derivatives of our invention, the following adjuvants:

Heliotropin;
Terpinenol-4;
Benzaldehyde;
Anisaldehyde;
Phenyl acetaldehyde;
Benzyl formate;
Benzyl acetate;
Cis-3-hexenyl benzoate;
Methyl Hexanoate;
Hexanal;
Eucalyptol;
Eugenol;
Acetaldehyde;
Ethyl acetate;
Ethyl butyrate;
Turpentine gum oil;
Limonene;
Gum camphor;
Isobornyl acetate;
Borneol;
Cinnamic aldehyde;
Cuminic aldehyde;
Furfural;
Methyl cinnamate;
Cassia oil;
Vanillin;
Maltol;
Parahydroxybenzylacetone;
Dimethyl sulfide;
Alpha-ionone;
Acetic acid;
Isobutyl acetate;
Acetone;
Butyric acid;
Formic acid;
Valeric acid;
Amyl acetate;
Amyl butyrate;
Anethol;
Benzyl salicylate;
Diacetyl;
Dimethyl anthranilate;
Ethyl methylphenylglycidate;
Ethyl succinate;
Ethyl valerate;
Geraniol;
Cis-3-hexen-1-ol;
2-Hexenyl acetate;
2-Hexenyl butyrate;
Hexyl butyrate;
4-(p-Hydroxyphenyl)-2-butanone;
Beta-ionone; Isobutyl cinnamate;
Jasmine;
Lemon essential oil;
Methyl butyrate
Methyl capronate;
Methyl disulfide;
Methyl p-naphthyl ketone;
Orris butter;
Rose absolute;

Terpenyl acetate;
Gamma-undecalactone;
Vanilla;
Alcohol;
Oil of Cubeb;
Phellandrene;
β-phellandrene;
Oil or Coriander;
Oil of Pimento Leaf;
Oil of Patchouli;
Alpha Pinene;
Beta Pinene;
Beta-caryophyllene;
Dihydrocarveol;
Piperonal;
Piperine;
Chavicine;
Piperidine;
Oil of Black Pepper;
Black Pepper Oleoresin;
Capsicum;
Oil of Nutmeg;
Cardamon Oil;
Clove Oil;
Spearmint Oil; and
Oil of Peppermint.

An additional aspect of our invention provides an organoleptically improved smoking tobacco product and additives therefor, as well as methods of making the same which overcome problems heretofore encountered in which specific desired sweet, fruity, berry-like, woody and floral flavor characteristics of natural tobacco (prior to smoking and, on smoking, in the mainstream and in the sidestream) as well as cooling effects, are created or enhanced or modified or augmented and may be readily controlled and maintained at the desired uniform level regardless of variations in the tobacco components of the blend.

This invention further provides improved tobacco additives and methods whereby various desirable natural aromatic tobacco flavoring characteristics with sweet, fruity, berry-like, cooling, woody and floral notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient one or more methyl substituted oxobicyclo-4,4,0-decane derivatives of our invention.

In addition to the methyl substituted oxobicyclo-4,4,0-decane derivatives of our invention other flavoring and aroma additives may be added to the smoking tobacco material or substitute therefor either separately or in mixture with the methyl substituted oxobicyclo-4,4,0-decane derivatives as follows:

I. Synthetic Materials

Beta-ethyl-cinnameldehyde;
Eugenol;
Dipentene;
Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropylacetophenone;
2-Hydroxy-2,5,5,8a-tetramethyl-1-(2-hydroxyethyl)-decahydronaphthalene;
Dodecahydro-3a,6,6,9a-tetramethylnaphtho-(2,1-b)furan
4-Hydroxyhexanoic acid, gamma lactone; and
Polyisoprenoid hydrocarbons defined in Example V of U.S. Pat. No. 3,589,372 issued on June 29, 1971.

II. Natural Oils

Celery seed oil;
Coffee Extract;
Bergamot Oil;
Cocoa extract;
Nutmeg Oil; and
Origanum Oil.

An aroma and flavoring concentrate containing one or more methyl substituted oxobicyclo-4,4,0-decane derivatives of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or sweet notes and/or cooling notes and/or fruity notes and/or woody notes, we have found that satisfactory results are obtained if the proportion by weight of the sum total of methyl substituted oxobicyclo-4,4,0-decane derivative(s) to smoking tobacco material is between 50 ppm and 1,500 ppm (0.015%–0.15%). We have further found that satisfactory results are obtained if the proportion by weight of the sum total of methyl substituted oxobicyclo-4,4,0-decane derivative used to flavoring material is between 1,500 and 15,000 ppm (0.15%–1.5%).

Any convenient method for incorporating the methyl substituted oxobicyclo-4,4,0-decane derivative(s) into the tobacco product may be employed. Thus, the methyl substituted oxobicyclo-4,4,0-decane derivative(s) taken alone or along with other flavoring additives may be dissolved in a suitable solvent such as ethanol, diethyl ether and/or volatile organic solvents and the resulting solution may either be spread on the cured, cased and blended tobacco material or the tobacco material may be dipped into such solution. Under certain circumstances, a solution of the methyl substituted oxobicyclo-4,4,0-decane derivative(s) taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the methyl substituted oxobicyclo-4,4,0-decane derivative(s) in excess of the amounts or concentrations above indicated so that when blended with other tobaccos, the final product will have the percentage within the indicated range.

In accordance with one specific example of our invention, an aged, cured and shredded domestic burley tobacco is sprayed with a 20% ethyl alcohol solution of 3,4,4A,5,8,8A-hexahydro-2,2,5,8A-tetramethyl-1-(2H)-naphthalenone prepared according to Example VI(B), in an amount to provide a tobacco composition containing 800 ppm by weight of 3,4,4A5,8,8A-hexahydro-2,2,5,8A-tetramethyl-1-(2H)-naphthalenone on a dry basis. Thereafter, the alcohol is removed by evaporation and the tobacco is manufactured into cigarettes by the usual techniques. The cigarette when treated as indicated has a desired and pleasing aroma which is detectable in the main and sidestreams when the cigarette is smoked. This aroma is described as being sweeter, more aromatic, more tobacco-like and having a sweet, fruity note.

While our invention is particularly useful in the manufacture of smoking tobacco, such as cigarette tobacco, cigar tobacco and pipe tobacco, other tobacco products, formed from sheeted tobacco dust or fines may also be used. Likewise, the methyl substituted oxobicyclo-4,4,0-decane derivative(s) of our invention can be incorporated with materials such as filter tip materials (e.g. cellulose acetate filters wherein sweet, woody, fruity, floral and/or cooling effects are desired), seam paste, packaging materials and the like which are used along with tobacco to form a product adapted for smoking. Furthermore, the methyl substituted oxobicyclo-4,4,0-decane derivative(s) can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

The methyl substituted oxobicyclo-4,4,0-decane derivative(s) and one or more auxiliary perfume ingredients, including, for example, hydrocarbons, alcohols, ketones, aldehydes, nitriles, esters, lactones or cyclic esters, synthetic essential oils and natural essential oils, may be admixed so that the combined odors of the individual components produce a pleasant and desired fragrance, particularly and preferably in sandalwoody and/or patchouli-like fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) top-notes which are usually low boiling fresh smelling materials.

In perfume compositions, it is the individual components which contribute to their particular olfactory characteristics, however the over-all sensory effect of the perfume composition will be at least the sum total of the effects of each of the ingredients. Thus, one or more of the methyl substituted oxobicyclo-4,4,0-decane derivative(s) of our invention can be used to alter, modify or enhance the aroma characteristics of a perfume composition, for example, by utilizing or moderating the olfactory reaction contributed by another ingredient in the composition.

The amount of methyl substituted oxobicyclo-4,4,0-decane derivative(s) of our invention which will be effective in perfume compositions as well as in perfumed articles and colognes depends on many factors, including the other ingredients, their amounts and the effects which are desired. It has been found that perfume compositions containing as little as 0.01% of methyl substituted oxobicylo-4,4,0-decane derivative(s) or even less (e.g. 0.005%) can be used to impart a minty, camphoraceous, dry, woody, sweet, fruity, patchouli-like, woody patchouli, green, herbaceous, basil-like, citrus-like, bergamot-like, lime-like, grapefruit-like, peppery, precious woody, vertiver-like, fresh, musky, lavander, thyme, rosemary, sweaty, rooty and earthy nuances with floral, citrus, lavander and amber topnotes to soaps, cosmetics, detergents (including anionic, non-ionic, cationic and zwitter-ionic solid or liquid detergents) or other products. The amount employed can range up to 70% of the fragrance components and will depend on considerations of cost, nature of the end product, the effect desired on the finished product and the particular fragrance sought.

The methyl substituted oxobicyclo-4,4,0-decane derivative(s) of our invention are useful (taken alone or together with other ingredients in perfume compositions) in detergents and soaps, space odorants and deodorants, perfumes, colognes, toilet water, hair preparations, such as lacquers, brilliantines, pomades and shampoos; cosmetic preparations, such as, creams, deodorants, hand lotions and sun screens; powders, such as talcs, dusting powders, face powders and the like. As little as 0.1% of the methyl substituted oxobicyclo-4,4,0-decane derivative(s) will suffice to impart an intense minty, camphoraceous, dry woody, sweet fruity, patchouli, woody patchouli, green, herbaceous, basil-like, citrus-like, bergamot-like, lime-like, graperfruit-like, peppery, precious woody, vertiver-like, fresh, musky, lavander, thyme, rosemary, sweaty, rooty and/or earthy aroma to woody perfume formulations. Generally, no more than 5% of the methyl substituted oxobicyclo-4,4,0-decane derivative(s) based on the ultimate end product, is required in the perfume composition.

In addition, the perfume composition or fragrance composition of our invention can contain a vehicle, or carrier for the methyl substituted oxobicyclo-4,4,0-decane derivative(s). The vehicle can be a liquid such as a non-toxic alcohol, a non-toxic glycol, or the like. The carrier can also be an absorbent solid, such as gum (e.g., gum arabic), or components for encapsulating the composition (such as gelatin).

It will thus be apparent that the methyl substituted oxobicyclo-4,4,0-decane dervative(s) of our invention can be utilized to alter, modify or enhance sensory properties, particularly organoleptic properties, such as flavor(s) and/or fragrance(s) of a wide variety of consumable materials.

The following Examples serve to illustrate processes for specifically producing the methyl substituted oxobicyclo-4,4,0-decane derivatives of our invention and also serve to illustrate specific embodiments of our invention.

It will be understood that these Examples are illustrative and the invention is to be considered restricted thereto only as indicated in the appended claims.

All parts and percentages given herein are by weight unless otherwise specified.

EXAMPLE I

PREPARATION OF 3,4,4A,5,8,8A-HEXAHYDRO-2,2,8A-TRIMETHYL-1(2H)-NAPHTHALENONE

Reaction:

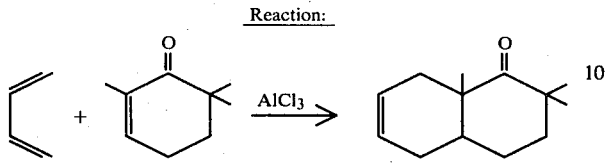

483.0 g (3.5 moles) of 2,6,6-trimethyl-2-cyclohexenone-1, 48.0 g (0.36 moles) of aluminum chloride and 200 cc of anhydrous toluene are combined at room temperature. When the exotherm ceases, the reaction mass is cooled to 0° C. The mixture of cyclohexenone, toluene and aluminum chloride is placed in an autoclave. The contents of the autoclave are cooled to 0° C. and the butadiene (216 g, 4.0 moles) is added. The autoclave is closed immediately and set to operate at room temperature for 6 hours. At the end of the 6 hour period, substantially no cyclohexenone remains. The reaction mass is then transferred to a separatory funnel whereupon water is added and sufficient acetic acid is added to give good separation. The organic layer is washed with two 200 cc volume of sodium bicarbonate. The reaction mass is then stripped and distilled on a one-plate distillation column to yield 429 g of product (64% of theory) with the following fractions:

| Fraction No. | Vapor Temp. (°C.) | Liquid Temp. (°C.) | mm/Hg Pressure | Weight of Fraction (g.) |
|---|---|---|---|---|
| 1 | 70/77 | 95/100 | 1.5/1.5 | 17.0 |
| 2 | 85 | 103 | 1.4 | 44.0 |
| 3 | 90 | 110 | 1.4 | 95.0 |
| 4 | 90 | 111 | 1.4 | 97.0 |
| 5 | 90 | 115 | 1.4 | 93.0 |
| 6 | 92 | 167 | 2.0 | 83.0 |

NMR, IR and mass spectral analysis yield the information that the resulting product has the structure:

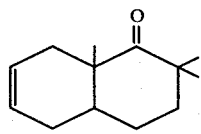

Figure 1:
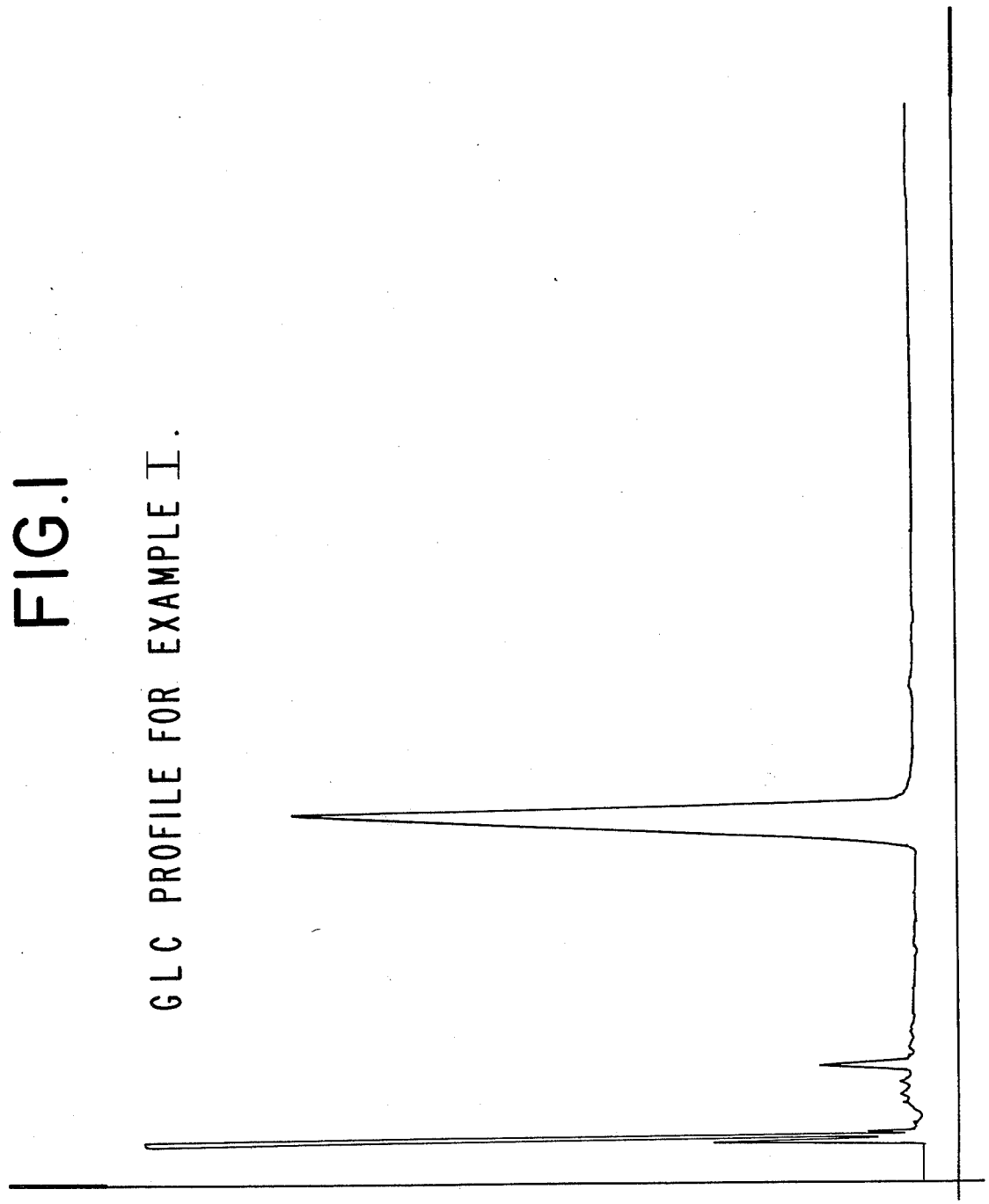
FIG. 1 is the GLC profile for the reaction product of Example I containing the compound having the structure.

FIG. 1 is the GLC profile for the reaction product of Example I containing the compound having the structure:

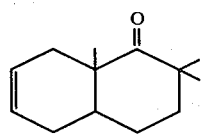

FIG. 2 is the mass spectrum for the product of Example I having the structure:

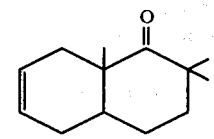

FIG. 3 represents the NMR spectrum for the product of Example I having the structure:

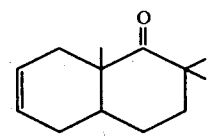

FIG. 4 represents the infrared spectrum for the product of Example I having the structure:

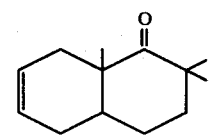

EXAMPLE II

PREPARATION OF OCTAHYDRO-2,2,8A-TRIMETHYL-1(2H)-NAPHTHALENONE

Reaction:

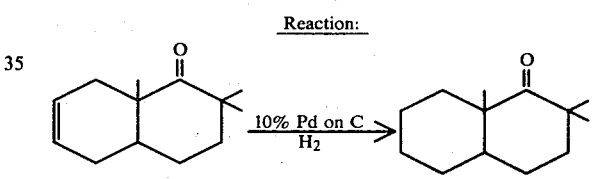

Into a shaker-type pressure vessel (Parr ® shaker) is placed 50.5 g the ketone produced according to Example I having the structure:

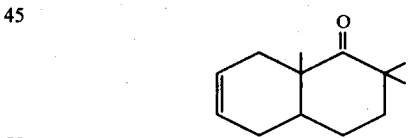

0.6 g of a 10% palladium on carbon catalyst and 50 ml iso-propyl alcohol. The pressure vessel is closed and pressurized with hydrogen to a pressure of 50 psig and maintained at that pressure for a period of 1.3 hours. At the end of the 1.3 hour period the pressure vessel is opened and the contents filtered. The filtrate is stripped of solvent (iso-propyl alcohol) and then distilled using a microdistillation apparatus yielding the following fractions:

| Fraction No. | Vapor Temp. (°C.) | Liquid Temp. (°C.) | mm/Hg. Pressure |
|---|---|---|---|
| 1 | 98/99 | 102/102 | 3.0/3.0 |
| 2 | 100 | 104 | 3.0 |
| 3 | 99 | 105 | 3.0 |
| 4 | 80 | 104 | 3.0 |
| 5 | 99 | 110 | 3.0 |

-continued

| Fraction No. | Vapor Temp. (°C.) | Liquid Temp. (°C.) | mm/Hg. Pressure |
|---|---|---|---|
| 6 | 99 | 140 | 3.0 |
| 7 | 80 | 240 | 3.0 |

The yield is 89%, with fractions 1-6 bulked.

NMR, IR and mass spectral analysis yield the information that the resulting product has the structure:

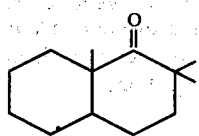

FIG. 5 is the GLC profile for the reaction product of Example II containing the compound having the structure:

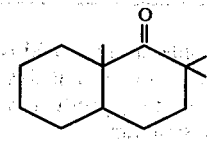

FIG. 6 is the mass spectrum for the product of Example II having the structure:

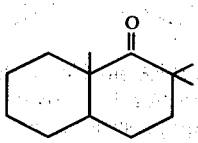

FIG. 7 is the NMR spectrum for the product of Example II having the structure:

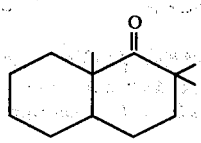

FIG. 8 is the infrared spectrum for the product of Example II having the structure:

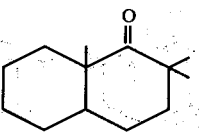

EXAMPLE III

PREPARATION OF 3,4,4A,58,8A-HEXADYDRO-2,2,6(and 7),8A-TETRAMETHYL-1-(2H)-NAPHTHALONE Reaction:

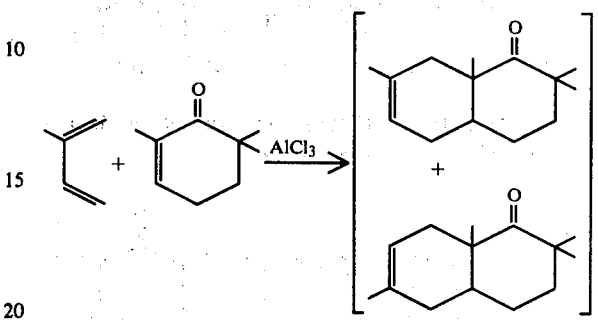

At room temperature, 69 g (0.5 moles) of 2,6,6-cyclohexenone is admixed with 6.7 g (0.05 moles) of aluminum trichloride. The reaction mass exoterms to 44° C. and is cooled. The reaction mass is cooled to 22° C. and over a period of 10 minutes 34 g (0.5 moles) of isoprene is added to the reaction mixture. The reaction mass is stirred at room temperature with cooling for a period of of 1 hour. 0.5 moles additional isoprene is then added. The reaction mass is stirred for an additional hour. At the end of this hour, 150 ml water is added. The reaction mass is then washed as follows:
  a. two 250 ml volumes of water
  b. two volumes of saturated sodium carbonate
  c. one 250 ml volume of saturated sodium chloride solution.

All aqueous layers are combined and extracted with 150 ml toluene. The extract is washed with saturated sodium chloride and the extract and oil layers are then combined and washed with two 250 ml volume of 10% sodium chloride. The oil and aqueous layers are separated and the oil layer is dried over anhydrous sodium sulfate. The resulting material is filtered and then distilled on an one-plate distillation column giving 69 g of product (67% yield) with b.p. of 102°-104° C./3 mmHg.

NMR, IR, and mass spectral analysis yield the information that the resulting product is a mixture of compounds having the structures:

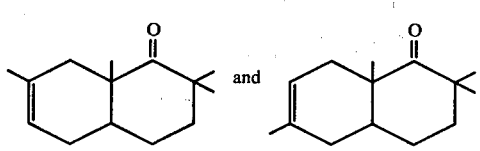

FIG. 9 is the GLC profile for the reaction product of Example III containing the compounds having the structures:

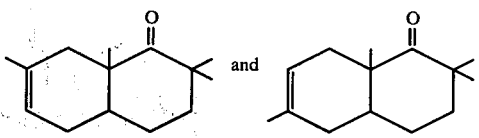

(fraction 2 of one-plate distillation, "Rushover")

FIG. 9A represents the GLC profile for the major product of Example III.

FIG. 10 is the mass spectrum for the product of Example III having the structures:

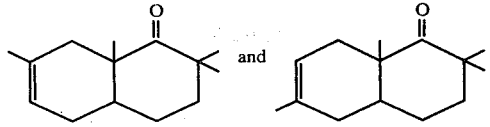

FIG. 11 is the NMR spectrum for the product of Example III having the structures:

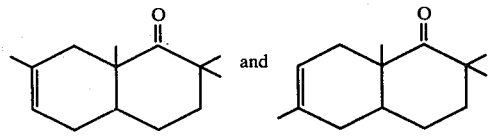

FIG. 12 is the infrared spectrum for the product of Example III having the structures:

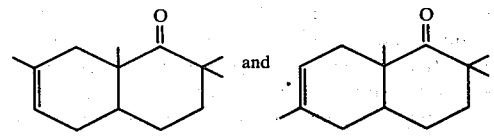

EXAMPLE IV

PREPARATION OF OCTAHYDRO-2,2,6(and 7),8A, TETRAMETHYL-1-1(2H)-NAPHTHALENONE

Reaction:

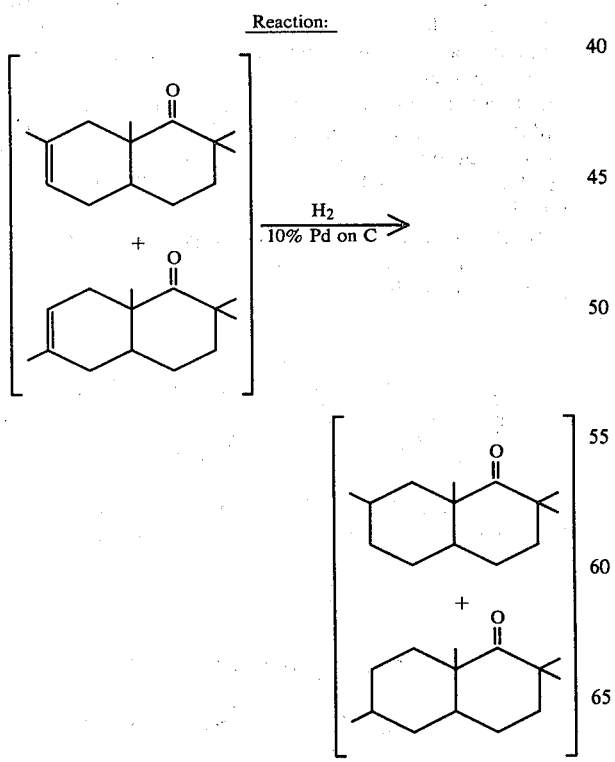

Into a hydrogenation pressure vessel is placed 84 g of the ketone mixture produced according to Example III containing compounds having the structures:

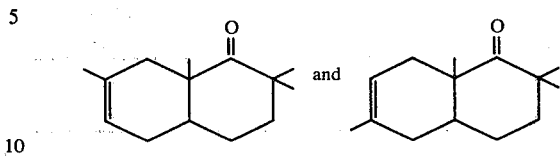

(0.41 moles); 0.5 grams of a 10% palladium on carbon catalyst and 100 ml of isopropyl alcohol. The pressure vessel is closed and with shaking the hydrogen pressure is build up to 44–50 psig. Hydrogen pressure is maintained for a period of 9.3 hours. At the end of the 9.3 hour period the pressure vessel is opened and the contents are filtered and stripped of solvent. The resulting oil is then distilled in a microdistillation apparatus yielding the following fractions:

| Fraction No. | Vapor Temp. (°C.) | Liquid Temp. (°C.) | mm/Hg Pressure | Weight of Fraction (g.) |
|---|---|---|---|---|
| 1 | 97/100 | 109/107 | 3.0 | 3.5 |
| 2 | 100 | 110 | 3.0 | 13.7 |
| 3 | 100 | 115 | 3.0 | 10.9 |
| 4 | 102 | 122 | 3.0 | 23.3 |
| 5 | 100 | 165 | 3.0 | 6.8 |

Fractions 1–5 are bulked. The yield is 95%.

NMR, IR and mass spectral analysis yield the information that the resulting product contains the compounds having the structures:

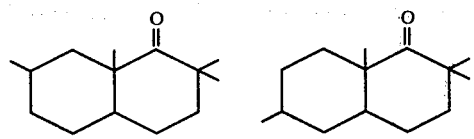

FIG. 13A is the GLC profile for the reaction mixture of Example IV (fraction 3, "cis-isomer") containing the compounds having the structures:

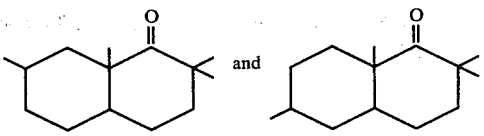

FIG. 13B is the GLC profile for the reaction mixture of Example IV spiked with reactant and thus containing the compounds having the structures:

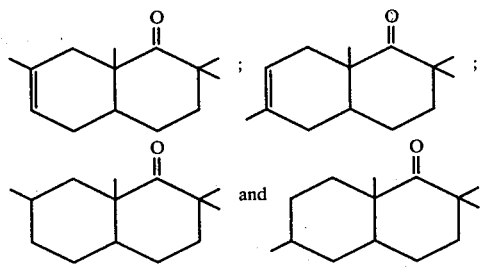

FIG. 14 is the mass spectrum for the reaction product of Example IV, fraction 3, containing the compounds having the structures:

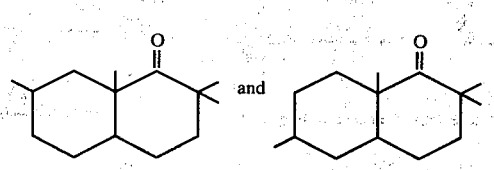

FIG. 15 is the NMR spectrum for the reaction product of Example IV, containing the compounds having the structures:

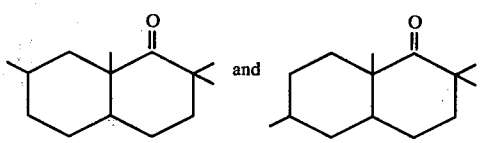

FIG. 16 is the infrared spectrum for the reaction product of Example IV, fraction 3, containing the compounds having the structures:

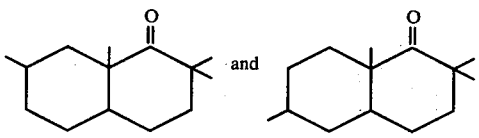

EXAMPLE V
PREPARATION OF 1,2,3,4,4A,5,8,8A-OCTAHYDRO-2,2,6(&7),8A-TETRAHYDRO-1-NAPHTHOL

Reaction:

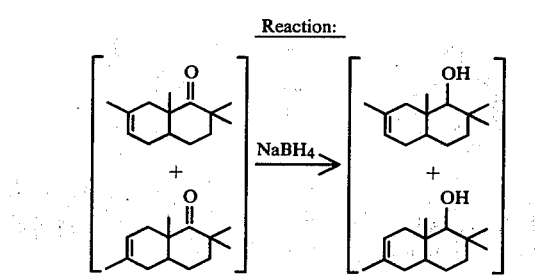

Into a reaction flask equipped with stirrer thermometer and reflux condenser, place 75 g (0.36 moles) of the product of Example III containing the compounds having the structures:

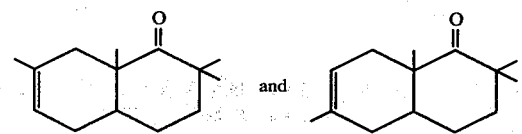

and 50 ml isopropyl alcohol. Then, a mixture of 5.1 g (0.13 moles) of sodium borohydride and 50 ml of isopropyl alcohol is added at room temperature.

The reaction mass is stirred for a period of 5 hours at room temperature and then for a period of 3 hours at 77° C. The reaction is then quenched by adding the reaction mass to 10% acetic acid, aqueous solution. The aqueous phase is separated from the organic phase and the organic phase is washed with saturated sodium carbonate solution and then 10% sodium chloride solution. The organic phase is then dried over anhydrous sodium sulfate and fractionated on a microdistillation apparatus yielding the following fractions:

| Fraction No. | Vapor Temp. (°C.) | Liquid Temp. (°C.) | mm/Hg Pressure | Weight of Fraction (g.) |
|---|---|---|---|---|
| 1 | 27/25 | 43/105 | 3.0/3.0 | 3.7 |
| 2 | 47/102 | 104/112 | 3.0 | 2.7 |
| 3 | 113 | 127 | 3.0 | 3.6 |
| 4 | 121 | 135 | 3.0 | 10.7 |
| 5 | 121 | 140 | 3.0 | 5.7 |
| 6 | 121 | 145 | 3.0 | 5.0 |
| 7 | 118 | 147 | 3.0 | 5.9 |
| 8 | 108 | 167 | 3.0 | 14.9 |
| 9 | 90 | 245 | 3.0 | 7.6 |

Fractions 4-7 are bulked (yield is 49%).

NMR, IR and mass spectral analysis yield the information that the resulting product is a mixture of compounds having the structures:

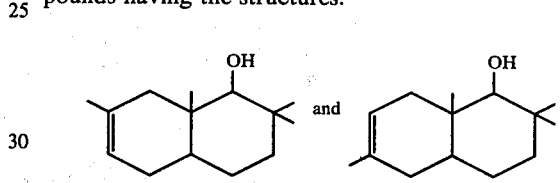

FIG. 17 is the GLC profile for the reaction product of Example V containing the compounds having the structures:

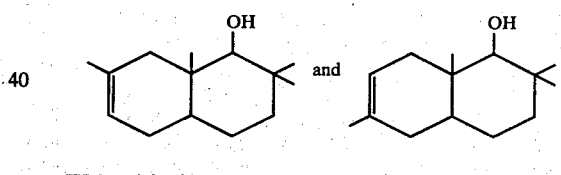

FIG. 18 is the mass spectrum for the reaction product of Example V containing the cis-isomer of the compounds having the structures:

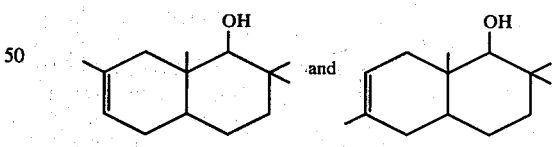

FIG. 19 is the NMR spectrum for the reaction product of Example V containing the cis-isomer of the compounds having the structures:

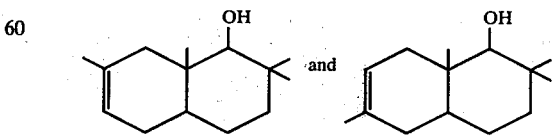

FIG. 20 is the infrared spectrum for the reaction product of Example V containing the cis-isomer of the compounds having the structures:

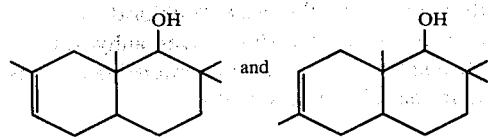

EXAMPLE VIA

PREPARATION OF 3,4,4A,5,8,8A-HEXAHYDRO-2,2,8(and 5),8A-TETRAMETHYL-1-(2H)-NAPHTHALENONE Reaction:

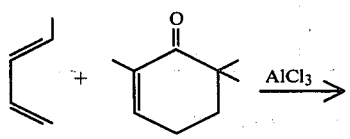

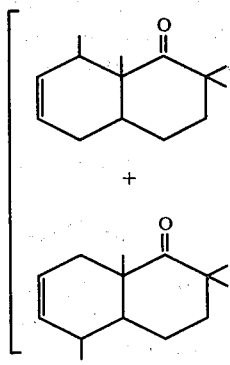

Into a reaction flask equipped with thermometer, reflux condenser and cooling bath is placed 69 g (5 moles) of 2,6,6-trimethyl cyclohexenone. Over a period of 17 minutes with cooling while maintaining the reaction mass at 10° C.–25° C., 6.7 g (0.05 moles) of aluminum trichloride is added thereto. Then, 34 g (0.5 moles) of piperylene (1,3-pentadiene) is then added to the reaction mass with cooling over a period of one hour. The reaction mass is then stirred for a period of one hour at a temperature of 25° C. 100 ml of 10% aqueous hydrochloric acid is then added to the reaction mass with cooling. The aqueous phase is separated from the organic phase and toluene is added thereto. The organic layer is then washed with 100 ml 10% aqueous sodium chloride followed by 10% aqueous sodium hydroxide. The resulting material is then dried over anhydrous sodium sulfate, admixed with sodium bicarbonate, in order to scavange any acid present. The resulting product is filtered and the solvent is stripped off.

The resulting material is fractionally distilled on a six inch microdistillation column to yield the following fractions:

| Fraction No. | Vapor Temp. (°C.) | Liquid Temp. (°C.) | mm/Hg Pressure | Weight of Fraction (g.) |
|---|---|---|---|---|
| 1 | 36/90 | 77/108 | 3.0/3.0 | 14.5 |
| 2 | 99 | 112 | 3.0 | 4.8 |
| 3 | 101 | 115 | 3.0 | 7.3 |
| 4 | 102 | 112 | 3.0 | 8.4 |
| 5 | 102 | 116 | 3.0 | 5.2 |
| 6 | 103 | 119 | 3.0 | 11.8 |
| 7 | 103 | 126 | 3.0 | 11.4 |
| 8 | 103 | 158 | 3.0 | 11.2 |
| 9 | 90 | 220 | 3.0 | 6.1 |

Fractions 2–8 are bulked (yield: 61%)

NMR, IR and spectral analysis yield the information that the resulting product is a mixture of the compounds having the structures:

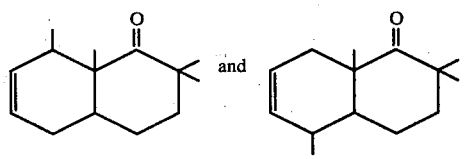

FIG. 21 is the GLC profile for the reaction product of Example VI(A), fraction 7, containing the compounds having the structures:

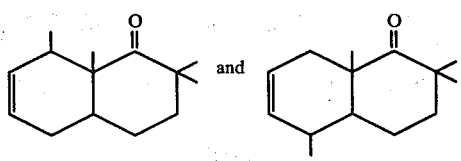

FIG. 22 is the mass spectrum for the reaction product of Example VI(A), fraction 7, containing the compounds having the structures:

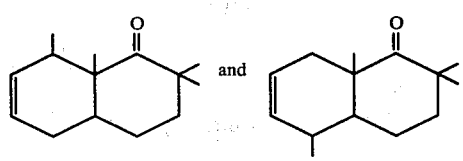

FIG. 23 is the NMR spectrum for the reaction product of Example VI(A) containing the compounds having the structures:

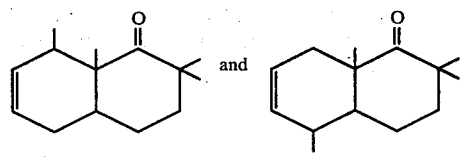

FIG. 24 is the infrared spectrum for the reaction product of Example VI(A) containing the compounds having the structures:

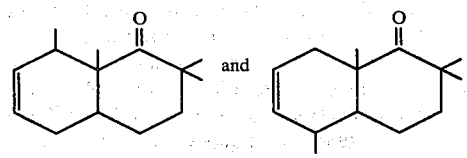

EXAMPLE VIB

PREPARATION OF 3,4,4A,5,8,8A-HEXAHYDRO-2,2,8(and 5),8A-TETRAMETHYL-1-(2H)-NAPHTHALENONE Reaction:

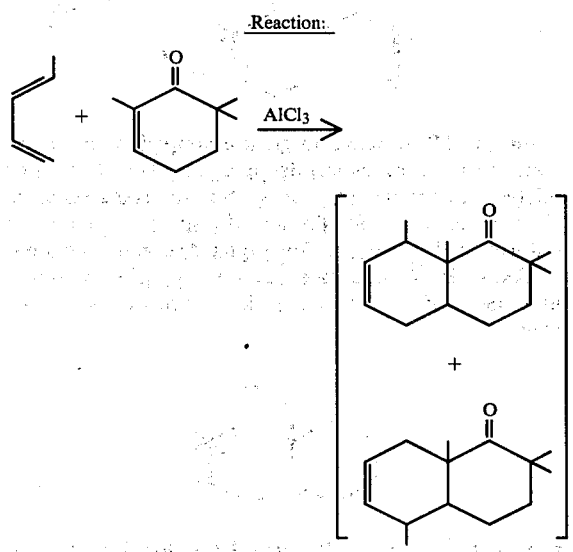

Into a 5 liter reaction flask equipped with stirrer, condenser, thermometer and dropping funnel is placed 200 cc toluene. 33.5 g (0.25 moles) of aluminum chloride is then added. 345 g (2.5 moles) of 2,6,6-cyclohexenone is then added dropwise to the reaction mass which exotherms to 35° C. The reaction mass is cooled to room temperature and 340.0 g (5.0 moles) of piperylene is added dropwise maintaining the temperature at 25° C. The reaction mass is then stirred at room temperature for a period of six hours while being monitered by GLC to completion (conditions: SE 30, column programmed at 100°-150° C. at 8° C. per minute). The reaction mass is then "worked up" by adding water, stirring and separating the layers. The organic layer is then washed with one 1000 cc volume of water stipped and distilled to yield 414 g of product (80% of theory). The distillation is carried out on a 12 inch-packed column (stone) yielding the following fractions:

| Fraction No. | Vapor Temp. (°C.) | Liquid Temp. (°C.) | mm/Hg Pressure | Weight of Fraction (g.) |
|---|---|---|---|---|
| 1 | 56/70 | 100/110 | 2.0/2.8 | 33.0 |
| 2 | 80 | 120 | 0.8 | 32.0 |
| 3 | 100 | 125 | 0.8 | 64.0 |
| 4 | 102 | 126 | 0.8 | 77.0 |
| 5 | 102 | 130 | 0.8 | 90.0 |
| 6 | 101 | 140 | 0.5 | 67.0 |
| 7 | 94 | 172 | 0.5 | 41.0 |
| 8 | 80 | 230 | 0.5 | 70.0 |

Fractions 3-7 are bulked.

NMR, IR and mass spectral analysis yield the information that the resulting product is a mixture of compounds having the structures:

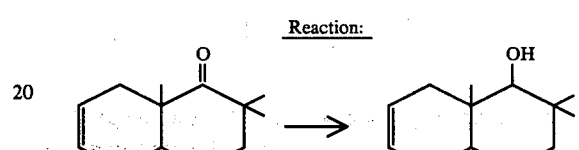

FIG. 25 sets forth the GLC profile for bulk fractions 2-7 for the foregoing distillation.

EXAMPLE VIIA

PREPARATION OF 1,2,3,4,4A,5,8,8A-OCTAHYDRO-2,2,8A-TRIMETHYL-1-NAPHTHOL

Reaction:

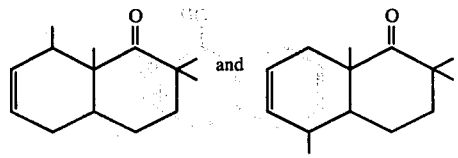

Into a reaction flask, equipped with stirrer, thermometer, reflux condenser and cooling bath, is placed 50 ml anhydrous isopropyl alcohol and 45.4 g (0.12 moles) of 12% sodium borohydride aqueous solution. Over a period of five minutes the ketone reaction product of Example I (245 g; 1.28 moles) having the structure:

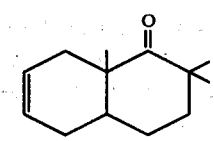

is added to the reaction mass. The reaction mass is then heated to 88° C. and maintained at that temperature for a period of 8 hours. The resulting reaction product is poured into 100 ml of water and extracted with 50 ml of diethyl ether twice. The organic layer is washed with satured sodium chloride solution and dried over anhydrous sodium sulfate. Stripping of the solvent gives 17 g of crystalline product (85% yield). The crude product is recrystallized from hexane giving pure product having a m.p. 58°-59° C.

| Fraction No. | Vapor Temp. (°C.) | Liquid Temp. (°C.) | mm/Hg Pressure |
|---|---|---|---|
| 1 | 97/105 | 114/120 | 4.0/3.2 |
| 2 | 111 | 157 | 3.0 |
| 3 | 114 | 235 | 3.0 |

NMR, IR and mass spectral analysis yield the information that the resulting product has the structure:

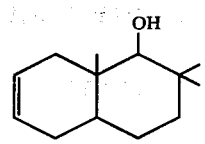

FIG. 26A is the GLC profile for the crude product of the reaction of Example VII(A) containing the compound having the structure:

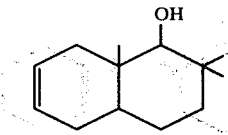

FIG. 26B is the GLC profile for bulked fractions 1-3 of the distillation product of the reaction product of Example VII(A) containing the compound having the structure:

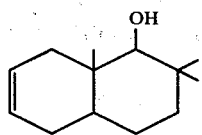

FIG. 27 is the mass spectrum for the reaction product of Example VII(A), bulked fractions 1-3, containing the compound having the structure:

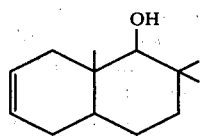

FIG. 28 is the NMR spectrum for the reaction product of Example VII(A), bulked fractions 1-3, containing the compound having the structure:

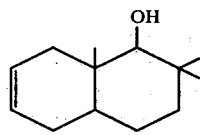

FIG. 29 is the infrared spectrum for the reaction product of Example VII(A), bulked fractions 1-3, containing the compound having the structure:

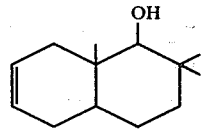

EXAMPLE VIIB

PREPARATION OF 1,2,3,4,4A,5,8,8A-OCTAHYDRO-2,2,8A-TRIMETHYL-1-NAPHTHOL

Reaction:

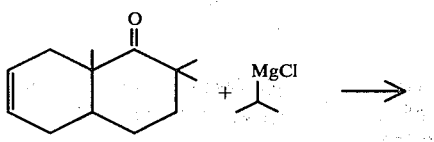

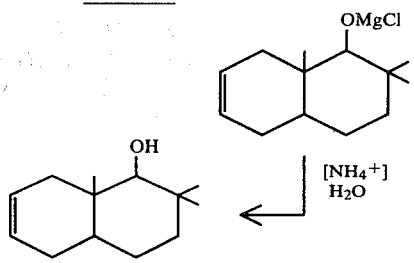

Into a 250 cc reaction flask equipped with stirrer, condenser, thermometer, dropping funnel and nitrogen inlet tube, to provide a nitrogen blanket, is placed 60 cc (0.15 moles) of 2.5 M solution of isopropyl magnesium chloride in dietyl ether. The grignard reagent solution is cooled to 10° C. and dropwise over a period of 5 minutes, 19.2 g (0.1 moles) of the ketone having the structure:

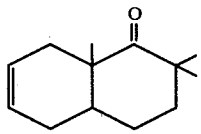

prepared according to Example I is added. The reaction mass exotherms to 30° C. The reaction mass is refluxed for a period of 1.5 hours whereupon GLC analysis indicates completion of the reaction (conditions: SE 30, column programed at 150° C. at 8° C. per minute). The reaction mass is the hydrolyzed with 20 cc of an ammonium chloride solution. The organic phase is separated from the aqueous phase, dried, stripped and distilled on a one-plate column to yield 17 g of crystals having b.p. 100°-114° C./2 mmHg pressure.

The resulting material as confirmed by GLC, IR, and mass spectral analysis has the structure:

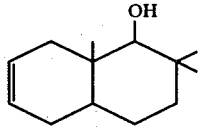

FIG. 30 is the GLC profile for the reaction product after 1.5 hours.

FIG. 31 represents the GLC profile for the reaction product spiked with reactant ketone having the structure:

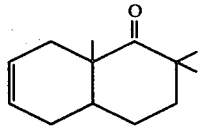

EXAMPLE VIII

PREPARATION OF 1,2,3,4,4A,5,8,8A-OCTAHYDRO-2,2,8(and 5),8A-TETRAMETHYL-1NAPHTHOL Reaction:

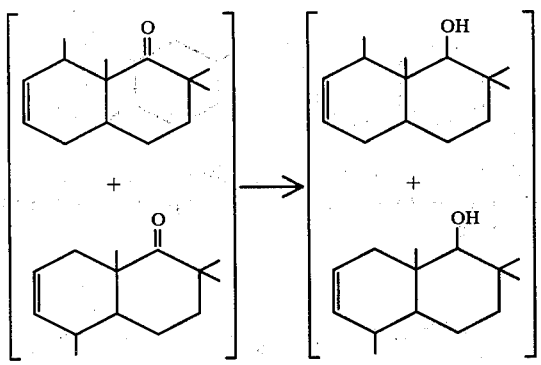

Into a 500 cc reaction flask equipped with stirrer, condenser, thermometer and dropping funnel, 20.7 g (0.55 moles) of lithium aluminum hydride and 50 cc of tetrahydrofuran are added. Dropwise over a period of 5 minutes, 114.0 g (0.55 moles) of the mixture of ketone having the structures:

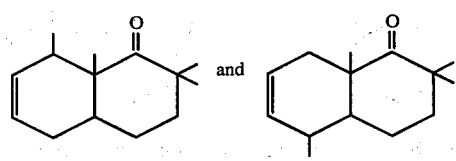

prepared according to Example VIA is added while maintaining the reaction mass at 10°-20° C.

After addition of the mixture of ketones, the reaction mass is stirred at 25° C. for a period of one hour. At the end of the one hour period, GLC analysis indicates that the reaction is complete, there being no starting material present.

The resulting lithium salt reaction product is then hydrolyzed using 20 cc of a 0.4 molar ammonium chloride solution. The resulting two phases, the aqueous phase and the organic phase are separated and the organic phase is dried over anhydrous sodium sulfate, stripped of solvent and distilled on a one plate column yielding 45 g of products (43% of theory). The product is then distilled on a 12-inch stonepack column yielding the following fractions:

| Fraction No. | Vapor Temp. (°C.) | Liquid Temp. (°C.) | mm/Hg Pressure | Weight of Fraction (g.) |
| --- | --- | --- | --- | --- |
| 1 | 80/95 | 110/115 | 1.5/1.0 | 2.0 |
| 2 | 105 | 115 | 1.0 | 9.0 |
| 3 | 105 | 120 | 0.9 | 24.0 |
| 4 | 105 | 200 | 0.9 | 7.0 |

NMR, IR and mass spectral analysis yield the information that the product is a mixture of compounds having two structures:

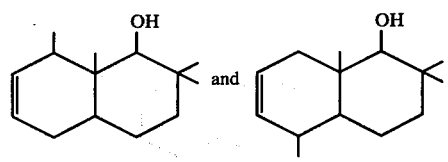

FIG. 32 is the GLC profile for the reaction product of Example VIII containing the compounds having the structures:

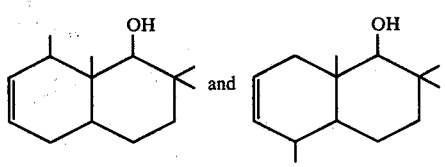

FIG. 33 is the mass spectrum for the reaction product of Example VIII containing the compounds having the structures:

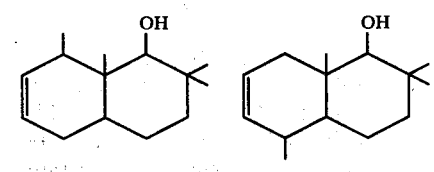

FIG. 34 is the NMR spectrum for the reaction product of Example VIII, fraction 3, containing the compounds having the structures:

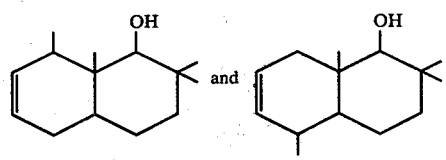

FIG. 35 is the infrared spectrum for fraction 3 of the distillation product of the reaction product of Example VIII containing the compounds having the structures:

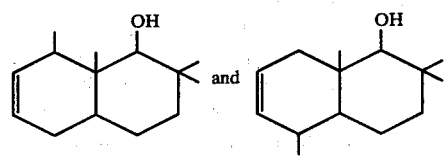

EXAMPLE IX

PREPARATION OF 2,2,6,(and 7),8A-TETRAMETHYL-1-NAPHTHOL

Reaction:

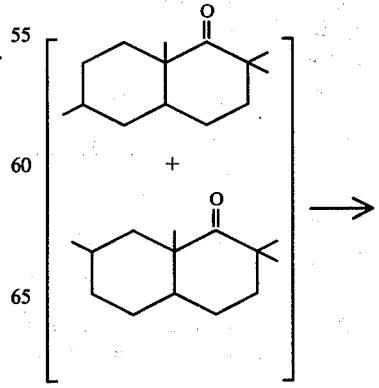

-continued
Reaction:

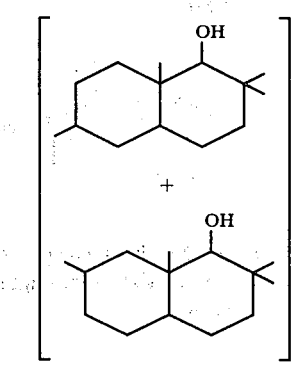

Into a 500 cc reaction flask equipped with stirrer, condenser, thermometer and dropping funnel are placed 100 cc of tetrahydrofuran and 16.23 g (0.408 moles) of 95% lithium aluminum hydride thereby forming a slurry. While maintaining the temperature of the slurry at 10°-20° C., and over a 20 minute period, 85 g (0.408 moles) of the mixture of ketones having the structures:

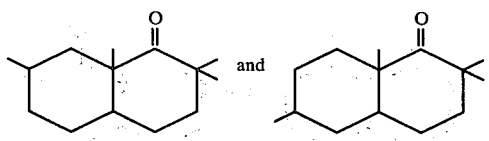

prepared according to Example IV. After addition the reaction mass is stirred at room temperature for a period of 1.5 hours at the end of which time GLC analysis and IR analysis indicates that the reaction is complete.

200 cc of water are then added to the reaction mass with cooling. The reaction mass is then extracted with two 100 cc portions of toluene. The toluene extract is then stripped (of toluene) and the residue is distilled yielding 81.5 g (96% of theory) of product, confirmed by IR, mass spectral analysis and NMR analysis to be a mixture of compounds having the structures:

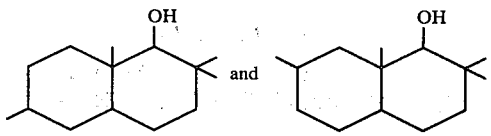

The distillation is carried out using microdistillation apparatus yielding the following fractions:

| Fraction No. | Vapor Temp. (°C.) | Liquid Temp. (°C.) | mm/Hg Pressure | Weight of Fraction (g.) |
|---|---|---|---|---|
| 1 | 120/120 | 122/125 | 0.6/0.6 | 12.0 |
| 2 | 120 | 125 | 0.6 | 17.0 |
| 3 | 120 | 125 | 0.6 | 15.0 |
| 4 | 120 | 125 | 0.6 | 14.0 |
| 5 | 120 | 188 | 0.6 | 24.0 |

FIG. 36 is the GLC profile for the reaction product of Example IX containing the compounds having the structures:

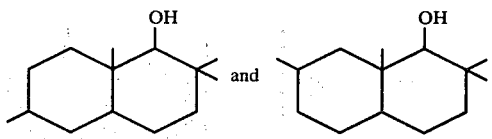

FIG. 37 is the mass spectrum for the reaction product of Example IX containing the compounds having the structures:

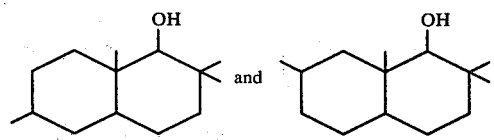

FIG. 38 is the NMR spectrum for the distillation product, fraction 4, of the reaction product of Example IX containing the compounds having the structures:

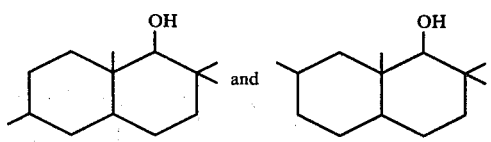

FIG. 39 is the infrared spectrum for fraction 4 of the distillation product of the reaction product of Example IX containing the compounds having the structures:

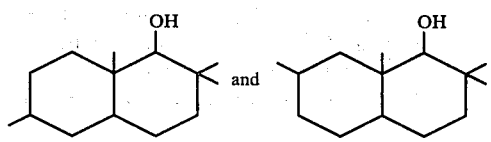

EXAMPLE X

PREPARATION OF DECAHYDRO-2,2,8A-TRIMETHYL-1-NAPHTHOL

Reaction:

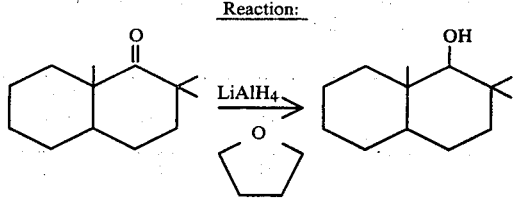

Into a 500 cc reaction flask fitted with stirrer, condenser, thermomether and dropping funnel is placed 14.8 g (0.39 moles) of lithium aluminum hydride in 70 cc of tetrahydrofuran. To the resulting lithium aluminum hydride slurry, dropwise, is added 76.0 g (0.39 moles) of the ketone having the structure:

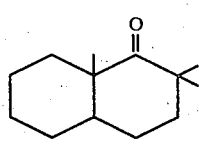

prepared according to Example II. The reaction mass is stirred at room temperature for a period of 3 hours. At the end of the 3 hour period, IR and GLC analysis indicate completion of the reaction. To the resulting reaction mass 100 cc of 0.4 molar acetic acid is added. The organic phase is separated from the aqueous phase and the organic phase is washed with two 50 cc saturated sodium bicarbonate solution portions. The resulting material is then dried over anhydrous sodium sulfate, stripped of solvent and distilled on a one-plate column. The resulting product is then redistilled on a 12 inch stone-packed column to yield the following fractions: (yield 86%)

| Fraction No. | Vapor Temp. (°C.) | Liquid Temp. (°C.) | mm/Hg Pressure | Weight of Fraction (g.) |
|---|---|---|---|---|
| 1 | 75/80 | 90/190 | 0.8/0.7 | 20.0 |
| 2 | 80 | 180 | 0.7 | 46.0 |

The total yield is 66.0 g (86.0% yield). The resulting product has the structure:

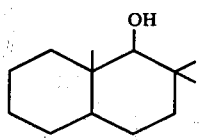

FIG. 40 is the GLC profile for the reaction product of Example X, containing the compound having the structure:

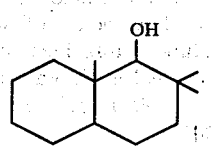

FIG. 41 is the mass spectrum for the reaction product of Example X, containing the compound having the structure:

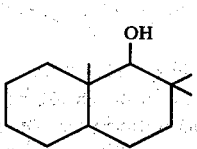

FIG. 42 is the NMR spectrum for fraction 1 of the distillation product of the reaction product of Example X, containing the compound having the structure:

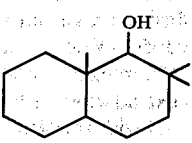

FIG. 43 is the infrared spectrum for fraction 1 of the distillation product of the reaction product of Example X, containing the compound having the structure:

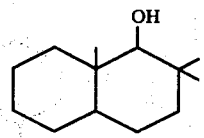

EXAMPLE XI

PREPARATION OF OCTAHYDRO-2,2,8,8a-TETRA-METHYL-1-(2H)-NAPHTHALENONE

Reaction:

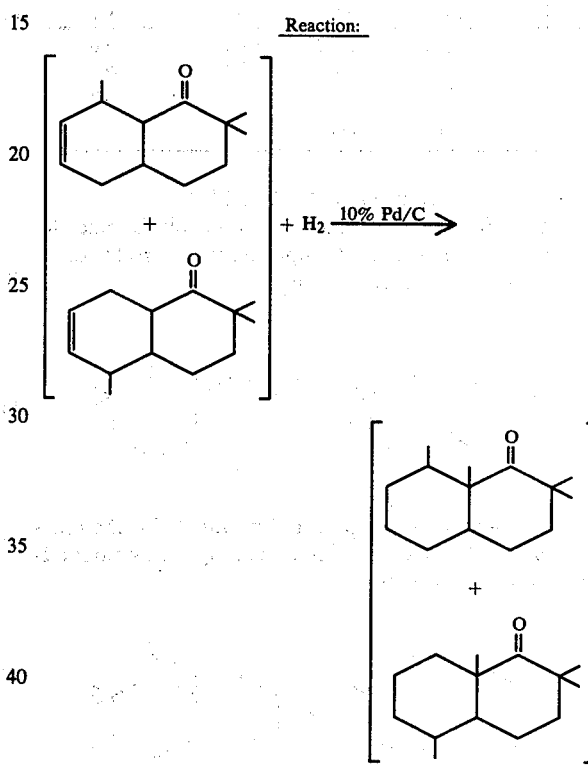

Into an autoclave is charged the following materials:
  2.85 g of 10% palladium on carbon catalyst
  200 cc isopropyl alcohol
  114.0 g (0.55 moles) of the mixture of ketones having the structures:

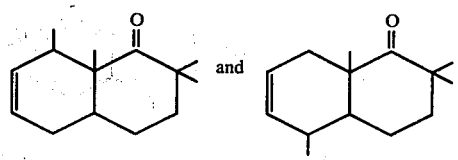

prepared according to Example VI(A).

At room temperature over a period of two hours while maintaining the pressure at 200 psig hydrogen is continually charged to the autoclave.

At the end of the two hour period, the autoclave is opened and the reaction mass is filtered over Supercell ®. The reaction mass is then stripped of solvent and distilled on a one-plate column yielding 104.0 g (91% of theory) of a mixture of compounds having the structures:

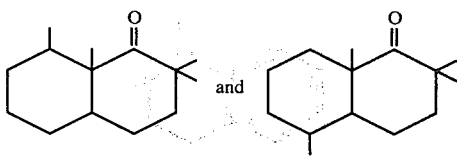

The resulting product is then distilled on a 12 inch stone-packed column yielding the following fractions:

| Fraction No. | Vapor Temp. (°C.) | Liquid Temp. (°C.) | mm/Hg Pressure | Weight of Fraction (g.) |
|---|---|---|---|---|
| 1 | 70/85 | 100/105 | 1.8/1.8 | 4.0 |
| 2 | 85 | 115 | 0.7 | 19.0 |
| 3 | 92 | 117 | 0.7 | 17.0 |
| 4 | 95 | 118 | 0.7 | 32.0 |
| 5 | 95 | 140 | 0.7 | 36.0 |

Fractions 2–5 are product, 91% yield.

GLC, IR, NMR and mass spectral analysis yield the information that the reaction product contains the compounds having the structures:

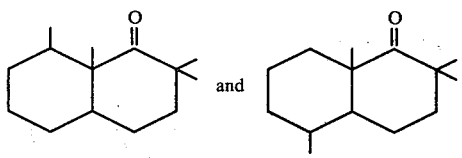

FIG. 44 is the GLC profile (fraction 3) for the reaction product of Example XI containing the compounds having the structures:

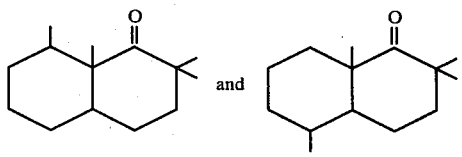

FIG. 45 is the mass spectrum for the reaction product of Example XI, containing the compounds having the structures:

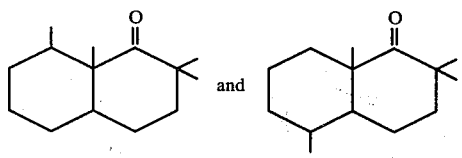

FIG. 46 is the NMR spectrum for fraction 4 of the distillation product of the reaction product of Example XI containing the compounds having the structures:

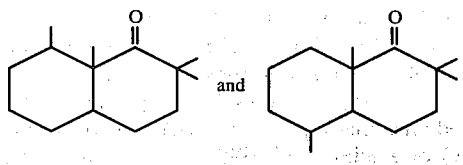

FIG. 47 is the infrared spectrum for fraction 4 of the distillation product of the reaction product of Example XI containing the compounds having the structures:

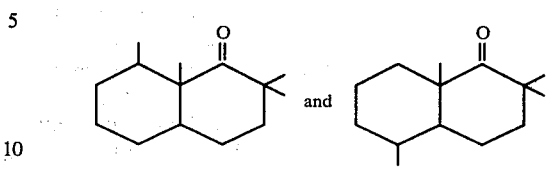

EXAMPLE XII

PREPARATION OF 1,2,3,4,4A,5,8,8A-OCTAHYDRO-1,2,2,8A-TETRAMETHYL-1-NAPHTHOL

Reaction:

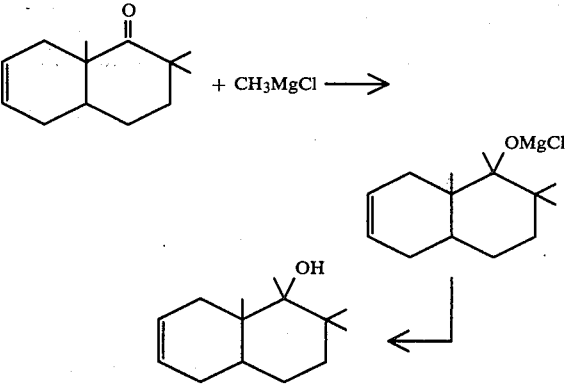

Into a two liter reaction vessel equipped with thermometer, stirrer, addition funnel and reflux condenser are placed 620 ml (1.86 moles) of methyl magnesium chloride (3 M solution) dissolved in tetrahydrofuran. Into the addition funnel is placed a mixture of 250 ml tetrahydrofuran and 245 g (1.24 moles) of the ketone having the structure:

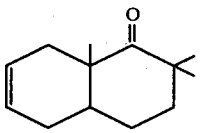

prepared according to Example I.

Over a period of 3 hours the ketone/tetrahydrofuran solution is added to the grignard reagent/tetrahydrofuran solution while maintaining the reaction temperature at 32° C. At the completion of the addition of the ketone, the reaction mass is heated to a temperature in the range of 27°–45° C. while refluxing the reaction mass.

At the end of the reaction (one hour) the reaction mass is added to one liter of 20% acetic acid. The organic layer is washed with one liter of 10% sodium chloride followed by 500 ml saturated sodium carbonate followed by 500 ml saturated sodium chloride. The aqueous layer is extracted with toluene and the toluene extract is combined with the washed organic layer. The reaction product is then dried over anhydrous sodium sulfate, stripped of solvent and distilled yielding the following fractions: Fractions 2–11 are product, 86% yield.

| Fraction No. | Vapor Temp. (°C.) | Liquid Temp. (°C.) | mm/Hg Pressure | Weight of Fraction (g.) |
|---|---|---|---|---|
| 1 | 119/137 | 150/157 | 2.3 | 13.9 |
| 2 | 110 | 146 | 1.5 | 18.5 |
| 3 | 110 | 137 | 2.0 | 19.1 |
| 4 | 111 | 137 | 2.0 | 17.1 |
| 5 | 112 | 143 | 2.0 | 18.6 |
| 6 | 115 | 144 | 2.0 | 21.9 |
| 7 | 113 | 144 | 1.8 | 25.5 |
| 8 | 113 | 145 | 1.8 | 29.0 |
| 9 | 114 | 147 | 1.8 | 29.8 |
| 10 | 114 | 165 | 1.8 | 26.3 |
| 11 | 111 | 225 | 1.8 | 15.5 |

(Distillation carried out on 12 inch Goodlow column).

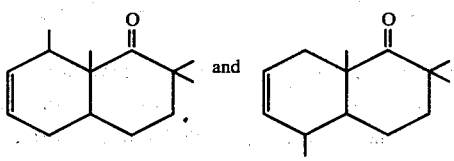

The reaction product has the structure:

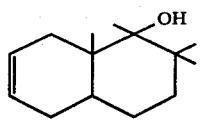

as confirmed by NMR, IR and mass spectral analysis.

FIG. 48 is the GLC profile for the crude reaction product after initial workup of Example XII containing the compound having the structure:

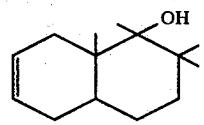

FIG. 49 is the mass spectrum for the reaction product of Example XII containing the compound having the structure:

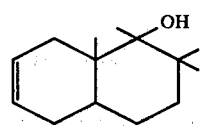

FIG. 50 is the NMR spectrum for fraction 6 of the distillation product of the reaction product of Example XII containing the compound having the structure:

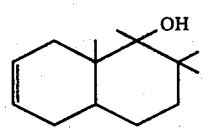

FIG. 51 is the infrared spectrum for fraction 6 of the distillation product of the reaction product of Example XII containing the compound having the structure:

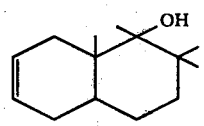

EXAMPLE XIII

PREPARATION OF 1,2,3,4,4A,5,8,8A-OCTAHYDRO-1,2,2,6,(and 7),8A-PENTAMETHYL-1-NAPHTHOL Reaction:

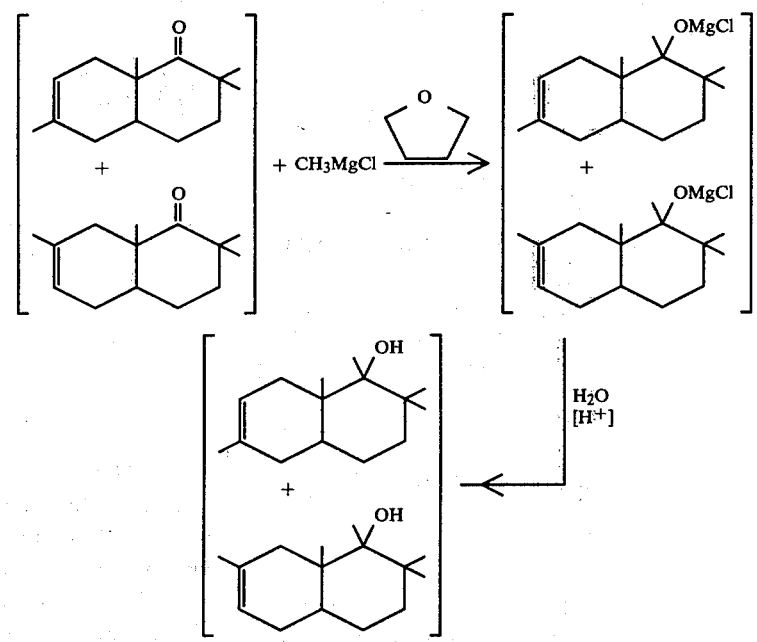

Into a 250 ml reaction flask equipped with stirrer, thermometer, reflux condenser and addition funnel is placed a mixture of 41 g (0.2 moles) of the mixture of ketones having the structures:

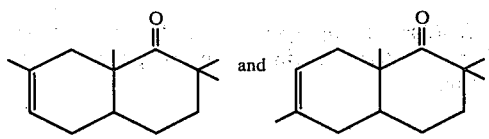

prepared according to Example III, and 50 ml tetrahydrofuran.

Over a period of 15 minutes 100 ml of a 3 M solution of methylmagnesium chloride (0.3 moles) is added to the reaction mass while maintaining the reaction mass at a temperature of less than 30° C. The reaction mass is then stirred for a period of 5.5 hours at the end of which time the reaction is complete. The reaction mass is then added to a mixture of 50 ml acetic acid and 100 ml water. The aqueous layer is separated, and the organic layer is washed with saturated sodium chloride and saturated sodium bicarbonate solution, followed by saturated sodium chloride solution. The washed material is dried over anhydrous sodium sulfate and microdistilled yielding the following fractions:

| Fraction No. | Vapor Temp. (°C.) | Liquid Temp. (°C.) | mm/Hg Pressure | Weight of Fraction (g.) |
|---|---|---|---|---|
| 1 | 98/99 | 115/115 | 0.7 | 4.6 |
| 2 | 95 | 115 | 0.7 | 4.7 |
| 3 | 96 | 116 | 0.7 | 3.5 |
| 4 | 96 | 116 | 0.7 | 2.5 |
| 5 | 97 | 125 | 0.7 | 6.5 |
| 6 | 97 | 170 | 0.7 | 6.9 |
| 7 | 90 | 185 | 0.7 | 0.3 |

The yield is 50%. The reaction product containing compounds having the structures:

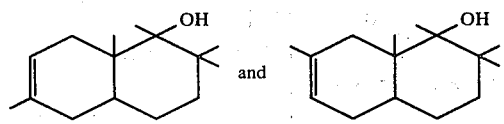

is confirmed to have these structures by means of NMR, IR and mass spectral analysis.

FIG. 52 is the GLC profile for fraction 2 of the one plate distillation product of the reaction product of Example XIII containing the compounds having the structures:

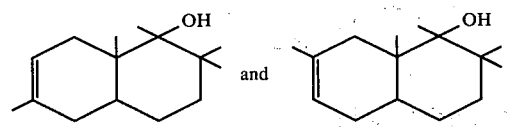

FIG. 53 is the mass spectrum for the reaction product of Example XIII containing the compounds having the structures:

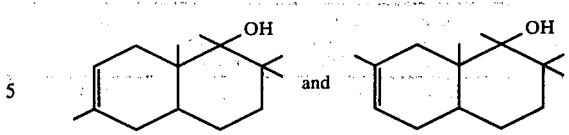

FIG. 54 is the NMR spectrum for fraction 6 of the distillation product of the reaction product of Example XIII containing the compounds having the structures:

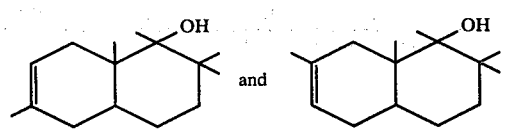

FIG. 55 is the infrared spectrum for fraction 6 of the distillation product of the reaction product of Example XIII containing the compounds having the structures:

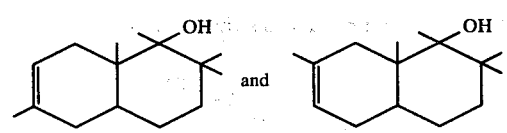

EXAMPLE XIV

PREPARATION OF 1,2,3,4,4A,5,8,8A-OCTAHYDRO-1,2,2,8(and 5),8A-PENTAMETHYL-1-NAPHTHOL Reaction:

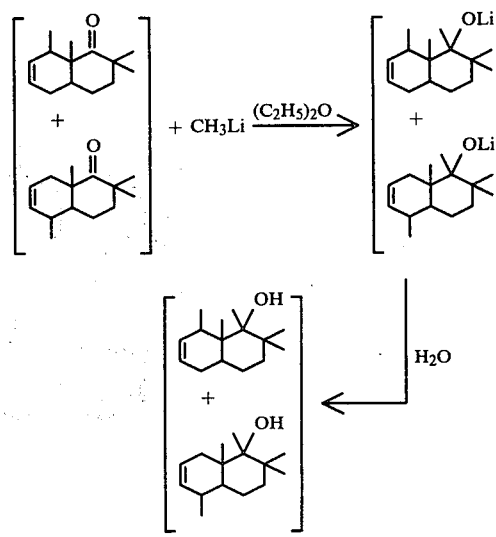

In a 1000 cc reaction flask equipped with stirrer, condenser, thermometer and dropping funnel is placed 687 cc (1.10 moles) of a methyllithium (1.6 M) in diethyl ether solution. The methyllithium solution is cooled to 10° C. While maintaining the reaction mass at 10°-15° C., dropwise, 114.0 g (0.55 moles) of the mixture of ketones having the structures:

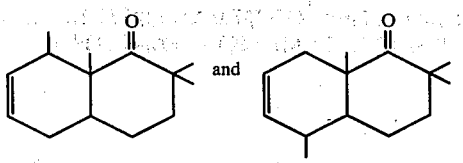

and

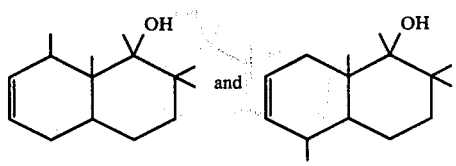

prepared according to Example VIA is added. After addition, IR analysis and GLC analysis indicates that none of the starting material remains.

The resulting organometallic compound is then hydrolyzed with 100 cc of water. The organic phase is separated from the aqueous phase and the organic phase is dried over anhydrous magnesium sulfate, stripped of solvent and distilled on a 12 inch stone-packed column to yield the following fractions:

| Fraction No. | Vapor Temp. (°C.) | Liquid Temp. (°C.) | mm/Hg Pressure | Weight of Fraction (g.) |
|---|---|---|---|---|
| 1 | 65/110 | 120/130 | 1.0/0.8 | 4.0 |
| 2 | 120 | 135 | 0.8 | 10.0 |
| 3 | 120 | 140 | 0.8 | 24.0 |
| 4 | 120 | 145 | 0.8 | 42.0 |

The yield is 80.0 g, which respresents 65% of theory.

NMR, IR and mass spectral analysis yield the information that the reaction product contains two compounds having the structures:

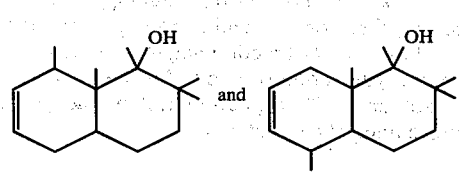

and

FIG. 56 is the GLC profile for fraction 3 of the distillation product of the reaction product of Example XIV containing the compounds having the structures:

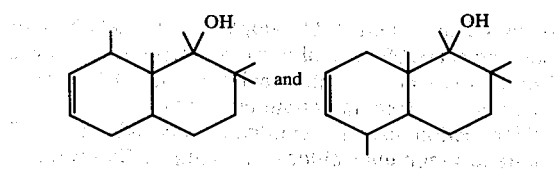

and

FIG. 57 is the mass spectrum for the reaction product of Example XIV containing the compounds having the structures:

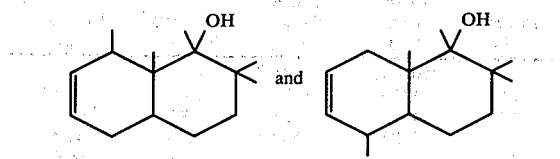

and

FIG. 58 is the NMR spectrum for fraction 4 of the distillation product of the reaction product of Example XIV containing the compounds having the structures:

FIG. 59 is the infrared spectrum for fraction 4 of the distillation product of the reaction product of Example XIV containing the compounds having the structures:

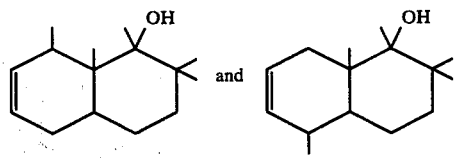

and

EXAMPLE XV

PREPARATION OF DECAHYDRO-1,2,2,8A-TETRAMETHYL-1-NAPHTHOL

Reaction:

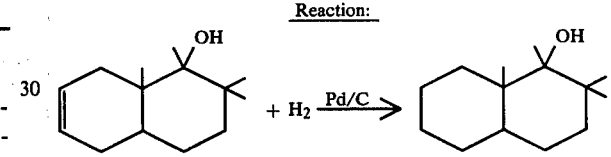

The alcohol (54 g) produced according to Example XII having the structure:

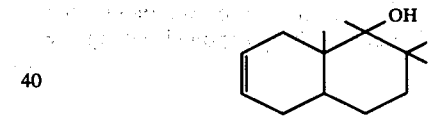

and 100 g of isopropyl alcohol and 0.05 g of a 10% palladium on carbon hydrogenation catalyst are placed in an autoclave.

Over a period of 2 days, while maintaining the hydrogenation pressure of 37–50 psig at a temperature of 25° C., hydrogen is admixed with the reaction mass in a close system.

At the end of this time period the autoclave is opened and the contents are filtered. The reaction product is stripped of solvent and dried over anhydrous magnesium sulfate and then distilled on a 12 inch stone-packed column to yield a compound (52 g (96% yield), b.p. 120° C./0.8 mmHg), as confirmed by NMR, IR and mass spectral analysis to have the structure:

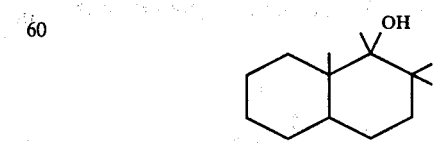

FIG. 60 is the GLC profile for the reaction product of Example XV containing the compound having the structure:

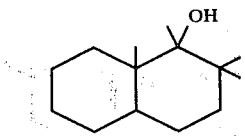

FIG. 61 is the mass spectrum for the reaction product of Example XV containing the compound having the structure:

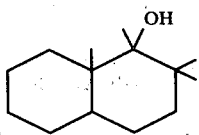

FIG. 62 is the NMR spectrum for the reaction product of Example XV containing the compound having the structure:

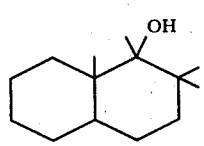

FIG. 63 is the infrared spectrum for the reaction product of Example XV containing the compound having the structure:

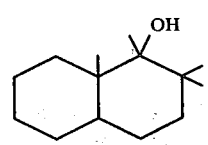

EXAMPLE XVI

PREPARATION OF DECAHYDRO-1,2,2,6,(and 7),8A-PENTAMETHYL-1-NAPHTHOL

Reaction:

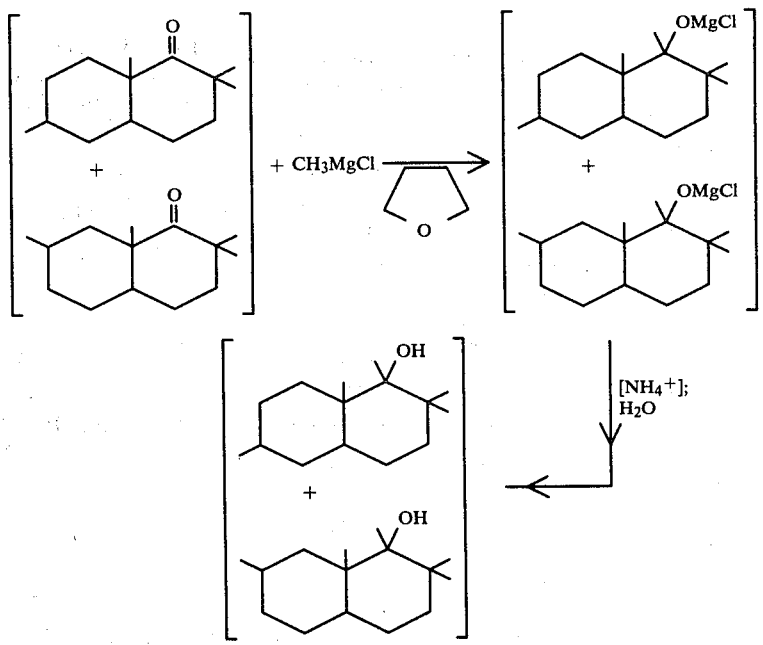

Into a 2000 cc reaction flask equipped with stirrer, condenser, thermometer and dropping funnel is placed 680 cc (2.04 moles) of methylmagnesium chloride (3 M) in a tetrahydrofuran solution. Dropwise allowing a slow exotherm, 170 g (0.82 moles) of the mixture of ketones having the structures:

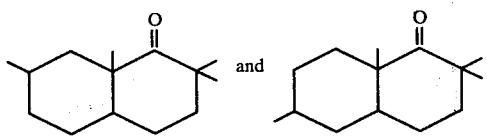

prepared according to Example IV, is added to the reaction mass. After addition, the reaction mass is refluxed for 16 hours while being monitored by GLC analysis in order to ascertain completion.

The reaction mass is then hydrolyzed with 200 cc of saturated ammonium chloride solution. The resulting hydrolyzed material is then extracted with two 100 cc portions of toluene. The toluene extract is stripped of toluene and distilled to yield the following fractions:

| Fraction No. | Vapor Temp. (°C.) | Liquid Temp. (°C.) | mm/Hg Pressure | Weight of Fraction (g.) |
|---|---|---|---|---|
| 1 | 120/120 | 127/130 | 0.9/0.9 | 10.0 |
| 2 | 120 | 130 | 0.8 | 38.0 |
| 3 | 125 | 135 | 0.8 | 37.0 |
| 4 | 125 | 140 | 0.8 | 32.0 |
| 5 | 125 | 180 | 0.8 | 46.0 |

The yield is 138.5 g by GLC analysis which is 75.6% of theory.

GLC, IR and mass spectral analysis yield the information that the resulting product is a mixture of compounds having the structures:

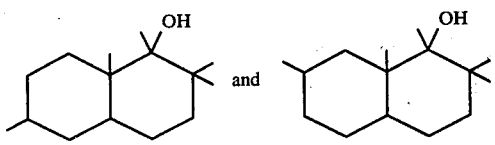

FIG. 64 is the GLC profile of the reaction product (after 8 hours reflux) for Example XVI containing the compounds having the structures:

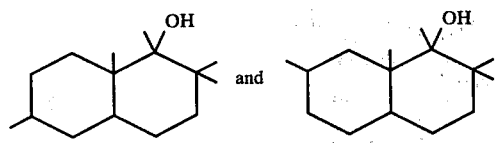

FIG. 65 is the mass spectrum for the reaction product of Example XVI containing the compounds having the structures:

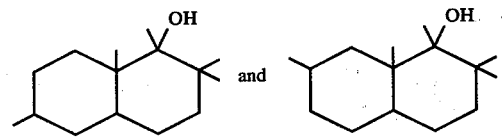

FIG. 66 is the NMR spectrum of fraction 4 of the distillation product of the reaction product of Example XVI containing the compounds having the structures:

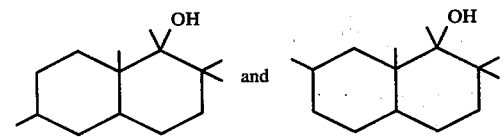

FIG. 67 is the infrared spectrum for fraction 4 of the distillation product of the reaction product of Example XVI containing the compounds having the structures:

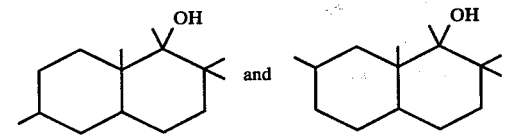

EXAMPLE XVII

PATCHOULI PERFUME FORMULATION

The following mixture is prepared:

| Ingredient | Parts by Weight |
|---|---|
| Orange Oil | 50 |
| Bergamot Oil | 20 |
| Lime Oil | 100 |
| Neroli Oil | 5 |
| 4-(4-Methyl-4-hydroxyamyl) Δ³-cyclohexene carboxaldehyde | 5 |
| 2,3,3A,4,5,7A-Hexahydro-6,7A,8,8-tetramethyl-1,5-methano-1H-inden-1-ol (prepared according to the process of Example I of U.S. Pat. No. 3,989,760 issued on November 2, 1976) | 100 |
| 1',2',3',4',5',6',7',8'-Octahydro-2',3'8',8'-tetramethyl-2'-acetonaphthone isomer mixture produced according to the process of Example VII of Application for U.S. Letters Pat. No. 434,948 filed on January 21, 1974, now U.S. Pat. No. 3,911,018 issued on October 7, 1975 | 50 |
| Gamma Methyl Ionone | 20 |
| 1-acetyl-2,5,5-trimethylcycloheptane produced according to U.S. Pat. No. 3,869,411 issued on March 4, 1975 | 50 |

| In the alternative one of the following ingredients: | Parts by Weight |
|---|---|
| Methyl substituted oxobicyclo-4,4,0-decane derivatives prepared according to one of Examples I–XVI | 100 |
| Produced according to Example I | 100 |
| Produced according to Example II Mixture of: | 100 |
| Produced according to Example III Mixture of: | 100 |
| Produced according to Example IV Mixture of: | 100 |

-continued

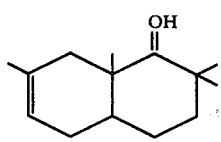

and

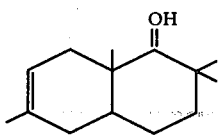

Produced according to Example V

Mixture of: 100

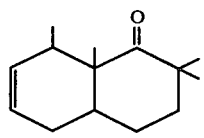

and

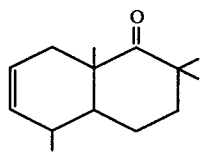

Produced according to either of Examples VIA of VIB

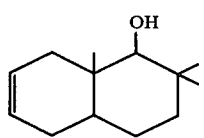 100

Produced according to Example VIIA or VIIB

Mixture of: 100

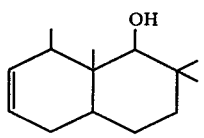

and

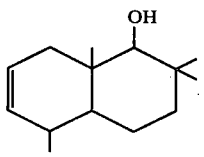

Produced according to Example VIII

-continued

Mixture of: 100

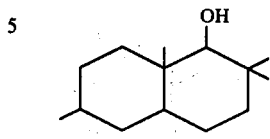

and

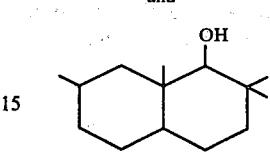

Produced according to Example IX

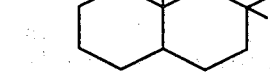 100

Produced according to Example X

Mixture of: 100

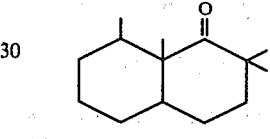

and

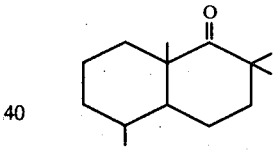

Produced according to Example XI

Mixture of: 100

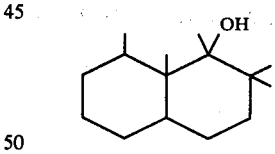

and

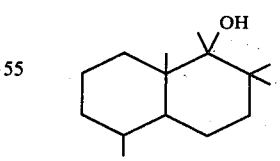

Prepared by reacting CH₃Li with product of Example XI

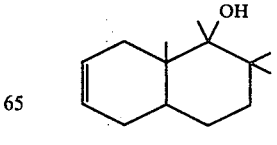 100

Produced according to Example XII

-continued

| Mixture of: | 100 |
|---|---|

[Structure: bicyclic with OH, methyl substituents, alkene]

and

[Structure: bicyclic with OH, methyl substituents, alkene]

Produced according to Example XIII

| Mixture of: | 100 |
|---|---|

[Structure: bicyclic with OH]

and

[Structure: bicyclic with OH]

Produced according to Example XIV

| | 100 |
|---|---|

[Structure: bicyclic with OH]

Produced according to Example XV

| Mixture of: | 100 |
|---|---|

[Structure: bicyclic with OH]

and

[Structure: bicyclic with OH]

Produced according to Example XVI

The methyl substituted oxobicyclo-4,4,0-decane derivatives prepared according to one of Examples I–XVI, when added to this formulation in the amount indicated; and also in amounts up to 30% by weight of the total mixture; or in amounts as little as 1.0% by weight of this mixture, imparts aroma characteristics to this patchouli composition, in addition to the patchouli aroma as follows:

TABLE II

| Structure | Fragrance Profile |
|---|---|
| [ketone structure] Produced according to Example I | Minty, camphoraceous, dry woody with floral citrus background. |
| [ketone structure] Produced according to Example II Mixture of: | A sweet, fruity, minty, camphoraceous aroma with a woody patchouli undertone flavor characteristic. |
| [ketone structure] and [ketone structure] Produced according to Example III Mixture of: | A green herbaceous aroma with a lavander top note and a basil/citrus undertone with bergamot-like nuances. |
| [ketone structure] and [ketone structure] Produced according to Example VIA or VIB | A rich herbaceous lavander, thyme/rosemary aroma which becomes sweaty on dry out |
| [OH structure] Produced according to Examples VIIA or VIIB Mixture of: | A patchouli, woody, camphoraceous aroma with a borneol-like undertone flavor |
| [ketone structure] and [ketone structure] Produced according to Example IV Mixture of: | A peppery, dry woody aroma with a precious woody background and vetiver-like and ambery nuances. |
| [OH structure] and [OH structure] Produced according to Example V Mixture of: | A citrus (lime) aroma with dry woody and patchouli undertones. |
| [OH structure] | An intense patchouli-like aroma with a woody background |

TABLE II-continued

| Structure | Fragrance Profile |
|---|---|
| and [OH-substituted decalin structure] Produced according to Example VIII Mixture of: | |
| [OH-substituted decalin structure] Produced according to Example IX | Sandalwood, patchouli-like aroma with incense-like undertones |
| [OH-substituted decalin structure] Produced according to Example X Mixture of: | An earthy, camphoraceous, woody, borneol-like, patchouli aroma with precious, woody undertones. |
| [ketone decalin structure] and [ketone decalin structure] Produced according to Example XI | An earthy, camphoraceous, woody, borneol-like, patchouli aroma with precious, woody undertones. |
| [OH-substituted decalin structure] Produced according to Example XII Mixture of: | A camphoraceous/borneol, earthy, rooty, woody aroma with a patchouli background |
| [OH-substituted decalin structure] and [OH-substituted decalin structure] Produced according to Example XIII Mixture of: | A dry woody, rooty, patchouli aroma with camphoraceous and borneol undertones |
| [OH-substituted decalin structure] and [OH-substituted decalin structure] Produced according to Example XVI | A patchouli aroma with minty topnotes |
| [OH-substituted decalin structure] Produced according to Example XV Mixture of: | A patchouli aroma with minty topnotes |
| [OH-substituted decalin structure] and [OH-substituted decalin structure] Produced according to Example XVI | An earthy, camphoraceous aroma with patchouli background |

EXAMPLE XVIII

Preparation of Soap Compositions

Part A

A total of 100 g of soap chips produced from unperfumed sodium base toilet soap made from tallow and coconut oil is mixed with 1 g of the methyl substituted oxobicyclo-4,4,0-decane derivatives prepared according to one of Examples I–XVI until a substantially homogeneous composition is obtained. The soap composition manifests an excellent patchouli-like character having aroma nuances and undertones as indicated in Table III below.

Part B

A total of 100 g of soap chips produced from unperfumed sodium base toilet soap made from tallow and coconut oil is admixed with 1 g of one of the perfume compositions set forth in Example I–XVI until a substantially homogeneous composition is obtained. The soap compositions manifest aromas as indicated in Table II, supra, with a characteristic patchouli aroma.

TABLE III

| Structure | Fragrance Profile |
|---|---|
| [ketone decalin structure] Produced according to Example I | Minty, camphoraceous, dry woody with floral citrus background. |
| [ketone decalin structure] Produced according to Example II Mixture of: | A sweet, fruity, minty, camphoraceous aroma with a woody patchouli undertone flavor characteristic. |
| [ketone decalin structure] and [ketone decalin structure] Produced according to Example III | A green herbaceous aroma with a lavander top note and a basil/citrus undertone with bergamot-like nuances. |

TABLE III-continued

| Structure | Fragrance Profile |
|---|---|
| Mixture of: 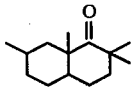 Produced according to Example IV | A peppery, dry woody aroma with a precious woody background and vetiver-like and ambery nuances. |
| Mixture of: 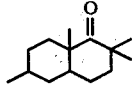 Produced according to Example V | A citrus (lime) aroma with dry woody and patchouli undertones. |
| Mixture of: 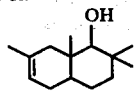 Produced according to Example VIA or VIB | A rich herbaceous lavander, thyme/rosemary aroma which becomes sweaty on dry out |
| 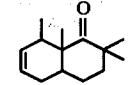 Produced according to Examples VIIA or VIIB | A patchouli, woody, camphoraceous aroma with a borneol-like undertone flavor |
| Mixture of: 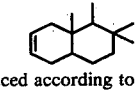 Produced according to Example VIII | An intense patchouli-like aroma with a woody background |
| Mixture of: 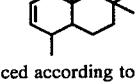 Produced according to Example IX | Sandalwood, patchouli-like aroma with incense-like undertones |
| 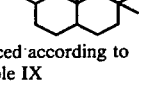 Produced according to Example X | An earthy, camphoraceous, woody, borneol-like, patchouli aroma with precious, woody undertones. |

TABLE III-continued

| Structure | Fragrance Profile |
|---|---|
| Mixture of: 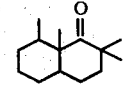 Produced according to Example XI | An earthy, camphoraceous, woody, borneol-like, patchouli aroma with precious, woody undertones. |
| 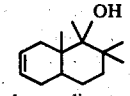 Produced according to Example XII | A camphoraceous/borneol, earthy, rooty, woody aroma with a patchouli background |
| Mixture of: 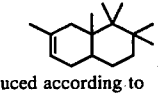 Produced according to Example XIII | A dry woody, rooty, patchouli aroma with camphoraceous and borneol undertones |
| Mixture of: 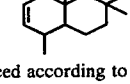 Produced according to Example XVI | A patchouli aroma with minty topnotes |
| 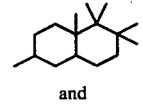 Produced according to Example XV | A patchouli aroma with minty topnotes |
| Mixture of: 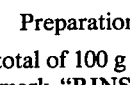 Produced according to Example XVI | An earthy, camphoraceous aroma with patchouli background |

EXAMPLE XIX

Preparation of a Detergent Composition

A total of 100 g of a detergent powder sold under the trademark "RINSO" are mixed with 0.15 g of a perfume composition containing one of the mixtures prepared according to Example XVII until a substantially homogeneous composition having patchouli fragrances with aroma nuances as indicated in Table II is obtained.

EXAMPLE XX

Preparation of a Cosmetic Base

A cosmetic powder is prepared by mixing 100 g of talcum powder with 0.25 g of one of the perfume compositions of Examples XVII in a ball mill. A second cosmetic powder is similarly prepared except that the mixture produced in Example XVII is replaced with one of the products produced in one of Examples I-XVI, that is, one of the methyl substituted oxobicyclo-4,4,0-decane derivatives of one of Examples I-XVI. The cosmetic powder containing the materials of Example XVII have patchouli aromas with dominating undertones and nuances as indicated in Table II, supra, in Example XVII. The cosmetic powder produced using the materials of one of Examples I-XVI have patchouli-like characters with aroma nuances as indicated in the Table IV below:

TABLE IV

| Structure | Fragrance Profile |
|---|---|
| Produced according to Example I | Minty, camphoraceous, dry woody with floral citrus background. |
| Produced according to Example II | A sweet, fruity, minty, camphoraceous aroma with a woody patchouli undertone flavor characteristic. |
| Produced according to Example III Mixture of: | A green herbaceous aroma with a lavander top note and a basil/citrus undertone with bergamot-like nuances. |
| Produced according to Example IV Mixture of: | A peppery, dry woody aroma with a precious woody background and vetiver-like and ambery nuances. |
| Produced according to Example V Mixture of: | A citrus (lime) aroma with dry woody and patchouli undertones. |
| 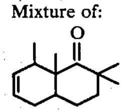 | A rich herbaceous lavander, thyme/rosemary aroma which becomes sweaty on dry out |
| Produced according to Example VIA or VIB | |
| Produced according to Examples VIIA or VIIB Mixture of: | A patchouli, woody, camphoraceous aroma with a borneol-like undertone flavor |
| Produced according to Example VIII Mixture of: | An intense patchouli-like aroma with a woody background |
| Produced according to Example IX | Sandalwood, patchouli-like aroma with incense-like undertones |
| Produced according to Example X Mixture of: | An earthy, camphoraceous, woody, borneol-like, patchouli aroma with precious, woody undertones. |
| Produced according to Example XI | An earthy, camphoraceous, woody, borneol-like, patchouli aroma with precious, woody undertones. |
| Produced according to Example XII Mixture of: | A camphoraceous/borneol, earthy, rooty, woody aroma with a patchouli background |
| Produced according to Example XIII Mixture of: | A dry woody, rooty, patchouli aroma with camphoraceous and borneol undertones |
| | A patchouli aroma with |

TABLE IV-continued

| Structure | Fragrance Profile |
|---|---|
| [structure with OH] and [structure with OH] Produced according to Example XVI | minty topnotes |
| [structure with OH] Produced according to Example XV | A patchouli aroma with minty topnotes |
| Mixture of: [structure with OH] and [structure with OH] Produced according to Example XVI | An earthy, camphoraceous aroma with patchouli background |

EXAMPLE XXI

LIQUID DETERGENT CONTAINING METHYL SUBSTITUTED OXOBICYCLO-4,4,0-DECANE DERIVATIVES PREPARED ACCORDING TO ONE OF EXAMPLES I-XVI

Concentrated liquid detergents with warm patchouli-like aromas having undertones and aroma nuances as indicated in Table V, below, containing 0.2%, 0.5% and 1.2% of one of the products produced in accordance with Example I-XVI (methyl substituted oxobicyclo-4,4,0-decane derivatives) are prepared by adding appropriate quantities of methyl substituted oxobicyclo-4,4,0-decane derivatives as indicated in Table V, below, to liquid detergents known as P-87. The warm patchouli aroma of the liquid detergents increases with increasing concentrations of methyl substituted oxobicyclo-4,4,0-decane derivatives as indicated in Table V, below, with increasing aroma nuances as indicated in Table V, below:

TABLE V

| Structure | Fragrance Profile |
|---|---|
| [ketone structure] Produced according to Example I | Minty, camphoraceous, dry woody with floral citrus background. |
| [ketone structure] Produced according to Example II | A sweet, fruity, minty, camphoraceous aroma with a woody patchouli undertone flavor characteristic. |
| Mixture of: [ketone structure] and | A green herbaceous aroma with a lavander top note and a basil/citrus undertone with bergamot-like nuances. |

TABLE V-continued

| Structure | Fragrance Profile |
|---|---|
| [ketone structure] Produced according to Example III Mixture of: [ketone structure] and [ketone structure] Produced according to Example IV | A peppery, dry woody aroma with a precious woody background and vetiver-like and ambery nuances. |
| Mixture of: [structure with OH] and [structure with OH] Produced according to Example V | A citrus (lime) aroma with dry woody and patchouli undertones. |
| Mixture of: [ketone structure] and [ketone structure] Produced according to Example VIA or VIB | A rich herbaceous lavander, thyme/rosemary aroma which becomes sweaty on dry out |
| [structure with OH] Produced according to Examples VIIA or VIIB | A patchouli, woody, camphoraceous aroma with a borneol-like undertone flavor |
| Mixture of: [structure with OH] and [structure with OH] Produced according to Example VIII | An intense patchouli-like aroma with a woody background |
| Mixture of: [structure with OH] and [structure with OH] Produced according to Example IX | Sandalwood, patchouli-like aroma with incense-like undertones |
| [structure with OH] | An earthy, camphoraceous, woody, borneol-like, patchouli aroma with precious, woody undertones. |

TABLE V-continued

| Structure | Fragrance Profile |
|---|---|
| Produced according to Example X Mixture of: 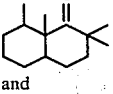 and 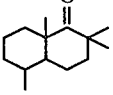 | An earthy, camphoraceous, woody, borneol-like, patchouli aroma with precious, woody undertones. |
| Produced according to Example XI 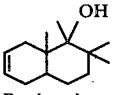 | A camphoraceous/borneol, earthy, rooty, woody aroma with a patchouli background |
| Produced according to Example XII Mixture of: 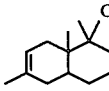 and 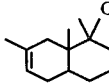 | A dry woody, rooty, patchouli aroma with camphoraceous and borneol undertones |
| Produced according to Example XIII Mixture of: 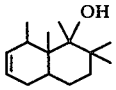 and 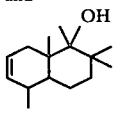 | A patchouli aroma with minty topnotes |
| Produced according to Example XVI 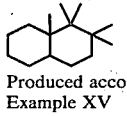 | A patchouli aroma with minty topnotes |
| Produced according to Example XV Mixture of: 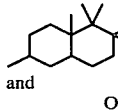 and 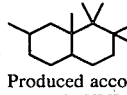 | An earthy, camphoraceous aroma with patchouli background |
| Produced according to Example XVI | |

EXAMPLE XXII

Preparation of Cologne and Handkerchief Perfume

The compositions of Example XXII are incorporated in colognes having concentrations of 2.0%, 2.5%, 3.0%, 3.5% and 4.0% in 75%, 80%, 85% and 90% aqueous ethanol and into handkerchief perfumes in concentrations of 15%, 20%, 25%, 30%, 35% and 40% (in 80%, 85%, 90% and 95% aqueous ethanol). The use of the compositions of Example XVII affords distinct and definitive patchouli aroma having nuances and undertones as indicated in Table II of Example XVII.

EXAMPLE XXIII

Cologne and Handkerchief Perfume

The methyl substituted oxobicyclo-4,4,0-decane derivatives produced by the processes of any of Examples I–XVI are incorporated into perfumes having concentrations of 2.0%, 2.5%, 3.0%, 4.5% and 5.0% in 75%, 80%, 85% and 95% aqueous ethanol; into handkerchief perfumes at concentrations of 8%, 10%, 12%, 15% and 25% (in 80%, 90% and 95% aqueous ethanol). Each of the methyl substituted oxobicyclo-4,4,0-decane derivatives produced according to Examples I–XVI afford distinct and definitive warm patchouli-like aromas with various nuances and undertones as indicated in Table VI, below, to the handkerchief perfumes and to colognes.

TABLE VI

| Structure | Fragrance Profile |
|---|---|
| 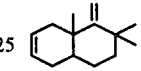 Produced according to Example I | Minty, camphoraceous, dry woody with floral citrus background. |
| 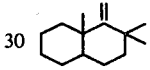 Produced according to Example II Mixture of: 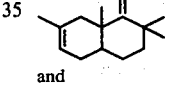 and 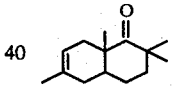 | A sweet, fruity, minty, camphoraceous aroma with a woody patchouli undertone flavor characteristic. A green herbaceous aroma with a lavander top note and a basil/citrus undertone with bergamot-like nuances. |
| Produced according to Example III Mixture of: 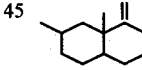 and 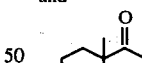 | A peppery, dry woody aroma with a precious woody background and vetiver-like and ambery nuances. |
| Produced according to Example IV Mixture of: 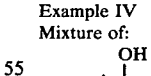 and 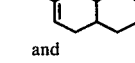 | A citrus (lime) aroma with dry woody and patchouli undertones. |
| Produced according to Example V Mixture of:  and 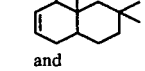 | A rich herbaceous lavander, thyme/rosemary aroma which becomes sweaty on dry out |

TABLE VI-continued

| Structure | Fragrance Profile |
|---|---|
| Produced according to Example VIA or VIB | |
| Produced according to Examples VIIA or VIIB | A patchouli, woody, camphoraceous aroma with a borneol-like undertone flavor |
| Mixture of: ... and ... Produced according to Example VIII | An intense patchouli-like aroma with a woody background |
| Mixture of: ... and ... Produced according to Example IX | Sandalwood, patchouli-like aroma with incense-like undertones |
| Produced according to Example X | An earthy, camphoraceous, woody, borneol-like, patchouli aroma with precious, woody undertones. |
| Mixture of: ... and ... Produced according to Example XI | An earthy, camphoraceous, woody, borneol-like, patchouli aroma with precious, woody undertones. |
| Produced according to Example XII | A camphoraceous/borneol, earthy, rooty, woody aroma with a patchouli background |
| Mixture of: ... and ... Produced according to Example XIII | A dry woody, rooty, patchouli aroma with camphoraceous and borneol undertones |
| Mixture of: ... and ... Produced according to Example XVI | A patchouli aroma with minty topnotes |
| Produced according to Example XV | A patchouli aroma with minty topnotes |
| Mixture of: ... and ... Produced according to Example XVI | An earthy, camphoraceous aroma with patchouli background |

EXAMPLE XXIV

Imitation Oil of Black Pepper Flavor Formulation

The following mixture is prepared:

| Ingredients | Parts by Weight |
|---|---|
| Oil of Cubeb | 40.0 |
| Alpha phellandrene | 35.0 |
| Oil of Coriander | 9.0 |
| Oil of Pimento Leaf | 3.0 |
| Oil of Patchouli | 0.2 |
| Alpha Pinene | 1.5 |
| Beta Pinene | 3.0 |
| Beta caryophyllene | 4.0 |
| Dihydrocarveol | 1.0 |
| Piperonal | 0.8 |
| Piperine | 1.0 |
| Piperidine | 1.5 |
| TOTAL | 100.0 |

To half of this formulation 5% by weight of one of the materials produced according to either Example I or IV is added. Nothing is added to the other half. The formulations are diluted in food grade alcohol at levels of 50 ppm, 100 ppm, 150 ppm and 200 ppm in each of the comparisons at each of the levels the formulations containing the materials of Example I or IV have a stronger more natural-like black pepper aroma and flavor characteristic with excellent and pleasant oriental flavor nuances and notes. Accordingly, the materials of Example I and IV are considered to advantageously augment the standard black pepper oil (imitation) making it more natural-like.

To the foregoing material containing either of the substances of Example I or IV is added, in an equal quantity, 4-terpineol propionate. The 4-terpineol propionate even enhances the flavor further insofar as causing it to be more natural-like black pepper.

EXAMPLE XXV

Basic Walnut Flavor Formulation

The following basic walnut formulation is prepared:

| Ingredients | Parts by Weight |
|---|---|
| Cyclotene | 4 |
| Vanillin | 1 |
| Butyl isovalerate | 2 |
| Benzaldehyde | 6 |
| 2,3-Diethyl pyrazine (10% in food grade ethyl alcohol) | 2 |
| Ethyl-2-methyl valerate | 2 |
| Gamma Butyrolactone | 20 |
| Gamma Hexenyl lactone | 10 |
| 2,4-Decadienal (0.1% in food grade ethyl alcohol) | 0.5 |
| 2,4-Heptadienal (0.1% in food grade ethyl alcohol) | 0.5 |
| Butylidene phthalide | 2 |
| Propylene glycol USP | 95 |

The foregoing flavor formulation is divided into two parts. To the first part at the rate of 5% is added the methyl substituted oxobicyclo-4,4,0-decane derivative prepared according to either of Example XII or XIII. To the second part, nothing is added. Both flavors are compared by a bench panel at the rate of 20 ppm in water. The flavor with the addition of the product produced according to each of Examples XII and XIII have pleasant fresh walnut kernel taste with fresh walnut aromas not present in the basic walnut flavor formulation. Therefore, the flavors with the materials produced according to both Examples XII and SIIII are preferred as being much more characteristic in the walnut flavor by the bench panel (unanimous preference). The flavor is also evaluated at 1 ppm and the same unaminous preference is obtained.

EXAMPLE XXVI

Basic Oral Hygiene Flavor Formulation

The following basic oral hygiene flavor formulation is prepared:

| Ingredients | Parts by Weight |
|---|---|
| Peppermint oil | 89.0 |
| Spearmint oil | 2.0 |
| Clove oil | 1.0 |
| Anethole | 2.0 |
| Cardamon oil | 0.1 |
| Wintergreen oil | 5.0 |
| Cinnamic aldehyde | 0.9 |

The basic oral hygiene flavor formulation is now divided into two parts. To the first part at the rate of 10% is added the methyl substituted oxobicyclo-4,4,0-decane derivatives prepared according to each of Examples II, X or XI. To the second part, nothing is added. The flavor with the flavors with the addition of the materials produced according to either of Examples II, X or XI have fresher minty/eucalyptol aroma and flavor characteristics with woody notes. Therefore, the flavors with the materials produced according to Examples II, X or XI are preferred by the bench panel.

EXAMPLE XXVII

Preparation of a Soap Composition

One hundred grams of soap chips are produced according to Example V of U.S. Pat. No. 4,058,487 issued on Nov. 15, 1977, as follows:

"The sodium salt of an equal mixture of $C_{10}$–$C_{14}$ alkane sulfonate (95% active), 40 pounds, is dissolved in a mixture of 80 pounds of anhydrous isopropanol and 125 pounds of deionized water at 150° F. In this mixture is dissolved 10 pounds of partially hydrogenated cocoanut oil fatty acids and 15 pounds of sodium mono-$C_{14}$ alkyl maleate, and the pH of this solution is adjusted to 6.0 by the addition of a small amount of 50% aqueous solution of sodium hydroxide. The isopropanol is distilled off, and the remaining aqueous solution is drum dried. The resulting solid actives are then blended in a chip mixture with 10 pounds water, 0.2 pounds titanium hydroxide and 0.7 pounds of one of the materials produced according to Examples I–XVI as enumerated in the Table below. The chips are then plodded into logs, cut to size and finally stamped into bars having a pH of approximately 6.9."

Each of the perfumed soaps manifests aromas with strong patchouli notes as indicated in the Table VIII below:

TABLE VIII

| Structure | Fragrance Profile |
|---|---|
| Produced according to Example I | Minty, camphoraceous, dry woody with floral citrus background. |
| Produced according to Example II | A sweet, fruity, minty, camphoraceous aroma with a woody patchouli undertone flavor characteristic. |
| Mixture of: ... and ... Produced according to Example III | A green herbaceous aroma with a lavander top note and a basil/citrus undertone with bergamot-like nuances. |
| Mixture of: ... and ... Produced according to Example IV | A peppery, dry woody aroma with a precious woody background and vetiver-like and ambery nuances. |
| Mixture of: ... and ... | A citrus (lime) aroma with dry woody and patchouli undertones. |

TABLE VIII-continued

| Structure | Fragrance Profile |
|---|---|
| (structure with OH) Produced according to Example V Mixture of: | |
| (structure with O) and (structure with O) Produced according to Example VIA or VIB | A rich herbaceous lavander, thyme/rosemary aroma which becomes sweaty on dry out |
| (structure with OH) Produced according to Examples VIIA or VIIB Mixture of: | A patchouli, woody, camphoraceous aroma with a borneol-like undertone flavor |
| (structure with OH) and (structure with OH) Produced according to Example VIII Mixture of: | An intense patchouli-like aroma with a woody background |
| (structure with OH) and (structure with OH) Produced according to Example IX | Sandalwood, patchouli-like aroma with incense-like undertones |
| (structure with OH) Produced according to Example X Mixture of: | An earthy, camphoraceous, woody, borneol-like, patchouli aroma with precious, woody undertones. |
| (structure with O) and (structure with O) Produced according to Example XI | An earthy, camphoraceous, woody, borneol-like, patchouli aroma with precious, woody undertones. |
| (structure with OH) Produced according to Example XII Mixture of: | A camphoraceous/borneol, earthy, rooty, woody aroma with a patchouli background |

TABLE VIII-continued

| Structure | Fragrance Profile |
|---|---|
| (structure with OH) and (structure with OH) Produced according to Example XIII Mixture of: | A dry woody, rooty, patchouli aroma with camphoraceous and borneol undertones |
| (structure with OH) and (structure with OH) Produced according to Example XVI | A patchouli aroma with minty topnotes |
| (structure with OH) Produced according to Example XV Mixture of: | A patchouli aroma with minty topnotes |
| (structure with OH) and (structure with OH) Produced according to Example XVI | An earthy, camphoraceous aroma with patchouli background |

EXAMPLE XXVII

Preparation of a Detergent Composition

A total of 100 pounds of a detergent powder prepared according to U.S. Pat. No. 4,058,472 and containing 5% by weight of the sodium salts of a mixture of sulfonated $C_{14}$–$C_{18}$ alkyl catechol as a surface active component, the mixture being 60 parts by weight of mono-$C_{14}$–$C_{18}$ alkyl catechol and 40 parts by weight of di-$C_{14}$–$C_{18}$ alkyl catechol and 40 parts by weight of di-$C_{14}$–$C_{18}$ alkyl catechol, 35% of sodium tetrapyrophosphate, 30% of sodium silicate, 20% of sodium carbonate, 3% of sodium carboxymethyl cellulose and 7% of starch is mixed with 0.15 grams of one of the methyl substituted oxobicyclo-4,4,0-decane derivatives produced according to one of Example I–XVI as set forth in Table IX, below, until a substantially homogeneous composition is obtained. Each of the compositions have excellent patchouli aromas with nuances and undertones as enumerated in the Table below:

TABLE IX

| Structure | Fragrance Profile |
|---|---|
| (structure with O) Produced according to Example I | Minty, camphoraceous, dry woody with floral citrus background. |

TABLE IX-continued

| Structure | Fragrance Profile |
|---|---|
| Produced according to Example II | A sweet, fruity, minty, camphoraceous aroma with a woody patchouli undertone flavor characteristic. |
| Produced according to Example III Mixture of: | A green herbaceous aroma with a lavander top note and a basil/citrus undertone with bergamot-like nuances. |
| Produced according to Example IV Mixture of: | A peppery, dry woody aroma with a precious woody background and vetiver-like and ambery nuances. |
| Produced according to Example V Mixture of: | A citrus (lime) aroma with dry woody and patchouli undertones. |
| Produced according to Example VIA or VIB | A rich herbaceous lavander, thyme/rosemary aroma which becomes sweaty on dry out |
| Produced according to Examples VIIA or VIIB Mixture of: | A patchouli, woody, camphoraceous aroma with a borneol-like undertone flavor |
| Produced according to Example VIII Mixture of: | An intense patchouli-like aroma with a woody background |
| Produced according to Example IX | Sandalwood, patchouli-like aroma with incense-like undertones |
| Produced according to Example X Mixture of: | An earthy, camphoraceous, woody, borneol-like, patchouli aroma with precious, woody undertones. |
| Produced according to Example XI | An earthy, camphoraceous, woody, borneol-like, patchouli aroma with precious, woody undertones. |
| Produced according to Example XII Mixture of: | A camphoraceous/borneol, earthy, rooty, woody aroma with a patchouli background |
| Produced according to Example XIII Mixture of: | A dry woody, rooty, patchouli aroma with camphoraceous and borneol undertones |
| Produced according to Example XVI | A patchouli aroma with minty topnotes |
| Produced according to Example XV Mixture of: | A patchouli aroma with minty topnotes |
| Produced according to | An earthy, camphoraceous aroma with patchouli background |

TABLE IX-continued

| Structure | Fragrance Profile |
|---|---|
| Example XVI | |

EXAMPLE XXIX

Tobacco Filter

Into a 20 mm cellulose acetate filter is added the mixture of ketones having the structures:

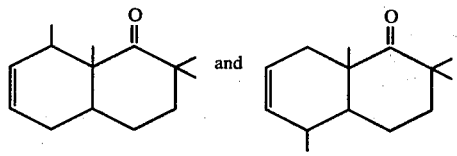

and prepared according to Example VIA at the rate of 1000 ppm (10 micro liters of a 10% solution of said ketones are added to the filter). The filter is then attached to a full flavor cigarette on the market, e.g. (1) Marlboro ®, (2) Winston ® or (3) Viceroy ®, as well as on a Kentucky 1A3 reference cigarette (produced by the University of Kentucky) yielding the following results:

(1) Registered trademark of the Phillip Morris Company. (2) Registered trademark of the R. J. Reynolds Company. (3) Registered trademark of the Brown & Williamson Company.

1. Both cigarettes containing the ketone mixture additive, when compared to a cigarette having a filter without said ketone mixture additive, gives rise to a sweet, fruity, woody, cooling, floral and berry-like aroma on smoking with a pleasant cooling effect and rather noticeable reduced harshness.
2. Both cigarettes containing said ketone mixture additive, have a lesser degree of "hotness" and give rise to a "fresh" taste on smoking.

EXAMPLE XXX

Tobacco Flavor Formulations

Cigarettes are produced using the following tobacco formulations:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| $H_2O$ | 5.3 |

At the rate of 0.2%, the following tobacco flavor formulation is applied to all of the cigarettes produced with the above tobacco formulation:

| Ingredients | Parts by Weight |
|---|---|
| Ethyl butyrate | .05 |
| Ethyl valerate | .05 |
| Maltol | 2.00 |
| Cocoa Extract | 26.00 |
| Coffee Extract | 10.00 |
| Ethyl Alcohol (95%) | 20.00 |
| $H_2O$ | 41.90 |

To portions of 50% of the cigarettes at levels of 10 and 20 ppm, methyl substituted oxobicyclo-4,4,0-decane derivatives as indicated in Table X below are added. These cigarettes are hereinafter called "experimental" cigarettes and the cigarettes without the methyl substituted oxobicyclo-4,4,0-decane derivatives as set forth in Table X below, are hereinafter called "control" cigarettes. The "control" and "experimental" cigarettes are then evaluated by paired comparison and the results are as follows:

a. In aroma, the "experimental" cigarettes are all found to be more aromatic with nuances as indicated in Table X below;

b. In smoke flavor, the "experimental" cigarettes are found to be more aromatic, more sweet with bitter, richer and less harsh nuances on smoking in both the mainstream and the sidestream than the "control" cigarettes.

The "experimental" cigarettes containing 20 ppm of each of the compounds which are methyl substituted oxobicyclo-4,4,0-decane derivatives prepared according to the examples in the instant case and set forth in Table X below are found to be superior in flavor than those not containing such compounds:

TABLE X

| Structure | Tobacco profile |
|---|---|
| Produced according to Example II | A sweet, woody, citrusy aroma with cooling nuances prior to and on smoking in the mainstream and in the sidestream. |
| Mixture of: and Produced according to either of Examples VI(A) or VI(B) | A sweet, fruity, berry, cooling, woody, floral aroma both prior to and on smoking in the mainstream and in the sidestream. |
| Produced according to Example VII(A) or VII(B) | A sweet, woody, vetiver-like aroma and taste, both prior to and on smoking in the mainstream and the sidestream |
| Mixture of compounds having the structures: and Produced according to Example VIII | A woody, patchouli-like, oriental-like, aroma both to and on smoking causing Virginia-like tobacco to attain a Turkish tobacco aroma and taste |
| Mixture of compounds having the Structures: | A sweet, woody aroma and taste both prior to and on smoking |

TABLE X-continued

| Structure | Tobacco profile |
|---|---|
| and 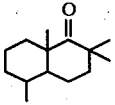<br>Produced according to Example XI | |
| 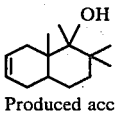<br>Produced according to Example XII | A sweet, woody, vertiver-like aroma and taste both prior to and smoking in the mainstream and the sidestream |
| Mixture of compounds having the structures:<br>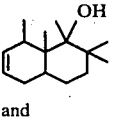<br>and<br>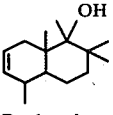<br>Produced according to Example XIV | A woody, patchouli-like aroma and taste both prior to and on smoking yielding a cigar-type taste in the mainstream and the sidestream |
| Mixture of:<br>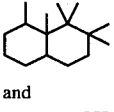<br>and<br>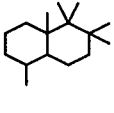<br>Prepared by reacting CH₃Li with product of Example XI | A woody, camphoraceous, and patchouli-like aroma and taste both prior to and on smoking with woody, oriental notes in the smoke causing it to be useful in the production of Turkish tobacco flavor, this material imparts a Turkish tobacco aroma and taste nuance to Virginia tobaccos in both the mainstream and the sidestreams |
| Mixture of compounds having the structures:<br>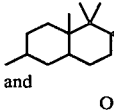<br>and<br>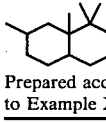<br>Prepared according to Example XVI | A woody, patchouli-like aroma and taste both prior to and on smoking |

EXAMPLE XXXI

A. Powder Flavor Composition

20 Grams of the flavor composition of Example XXV is emulsified in a solution containing 300 gm gum acacia and 700 gm water. The emulsion is spray-dried with a Bowen Lab Model Drier utilizing 260 c.f.m. of air with an inlet temperature of 500° F., an outlet temperature of 200° F., and a wheel speed of 50,000 rpm.

B. Sustained Release Flavor

The following mixture is prepared:

| Ingredients | Parts by Weight |
|---|---|
| Liquid Sweet Anise Flavor Composition of Example XXV | 20 |
| Propylene glycol | 9 |
| Cab-O-Sil ® M-5 (Brand of Silica produced by the Cabot Corporation of 125 High Street, Boston, Mass. 02110; Physical Properties: Surface area: 200 m²/gm Nominal particle size: 0.012 microns Density: 2.3 lbs/cu.ft) | 5.00 |

The Cab-O-Sil is dispersed in the liquid sweet anise flavor compositions of Example XXV with vigorous stirring, thereby resulting in a viscous liquid. 71 Parts by weight of the powder flavor composition of Part A, supra, is then blended into the said viscous liquid, with stirring, at 25° C. for a period of 30 minutes resulting in a dry, free flowing sustained release flavor powder.

EXAMPLE XXXII

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example XXV is added to the solution which is then homogenized to form an emulsion having particle size tyically in the range of 2-5 microns. This material is kept at 120° F. under which conditions the gelatin will not jell.

Coascervation is induced by adding, slowly and uniformly 40 parts of a 20% aqueous solution of sodium sulphate. During coascervation the gelatin molecules are deposited uniformly about each oil droplet as a nucleus.

Gelation is effected by pouring the heated coascervate mixture into 1,000 parts by weight of 7% aqueous solution of sodium sulphate at 65° F. The resulting jelled coascervate may be filtered and washed at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XXXIII

Chewing Gum

100 Parts by weight of chicle are mixed with 4 parts by weight of the flavor prepared in accordance with Example XXIX. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting walnut flavor.

EXAMPLE XXXIV

Chewing Gum

100 Parts by weight of chicle are mixed with 18 parts by weight of the flavor prepared in accordance with Example XXXII. 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting walnut flavor.

EXAMPLE XXXV

Toothpaste Formulation

The following separate groups of ingredients are prepared:

| Parts by Weight | Ingredient |
|---|---|
| Group "A" | |
| 30.200 | Glycerine |
| 15.325 | Distilled water |
| .100 | Sodium Benzoate |
| .125 | Saccharin Sodium |
| .400 | Stannous Fluoride |
| Group "B" | |
| 12.500 | Calcium Carbonate |
| 37.200 | Dicalsium Phosphate (Dihydrate) |
| Group "C" | |
| 2.000 | Sodium N-Lauroyl Sarcosinate (foaming agent |
| Group "D" | |
| 1.200 | Flavor Material of Example XXXI |
| 100.00 (Total) | |

PROCEDURE:
1. The ingredients in Group "A" are stirred and heated in a steam jacketed kettle to 160° F.
2. Stirring is continued for an additional three to five minutes to form a homogeneous gel
3. The powders of Group "B" are added to the gel, while mixing, until a homogeneous paste is formed
4. With stirring, the flavor of "D" is added and lastly the sodium n-lauroyl sarcosinate
5. The resultant slurry is then blended for one hour. The completed paste is then transferred to a three roller mill and then homogenized, and finally tubed.

The resulting toothpaste when used in a normal toothbrushing procedure yields a pleasant walnut flavor, of constant strong intensity throughout said procedure (1–1.5 minutes).

EXAMPLE XXXVI

Chewable Vitamin Tablets

The flavor material produced according to the process of Example XXV is added to a Chewable Vitamin Tablet Formulation at a rate of 10 gm/Kg which chewable vitamin tablet formulation is prepared as follows:

In a Hobart Mixer the following materials are blended to homogeneity:

| | Gms/1000 tablets |
|---|---|
| Vitamin C (ascorbic acid) as ascorbic acid-sodium ascorbate mixture 1:1 | 70.00 |
| Vitamin $B_1$ (thiamine mononitrate) as Rocoat® thiamine mononitrate 33⅓% (Hoffman La Roche) | 4.0 |
| Vitamin $B_2$ (riboflavin) as Rocoat® riboflavin 33⅓% | 5.0 |
| Vitamin B (pyridoxine hydrochloride) as Rocoat® pyridoxine hydrochloride 33⅓% | 4.0 |
| Niacinamide as Rocoat® niacinamide 33⅓% | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Flavor of Example XXXI | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 G dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong walnut flavor for a period of 12 minutes.

EXAMPLE XXXVII

Chewing Tobacco

Onto 100 pounds of tobacco for chewing (85% Wisconsin leaf and 15% Pennsylvania leaf) the following casing is sprayed at the rate of 30%.

| Ingredients | Parts by Weight |
|---|---|
| Corn Syrup | 60 |
| Licorice | 10 |
| Glycerine | 20 |
| Fig Juice | 4.6 |
| Prune Juice | 5 |
| Flavor Material of Example XXXI | 0.4 |

The resultant product is redried to a moisture content of 20%. On chewing, this tobacco has an excellent substantially consistent, long-lasting walnut nuance in conjunction with the sweet tobacco note.

What is claimed is:

1. A process for augmenting or enhancing the aroma or taste of a smoking tobacco comprising the step of intimately admixing with smoking tobacco an aroma or taste augmenting or enhancing quantity of at least one oxobicyclo compound defined according to the structure:

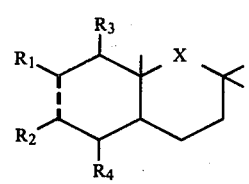

wherein X represents the moiety:

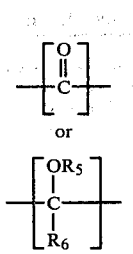

or wherein the dashed line represents a carbon-carbon single bond or a carbon-carbon double bond; wherein $R_1$, $R_2$, $R_3$ and $R_4$ is each selected from the group consisting of hydrogen and methyl; wherein $R_5$ is hydrogen; wherein $R_6$ represents hydrogen or methyl; with the provisos that (i) at least three of $R_1$, $R_2$, $R_3$ and $R_4$ represent hydrogen and (ii) that when the dashed line is a carbon-carbon single bond and X is the moiety:

then one of $R_1$, $R_2$, $R_3$ or $R_4$ is methyl and the others of $R_1$, $R_2$, $R_3$ or $R_4$ is hydrogen.

2. The process of claim 1 wherein the oxobicyclo compounds contained in the smoking tobacco composition have the structures:

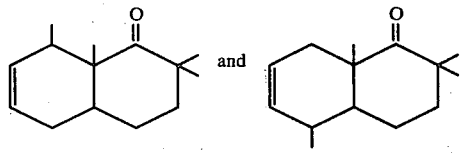

3. A smoking tobacco composition comprising smoking tobacco and intimately admixed therewith at least one oxobicyclo compound having the structure:

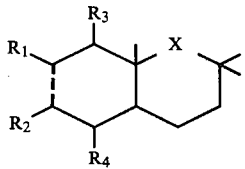

wherein X represents the moiety:

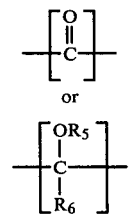

wherein the dashed line represents a carbon-carbon single bond or a carbon-carbon double bond; wherein $R_1$, $R_2$, $R_3$ and $R_4$ is each selected from the group consisting of hydrogen and methyl; wherein $R_5$ is hydrogen; wherein $R_6$ represents hydrogen or methyl; with the provisos that (i) at least three of $R_1$, $R_2$, $R_3$ and $R_4$ represent hydrogen and (ii) that when the dashed line is a carbon-carbon single bond and X is the moiety:

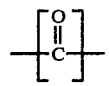

then one of $R_1$, $R_2$, $R_3$ or $R_4$ is methyl and the others of $R_1$, $R_2$, $R_3$ or $R_4$ is hydrogen.

4. A smoking tobacco article comprising a cylindrically shaped body of smoking tobacco having a side and two ends; a wrapper in substantially total contact with said side; and a filter in contact with one of said ends and in intimate contact with said filter, said wrapper or said cylindrically shaped body of smoking tobacco an aroma augmenting or enhancing quantity of at least one oxobicyclo compound having the structure:

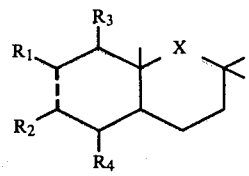

wherein X represents the moiety:

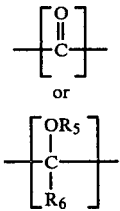

wherein the dashed line represents a carbon-carbon single bond or a carbon-carbon double bond; wherein $R_1$, $R_2$, $R_3$ and $R_4$ is each selected from the group consisting of hydrogen and methyl; wherein $R_5$ is hydrogen; wherein $R_6$ represents hydrogen or methyl; with the provisos that (i) at least three of $R_1$, $R_2$, $R_3$ and $R_4$ represent hydrogen and (ii) that when the dashed line is a carbon-carbon single bond and X is the moiety:

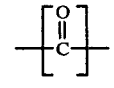

then one of $R_1$, $R_2$, $R_3$ or $R_4$ is methyl and the others of $R_1$, $R_2$, $R_3$ or $R_4$ is hydrogen.

* * * * *